US011203637B2

(12) United States Patent
Zhang et al.

(10) Patent No.: US 11,203,637 B2
(45) Date of Patent: Dec. 21, 2021

(54) ANTI-TIM-3 ANTIBODIES AND USE THEREOF

(71) Applicant: BeiGene, Ltd., Grand Cayman (KY)

(72) Inventors: Tong Zhang, Beijing (CN); Liu Xue, Beijing (CN); Qi Liu, Beijing (CN); Hao Peng, Beijing (CN); Min Wei, Beijing (CN); Kang Li, Beijing (CN)

(73) Assignee: BEIGENE, LTD., Grand Cayman (KY)

( * ) Notice: Subject to any disclaimer, the term of this patent is extended or adjusted under 35 U.S.C. 154(b) by 415 days.

(21) Appl. No.: 16/328,047

(22) PCT Filed: Aug. 25, 2017

(86) PCT No.: PCT/CN2017/099098
§ 371 (c)(1),
(2) Date: Feb. 25, 2019

(87) PCT Pub. No.: WO2018/036561
PCT Pub. Date: Mar. 1, 2018

(65) Prior Publication Data
US 2019/0276533 A1 Sep. 12, 2019

(30) Foreign Application Priority Data
Aug. 26, 2016 (WO) ............... PCT/CN2016/096924

(51) Int. Cl.
| A61P 37/00 | (2006.01) |
| C07K 16/28 | (2006.01) |
| A61P 35/00 | (2006.01) |
| A61K 39/395 | (2006.01) |
| A61K 39/00 | (2006.01) |

(52) U.S. Cl.
CPC ........ *C07K 16/2803* (2013.01); *A61K 39/395* (2013.01); *A61P 35/00* (2018.01); *A61P 37/00* (2018.01); *C07K 16/2818* (2013.01); *A61K 2039/505* (2013.01); *A61K 2039/507* (2013.01); *C07K 2317/24* (2013.01); *C07K 2317/565* (2013.01); *C07K 2317/71* (2013.01); *C07K 2317/76* (2013.01); *C07K 2317/77* (2013.01); *C07K 2317/92* (2013.01)

(58) Field of Classification Search
CPC .................................................. C07K 16/2803
USPC .................................................... 424/133.1
See application file for complete search history.

(56) References Cited

U.S. PATENT DOCUMENTS

| 4,376,110 | A | 3/1983 | David |
| 7,563,874 | B2 | 7/2009 | Marks et al. |
| 7,989,597 | B2 | 8/2011 | Chang et al. |
| 8,735,553 | B1 | 5/2014 | Li et al. |
| 2012/0189617 | A1 | 7/2012 | Takayanagi et al. |
| 2014/0044728 | A1 | 2/2014 | Takayanagi et al. |
| 2015/0086574 | A1 | 3/2015 | Karsunky et al. |
| 2017/0088616 | A1 | 3/2017 | Takayanagi et al. |

FOREIGN PATENT DOCUMENTS

| CN | 103079644 | 5/2013 |
| CN | 103721255 | 4/2014 |
| WO | WO 2003/063792 | 8/2003 |
| WO | WO 2009/052623 | 4/2009 |
| WO | WO 2015/117002 | 8/2015 |
| WO | WO 2016/000619 | 1/2016 |
| WO | WO 2016/068803 | 5/2016 |
| WO | WO 2016/071448 | 5/2016 |
| WO | WO 2018/036561 | 3/2018 |

OTHER PUBLICATIONS

International Search Report and Written Opinion for International Application No. PCT/CN2017/099098, dated Nov. 17, 2017, 13 pages.
Anderson, A. C. et al., "TIM-3 in autoimmunity," Current Opinion in Immunology, 18(6):665-669 (Dec. 2006).
Anderson, A. C. et al., "Promotion of Tissue Inflammation by the Immune Receptor Tim-3 Expressed on Innate Immune Cells," Science, 318(5853):1141-1143 (Nov. 2007).
Anderson, A. C., "Tim-3, a negative regulator of anti-tumor Immunity," Current Opinion in Immunology, 24(2):213-216 (Jan. 2012).
Anderson, A. C. et al., "Lag-3, Tim-3, and TIGIT: Co-inhibitory Receptors with Specialized Functions in Immune Regulation," Immunity, 44:989-1004 (May 2016).
Arai, Y. et al., "Upregulation of TIM-3 and PD-1 on CD4+ and CD8+ T Cells Associated with Dysfunction of Cell-Mediated Immunity after Colorectal Cancer Operation," Yonago Acta Medica, 55:1-9 (2012).
Boeckh, M. et al., "Cytomegalovirus: pathogen, paradigm, and puzzle," J. Clin. Invest., 121 (5):1673-1680 (May 2011).
Brocks, B. et al., "Species-crossreactive scFv against the tumor stroma marker 'fibroblast activation protein' selected by phage display from an immunized FAP-/- knock-out mouse," Mol. Med., 7(7):461-469 (Jul. 2001).
Cao, Y. et al., "Tim-3 Expression in Cervical Cancer Promotes Tumor Metastasis," PLoS ONE 8(1): e53834. doi:10.1371/journal.pone.0053834 (2013).
Chabtini, L. et al., "TIM-3 Regulates Innate Immune Cells to Induce Fetomaternal Tolerance," The Journal of Immunology, 190:88-96 (2013).
Chothia, C. et al., "Canonical Structures for the Hypervariable Regions of Immunoglobulins," J. Mol. Biol. 196:901-917 (1987).
Chothia, C. et al., "Conformations of immunoglobulin hypervariable regions," Nature 342:877-883 (Dec. 1989).

(Continued)

*Primary Examiner* — Sean E Aeder
(74) *Attorney, Agent, or Firm* — Cooley LLP

(57) ABSTRACT

Provided are antibodies that specifically bind to T-cell immunoglobulin domain and mucin domain 3 (Tim-3). The anti-Tim-3 antibodies can be used to treat, prevent or diagnose immune, cancerous, infectious diseases or other pathological disorders that may be modulated by Tim-3-mediated functions.

29 Claims, 8 Drawing Sheets
Specification includes a Sequence Listing.

(56) References Cited

OTHER PUBLICATIONS

Clayton, K. L. et al., "T Cell Ig and Mucin Domain-Containing Protein 3 is Recruited to the Immune Synapse, Disrupts Stable Synapse Formation, and Associates with Receptor Phosphatases," The Journal of Immunology, 192:782-791 (2014).
Da Silva, I. P. et al., "Reversal of NK-Cell Exhaustion in Advanced Melanoma by Tim-3 Blockade," Cancer Immunol. Res., 2(5):1-13 (May 2014). Published Online First Feb. 11, 2014; DOI: 10.1158/2326-6066.CIR-13-0171.
De St. Groth, S. F. et al., "Production of monoclonal antibodies: strategy and tactics," Journal of Immunological Methods, 35:1-21 (1980).
DeKruyff, R. H. et al., "T Cell/Transmembrane, Ig, and Mucin-3 Allelic Variants Differentially Recognize Phosphatidylserine and Mediate Phagocytosis of Apoptotic Cells," The Journal of Immunology, 184:1918-1930 (Jan. 2010).
Dietze, K. K. et al., "Combining Regulatory T Cell Depletion and Inhibitory Receptor Blockade Improves Reactivation of Exhausted Virus-Specific CD8+ T Cells and Efficiently Reduces Chronic Retroviral Loads," PLoS Pathog 9(12): e1003798. doi:10.1371/journal.ppat.1003798 (2013).
Fadok, V. A. et al., "Macrophages that have ingested apoptotic cells in vitro inhibit proinflammatory cytokine production through autocrine/paracrine mechanisms involving TGF-beta, PGE2, and PAF," J Clin Invest, 101(4):890-898 (Feb. 1998).
Fischer, E. et al., "Radioimmunotherapy of Fibroblast Activation Protein Positive Tumors by Rapidly Internalizing Antibodies," Clinical Cancer Research, 18(22):6208-6218 (2012).
Fourcade, J. et al., "Upregulation of Tim-3 and PD-1 expression is associated with tumor antigen-specific CD8+ T cell dysfunction in melanoma patients," The Journal of Experimental Medicine, 207(10):2175-2186 (Sep. 2010).
Fourcade, J. et al., "PD-1 and Tim-3 Regulate the Expansion of Tumor Antigen-Specific CD8+ T Cells Induced by Melanoma Vaccines," Cancer Research, 74(4):1045-1055 (Feb. 2014).
Frey, B. et al., "The immune functions of phosphatidylserine in membranes of dying cells and microvesicles," Semin. Immunopathol., 33(5)497-516 (Sep. 2011).
Glanville, J. et al., "Precise determination of the diversity of a combinatorial antibody library gives insight into the human immunoglobulin repertoire," PNAS, 106(48):20216-20221 (Dec. 2009).
Golden-Mason, L. et al., "Negative Immune Regulator Tim-3 is Overexpressed on T Cells in Hepatitis C Virus Infection and its Blockade Rescues Dysfunctional CD4+ and CD8+ T Cells," Journal of Virology, 83(18):9122-9130 (Sep. 2009).
Gros, A. et al., "PD-1 identifies the patient-specific CD8+ tumor-reactive repertoire infiltrating human tumors," J Clin Invest., 124(5):2246-2259 (2014).
Hastings, W. D. et al., "TIM-3 is expressed on activated human CD4+ T cells and regulates Th1 and Th17 cytokines," Eur. J. Immunol., 39(9):2492-2501 (Sep. 2009).
Heon, E. K. et al., "IL-15 induces strong but short-lived tumor-infiltrating CD8 T cell responses through the regulation of Tim-3 in breast cancer," Biochem Biophys Res Commun., 464(1):360-366 (Aug. 2015).
Hurwitz, E. et al., "Suppression and promotion of tumor growth by monoclonal antibodies to ErbB-2 differentially correlate with cellular uptake," Proc. Natl. Acad. Sci. USA, 92(8):3353-3357 (Apr. 1995).
Jiang, J. et al., "Decreased Galectin-9 and Increased Tim-3 Expression are Related to Poor Prognosis in Gastric Cancer," PLoS ONE 8(12): e81799. doi:10.1371/journal.pone.0081799 (Dec. 2013).
Jin, H-T et al., "Cooperation of Tim-3 and PD-1 in CD8 T-cell exhaustion during chronic viral infection," Proc Natl Acad Sci USA, 107(33):14733-14738 (Aug. 2010).
Jones, R. B. et al., "Tim-3 expression defines a novel population of dysfunctional T cells with highly elevated frequencies in progressive HIV-1 infection," J. Exp. Med., 205(12):2763-2779 (Nov. 2008).

Kabat, E. A., "The structural basis of antibody complementarity," Adv. Prot. Chem., 32:1-75 (1978).
Kabat, E. A. et al., "Unusual distributions of amino acids in complementarity-determining (hypervariable) segments of heavy and light chains of immunoglobulins and their possible roles in specificity of antibody-combining sites," J. Biol. Chem., Oct. 10, 1977;252(19):6609-6616.
Kabat, E. A. et al., "Sequences of Proteins of Immunological Interest," vol. I, Fifth Edition, U.S. Department of Health and Human Services, Public Health Service National Institutes of Health (1991), 152 pages.
Komohara, Y. et al., "The Coordinated Actions of TIM-3 on Cancer and Myeloid Cells in the Regulation of Tumorigenicity and Clinical Prognosis in Clear Cell Renal Cell Carcinomas," Cancer Immunology Research, 3(9):999-1007 (Sep. 2015). Published Online First Mar. 17, 2015.
Lefranc, M-P et al., "IMGT, the international ImMumoGeneTics database," Nucleic Acids Research, 27(1):209-212 (1999).
Li, H. et al., "Tim-3/galectin-9 Signaling Pathway Mediates T-Cell Dysfunction and Predicts Poor Prognosis in Patients with Hepatitis B Virus-Associated Hepatocellular Carcinoma," Hepatology, 56:1342-1351 (2012).
Liu, L. et al., "LY2875358, a Neutralizing and Internalizing Anti-MET Bivalent Antibody, Inhibits HGF-Dependent and HGF-Independent MET Activation and Tumor Growth," Clin. Cancer Res. 20(23):6059-6070 (2014).
Mechetner, E., "Development and Characterization of Mouse Hybridomas," Chapter 1 In: Methods in Molecular Biology, vol. 378: Monoclonal Antibodies: Methods and Protocols, Edited by: M. Albitar, Humana Press Inc., Totowa, NJ (2007).
Monney, L. et al., "Th1-specic cell surface protein Tim-3 regulates macrophage activation and severity of an autoimmune disease," Nature, 415:536-541 (Jan. 2002).
Moorman, J. P. et al., "Tim-3 Pathway Controls Regulatory and Effector T Cell Balance during Hepatitis C Virus Infection," The Journal of Immunology, 189:755-766 (2012).
McIntire, J. J. et al., "Identification of Tapr (an airway hyperreactivity regulatory locus) and the linked Tim gene family," Nat. Immunol., 2(12): 1109-1116 (Dec. 2001).
Mujib, S. et al., "Antigen-Independent Induction of Tim-3 Expression on Human T Cells by the Common y-Chain Cytokines IL-2, IL-7, IL-15, and IL-21 is Associated with Proliferation and is Dependent on the Phosphoinositide 3-Kinase Pathway," The Journal of Immunology, 188:3745-3756 (2012).
Nakayama, M., "Tim-3 mediates phagocytosis of apoptotic cells and cross-presentation," Blood, 113(16):3821-3830 (Apr. 2009).
Ndhlovu, L. C. et al., "Tim-3 marks human natural killer cell maturation and suppresses cell-mediated cytotoxicity," Blood, 119(16):3734-3743 (2012).
Phong, B. L. et al., "Tim-3 enhances FcERI-proximal signaling to modulate mast cell activation," J. Exp. Med., 212(13):2289-2304 (Dec. 2015). doi: 10.1084/jem.20150388. Epub Nov. 23, 2015.
Poul, M-A et al., "Selection of Tumor-Specific Internalizing Human Antibodies from Phage Libraries," J. Mol. Biol., 301:1149-1161 (2000).
Sabatos, C. A. et al., "Interaction of Tim-3 and Tim-3 ligand regulates T helper type 1 responses and induction of peripheral tolerance," Nature Immunology, 4(11): 1102-1110 (Nov. 2003).
Sakhdari, A. et al., "Tim-3 Negatively Regulates Cytotoxicity in Exhausted CD8+ T Cells in HIV Infection," PLoS ONE 7(7): e40146. doi:10.1371/journal.pone.0040146 (2012).
Sanchez-Fueyo, A. et al., "Tim-3 inhibits T helper type 1-mediated auto- and alloimmune responses and promotes immunological tolerance," Nature Immunology, 4(11):1093-1101 (Nov. 2003).
Thommen, D. S. et al., "Progression of Lung Cancer is Associated with Increased Dysfunction of T Cells Defined by Coexpression of Multiple Inhibitory Receptors," Cancer Immunology Research, 3(12):1344-1355 (Dec. 2015).
Tomkowicz, B. et al., "TIM-3 Suppresses Anti-CD3/CD28-Induced TCR Activation and IL-2 Expression through the NFAT Signaling Pathway," PLoS ONE 10(10): e0140694. doi:10.1371/journal (2015).

(56) References Cited

OTHER PUBLICATIONS

Wu, T. T. et al., "An analysis of the sequences of the variable regions of bence jones proteins and myeloma light chains and their implications for anti-body complementarity," J. Exp. Med., 132(2):211-250 (Aug. 1970).

Xu, B. et al., "Circulating and tumor-infiltrating Tim-3 in patients with colorectal cancer," Oncotarget, 6(24):20592-20603 (Aug. 2015). Published online May 12, 2015.

Zhu, C. et al., "The Tim-3 ligand galectin-9 negatively regulates T helper type 1 immunity," Nature Immunology, 6(12):1245-1252 (Dec. 2005).

Zhuang, X. et al., "Ectopic Expression of TIM-3 in Lung Cancers. A Potential Independent Prognostic Factor for Patients With NSCLC," Am. J. Clin. Pathol., 137:978-985 (2012).

Sakuishi, K. et al., "Targeting Tim-3 and PD-1 pathways to reverse T cell exhaustion and restore anti-tumor immunity," J. Exp. Med., 207(10):2187-2194 (Dec. 2010).

Kearley, J. et al., "Th2-driven, allergen-induced airway inflammation is reduced after treatment with anti-Tim-3 antibody in vivo," J. Exp. Med., 204(6): 1289-1294 (Jun. 2007).

Xiang, J. et al., "Complementarity determining region residues aspartic acid at H55, serine at H95 and tyrosines at H97 and L96 play important roles in the B72.3 antibody-TAG72 antigen interaction," Protein Eng., 1996, vol. 9, No. 6, pp. 539-543.

Dougan, D. A. et al., "Effects of substitutions in the binding surface of an antibody on antigen affinity," Protein Eng., 1998, vol. 11, No. 1, pp. 65-74.

Lin, Y. et al., "Improved affinity of a chicken single-chain antibody to avian infectious bronchitis virus by site-directed mutagenesis of complementarity-determining region H3," African J. Biotech., 2011, vol. 10, pp. 18294-18302.

ANTI-TIM-3 ANTIBODIES AND USE THEREOF

CROSS-REFERENCE TO RELATED APPLICATIONS

This application is the U.S. national stage application to International Patent Application No. PCT/CN2017/099098, filed Aug. 25, 2017, which claims the benefit of priority to International Application No. PCT/CN2016/096924 filed on Aug. 26, 2016, the entire contents of each of which are incorporated herein by reference.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: BEIG_021_01US_SeqList_ST25.txt, date recorded: Feb. 22, 2019, file size 53 kilobytes).

FIELD OF THE INVENTION

Disclosed herein are antibodies that specifically bind to T-cell immunoglobulin domain and mucin domain 3 (Tim-3).

BACKGROUND OF THE INVENTION

T-cell immunoglobulin domain and mucin domain 3 (Tim-3, HAVCR2, or CD366) is a 33 KD type I transmembrane glycoprotein, a member of the T-cell Immunoglobulin- and mucin-domain-containing family that plays an important role in promoting T-cell exhaustion in both chronic viral infections and tumor escape from immune surveillance (Monney et al., 2002 *Nature* 415:536-541; Sanchez-Fueyo A, et al., 2003 *Nat Immunol.* 4:1093-101; Sabatos C A, et al., 2003 *Nat Immunol.* 4:1102-10; Anderson et al., 2006 *Curr Opin Immunol.* 18:665-669). The genes and cDNAs coding for Tim-3 were cloned and characterized in mouse and human (Monney et al., 2002 *Nature* 415:536-541; McIntire et al., 2001 *Nat. Immunol.* 2:1109-1116). Mature human Tim-3 contains 280 amino acid residues (NCBI accession number: NP_116171.3). Its extracellular domain consists of amino acid residues 1-181, and the transmembrane domain and cytoplasmic C-terminal tail comprises residues 182-280. There are no known inhibitory signaling motifs, such as immunoreceptor tyrosine-based inhibitory motif (ITIM) and tyrosine switch motif (ITSM), found in the cytoplasmic domain.

Tim-3 was initially identified in Th1 cells. Subsequent studies showed that in addition to T cells, Tim-3 was also expressed in other types of immune cells, such as NK cells, macrophages, DCs, and mast cells (Hastings et al., 2009 *Eur J Immunol* 39:2492-2501; Anderson et al., 2007 *Science* 318: 1141-1143; Phong B L, et al., 2015 *J Exp Med. pii: jem.* 20150388). Tim-3 is rarely expressed in other human tissues. In T cells, Tim-3 expression is positively regulated through TCR/CD3 activation (Hastings et al., 2009 *Eur J Immunol* 39:2492-2501). In addition, common γ chain cytokines (e.g., IL-2, IL-7, IL-15 and IL-21) also increase Tim-3 expression in a PI-3 kinase-dependent manner (Mujib S, et al., 2012 *J Immunol.* 188:3745-56). T cells in tumor microenvironment (TME) often co-express Tim-3 with other "checkpoint" inhibitory immune receptors, such as PD-1, Lag-3 and Tigit (Fourcade J, et al., 2010 *J Exp Med.* 207:2175-86; Gros A, et al., 2014 *J Clin Invest.* 124:2246-59).

Up to date, several Tim-3 ligands (Tim-3L) have been reported, which include galectin-9 and phosphatidylserine (PtdSer), being considered as two major ones (Anderson A C, 2012 *Curr Opin Immunol.* 24:213-6). Binding of Tim-3Ls to Tim-3 receptor induces intracellular signaling that inhibits T-cell activation, leading to diminished cell proliferation, IL-2 and IFN-γ secretion (Dekruyff et al., 2010 *J. Immunol.* 184:1918-1930; Zhu et al., 2005 *Nat. Immunol.* 6:1245-1252). The detailed mechanisms of Tim-3 signaling in T cells still remain largely unknown. Some studies have shown that Tim-3 could be recruited to the immunological synapses and sequester Src kinase Lck when interacting with TCR, whereby inhibiting its signaling, especially NFAT signaling pathway (Tomkowicz B, et al., 2015 *PLoS One* 10:e0140694; Clayton K L, et al., 2014 *J. Immunol.* 192: 782-91).

In the cancer and viral infections, activation of Tim-3 signaling promotes immune cell dysfunction, leading to the cancer outgrowth or extended viral infection. Up-regulation of Tim-3 expression in tumor-infiltrating lymphocytes (TILs), macrophages and tumor cells has been reported in many types of cancers such as lung (Zhuang X, et al., *Am J Clin Pathol* 2012 137: 978-985), liver (Li H, et al., *Hepatology* 2012 56:1342-1351), stomach (Jiang et al., *PLoS One* 2013 8:e81799), kidney (Komohara et al., *Cancer Immunol Res.* 2015 3:999-1000), breast (Heon E K, et al., 2015 *Biochem Biophys Res Commun.* 464:360-6), colon (Xu et al., *Oncotarget* 2015), melanocytes (Gros A, et al., 2014 *J Clin Invest.* 2014 124:2246-2259) and cervical cancer (Cao et al., *PLoS One* 2013 8:e53834). The increased expression of Tim-3 in those cancers is associated with poor prognosis of patient survival outcome. Not only does up-regulation of Tim-3 signaling play important roles in immune tolerance to cancer, but also to chronic viral infection. During HIV and HCV infections, expression of Tim-3 on T cells was significantly higher compared to that in healthy people and positively correleated with viral loads and disease progression (Jones R B, et al., 2008 *J Exp Med.* 205:2763-79; Sakhdari A, et al., 2012 *PLoS One* 7:e40146; Golden Mason L, et al., 2009 *J Virol.* 83:9122-30; 2012 Moorman J P, et al., *J Immunol.* 189:755-66). In addition, blockade of Tim-3 receptor alone or in combination with PD-1/PD-L1 blocakde could rescue functionally "exhausted" T cells both in vitro and in vivo (Dietze K K, et al., 2013 *PLoS Pathog* 9:e1003798; Golden-Mason L, et al., 2009 *J Virol.* 83:9122-30). Therefore, modulation of Tim-3 signaling by therapeutic agents may rescue immune cells, e.g., T cells, NK cells and macrophages (Mφ), from tolerance, inducing efficient immune responses to eradicate tumors or chronic viral infections.

It has been reported that some antibodies can be internalized upon binding to its target on the cell surface (Hurwitz E, et al., 1995, *Proc Natl Acad Sci USA* 92:3353-7; Poul M A, et al., 2000, *J Mol Biol.* 301:1149-61; Fischer E, et al., 2012, *Clin Cancer Res.* 18:6208-18). Antibody-induced receptor endocytosis leads to down-modulation of receptors on the cell surface and inhibition of receptor-dependent signaling (Liu L, et al., 2014, *Clin Cancer Res.* 20:6059-70). As antibody internalization will reduce surface expression of a receptor, a persistent internalization is usually desirable for an antibody of the receptor.

Therefore, there is a need of an anti-Tim-3 antibody which has a high affinity and specificity to Tim-3 receptor and preferably further has a persistent internalization of Tim-3 receptor.

SUMMARY OF THE INVENTION

Disclosed herein are antibody molecules that bind to Tim-3 with high affinity and specificity. In particular, the anti-Tim-3 antibody disclosed herein provides a persistent or durable internalization of Tim-3 receptor. Also provided are nucleic molecules encoding the antibody molecules, expression vectors, host cells and methods for making the antibody molecules. Pharmaceutical compositions comprising the antibody molecules are also provided. The anti-Tim-3 antibody molecules disclosed herein can be used, alone or in combination with other agents or therapeutic modalities, to treat, prevent and/or diagnose diseases that are associated with suppression of immune cells by Tim-3-mediated intracellular signaling, e.g., immune disorders, cancer, infectious disease, Crohn's disease, sepsis, systemic inflammatory response syndrome (SIRS), and glomerulonephritis. Thus, compositions and methods for treating various disorders or diseases mentioned above using the anti-Tim-3 antibody molecules are disclosed herein, and use of the anti-Tim-3 antibody molecules in manufacturing medicine for treating various disorders or diseases mentioned above, are also provided.

In certain aspects, this disclosure provides an anti-Tim-3 antibody capable of binding to human Tim-3, which includes at least one, two, three, four, five, or six complementarity determining regions (CDR's) comprising an amino acid sequence of SEQ ID NOs 3-8, or 26-27 or variants thereof comprising one or more conservative substitutions.

In some embodiments, the anti-Tim-3 antibody includes at least one, two or three CDRs from a heavy chain variable region (VH) comprising an amino acid sequence of SEQ ID NOs 3-5 or 26 or variants thereof comprising one or more conservative substitutions. In some embodiments, the anti-Tim-3 antibody includes at least one, two or three CDRs from a light chain variable region (VL) comprising an amino acid sequence of SEQ ID NOs 6-8 or 27 or variants thereof comprising one or more conservative substitutions.

In some embodiments, the anti-Tim-3 antibody includes at least one, two, three, four, five or six CDRs from a heavy and light chain variable region comprising an amino acid sequence of SEQ ID NOs 3-8, or 26-27 or variants thereof comprising one or more conservative substitutions.

In some embodiments, the anti-Tim-3 antibody includes six CDRs from a heavy and light chain variable region comprising an amino acid sequence of SEQ ID NOs 3-8, or 26-27 or variants thereof comprising one or more conservative substitutions.

In some embodiments, the anti-Tim-3 antibody comprises:
(a) a heavy chain variable region (VH) comprising one, two or three CDR amino acid sequences selected form SEQ ID NOs 3, 4, 5, or 26 or variants thereof comprising one or more conservative substitutions; and/or
(b) a light chain variable region (VL) comprising one, two or three CDR amino acid sequences selected form SEQ ID NOs 6, 7, 8, or 27 or variants thereof comprising one or more conservative substitutions.

In some embodiments, the anti-Tim-3 antibody comprises:
(a) a heavy chain variable region (VH) comprising a VH-CDR1 amino acid sequence of SEQ ID NO 3 or variants thereof comprising one or more conservative substitutions, a VH-CDR2 amino acid sequence of SEQ ID NO 4 or variants thereof comprising one or more conservative substitutions and a VH-CDR3 amino acid sequence of SEQ ID NO 5 or variants thereof comprising one or more conservative substitutions; and a light chain variable region (VL) comprising a VL-CDR1 amino acid sequence of SEQ ID NO 6 or variants thereof comprising one or more conservative substitutions, a VL-CDR2 amino acid sequence of SEQ ID NO 7 or variants thereof comprising one or more conservative substitutions and a VL-CDR3 amino acid sequence of SEQ ID NO 8 or variants thereof comprising one or more conservative substitutions;
(b) a heavy chain variable region (VH) comprising a VH-CDR1 amino acid sequence of SEQ ID NO 3 or variants thereof comprising one or more conservative substitutions, a VH-CDR2 amino acid sequence of SEQ ID NO 26 or variants thereof comprising one or more conservative substitutions and a VH-CDR3 amino acid sequence of SEQ ID NO 5 or variants thereof comprising one or more conservative substitutions; and a light chain variable region (VL) comprising a VL-CDR1 amino acid sequence of SEQ ID NO 6 or variants thereof comprising one or more conservative substitutions, a VL-CDR2 amino acid sequence of SEQ ID NO 7 or variants thereof comprising one or more conservative substitutions and a VL-CDR3 amino acid sequence of SEQ ID NO 8 or variants thereof comprising one or more conservative substitutions;
(c) a heavy chain variable region (VH) comprising a VH-CDR1 amino acid sequence of SEQ ID NO 3 or variants thereof comprising one or more conservative substitutions, a VH-CDR2 amino acid sequence of SEQ ID NO 4 or variants thereof comprising one or more conservative substitutions and a VH-CDR3 amino acid sequence of SEQ ID NO 5 or variants thereof comprising one or more conservative substitutions; and a light chain variable region (VL) comprising a VL-CDR1 amino acid sequence of SEQ ID NO 6 or variants thereof comprising one or more conservative substitutions, a VL-CDR2 amino acid sequence of SEQ ID NO 7 or variants thereof comprising one or more conservative substitutions and a VL-CDR3 amino acid sequence of SEQ ID NO 27 or variants thereof comprising one or more conservative substitutions; or
(d) a heavy chain variable region (VH) comprising a VH-CDR1 amino acid sequence of SEQ ID NO 3 or variants thereof comprising one or more conservative substitutions, a VH-CDR2 amino acid sequence of SEQ ID NO 26 or variants thereof comprising one or more conservative substitutions and a VH-CDR3 amino acid sequence of SEQ ID NO 5 or variants thereof comprising one or more conservative substitutions; and a light chain variable region (VL) comprising a VL-CDR1 amino acid sequence of SEQ ID NO 6 or variants thereof comprising one or more conservative substitutions, a VL-CDR2 amino acid sequence of SEQ ID NO 7 or variants thereof comprising one or more conservative substitutions and a VL-CDR3 amino acid sequence of SEQ ID NO 27 or variants thereof comprising one or more conservative substitutions.

In some embodiments, the anti-Tim-3 antibody comprises:
(a) a heavy chain variable region (VH) comprising a VH-CDR1 amino acid sequence of SEQ ID NO 3, a VH-CDR2 amino acid sequence of SEQ ID NO 4 and a VH-CDR3 amino acid sequence of SEQ ID NO 5; and a light chain variable region (VL) comprising a VL-CDR1 amino acid sequence of SEQ ID NO 6, a VL-CDR2 amino acid sequence of SEQ ID NO 7 and a VL-CDR3 amino acid sequence of SEQ ID NO 8; or
(b) a heavy chain variable region (VH) comprising a VH-CDR1 amino acid sequence of SEQ ID NO 3, a VH-CDR2 amino acid sequence of SEQ ID NO 26 and a VH-CDR3 amino acid sequence of SEQ ID NO 5; and a light chain variable region (VL) comprising a VL-CDR1 amino acid sequence of SEQ ID NO 6, a VL-CDR2 amino acid sequence of SEQ ID NO 7 and a VL-CDR3 amino acid sequence of SEQ ID NO 27.

In some embodiments, the anti-Tim-3 antibody is a humanized antibody molecule.

In some embodiments, the anti-Tim-3 antibody is a humanized monoclonal antibody (mAb) molecule.

In some embodiments, the antibody comprises a heavy chain variable domain having at least 95%, 96%, 97%, 98%, 99% or 100% sequence identity with the amino acid sequence of SEQ ID NOs 9, 17, 28 or 40. In some embodiments, the antibody comprises a heavy chain variable domain having at least 95%, 96%, 97%, 98%, 99% or 100% sequence identity with the amino acid sequence of SEQ ID NOs 9, 17 or 28. In some embodiments, the anti-Tim-3 antibody comprises a light chain variable domain having at least 95%, 96%, 97%, 98%, 99% or 100% sequence identity with the amino sequence of SEQ ID NOs 11, 19, 30 or 36.

In some embodiments, the anti-Tim-3 antibody comprises:
(a) a heavy chain variable domain having at least 95%, 96%, 97%, 98%, 99% or 100% sequence identity with the amino acid sequence of SEQ ID NO 9, and a light chain variable domain having at least 95%, 96%, 97%, 98%, 99% or 100% sequence identity with the amino acid sequence of SEQ ID NO 11;
(b) a heavy chain variable domain having at least 95%, 96%, 97%, 98%, 99% or 100% sequence identity with the amino acid sequence of SEQ ID NO 9, and a light chain variable domain having at least 95%, 96%, 97%, 98%, 99% or 100% sequence identity with the amino acid sequence of SEQ ID NO 19;
(c) a heavy chain variable domain having at least 95%, 96%, 97%, 98%, 99% or 100% sequence identity with the amino acid sequence of SEQ ID NO 9, and a light chain variable domain having at least 95%, 96%, 97%, 98%, 99% or 100% sequence identity with the amino acid sequence of SEQ ID NO 30;
(d) a heavy chain variable domain having at least 95%, 96%, 97%, 98%, 99% or 100% sequence identity with the amino acid sequence of SEQ ID NO 9, and a light chain variable domain having at least 95%, 96%, 97%, 98%, 99% or 100% sequence identity with the amino acid sequence of SEQ ID NO 36;
(e) a heavy chain variable domain having at least 95%, 96%, 97%, 98%, 99% or 100% sequence identity with the amino acid sequence of SEQ ID NO 17, and a light chain variable domain having at least 95%, 96%, 97%, 98%, 99% or 100% sequence identity with the amino acid sequence of SEQ ID NO 11;
(f) a heavy chain variable domain having at least 95%, 96%, 97%, 98%, 99% or 100% sequence identity with the amino acid sequence of SEQ ID NO 17, and a light chain variable domain having at least 95%, 96%, 97%, 98%, 99% or 100% sequence identity with the amino acid sequence of SEQ ID NO 19;
(g) a heavy chain variable domain having at least 95%, 96%, 97%, 98%, 99% or 100% sequence identity with the amino acid sequence of SEQ ID NO 17, and a light chain variable domain having at least 95%, 96%, 97%, 98%, 99% or 100% sequence identity with the amino acid sequence of SEQ ID NO 30;
(h) a heavy chain variable domain having at least 95%, 96%, 97%, 98%, 99% or 100% sequence identity with the amino acid sequence of SEQ ID NO 17, and a light chain variable domain having at least 95%, 96%, 97%, 98%, 99% or 100% sequence identity with the amino acid sequence of SEQ ID NO 36;
(i) a heavy chain variable domain having at least 95%, 96%, 97%, 98%, 99% or 100% sequence identity with the amino acid sequence of SEQ ID NO 28, and a light chain variable domain having at least 95%, 96%, 97%, 98%, 99% or 100% sequence identity with the amino acid sequence of SEQ ID NO 11;
(j) a heavy chain variable domain having at least 95%, 96%, 97%, 98%, 99% or 100% sequence identity with the amino acid sequence of SEQ ID NO 28, and a light chain variable domain having at least 95%, 96%, 97%, 98%, 99% or 100% sequence identity with the amino acid sequence of SEQ ID NO 19;
(k) a heavy chain variable domain having at least 95%, 96%, 97%, 98%, 99% or 100% sequence identity with the amino acid sequence of SEQ ID NO 28, and a light chain variable domain having at least 95%, 96%, 97%, 98%, 99% or 100% sequence identity with the amino acid sequence of SEQ ID NO 30;
(l) a heavy chain variable domain having at least 95%, 96%, 97%, 98%, 99% or 100% sequence identity with the amino acid sequence of SEQ ID NO 28, and a light chain variable domain having at least 95%, 96%, 97%, 98%, 99% or 100% sequence identity with the amino acid sequence of SEQ ID NO 36;
(m) a heavy chain variable domain having at least 95%, 96%, 97%, 98%, 99% or 100% sequence identity with the amino acid sequence of SEQ ID NO 40, and a light chain variable domain having at least 95%, 96%, 97%, 98%, 99% or 100% sequence identity with the amino acid sequence of SEQ ID NO 11;
(n) a heavy chain variable domain having at least 95%, 96%, 97%, 98%, 99% or 100% sequence identity with the amino acid sequence of SEQ ID NO 40, and a light chain variable domain having at least 95%, 96%, 97%, 98%, 99% or 100% sequence identity with the amino acid sequence of SEQ ID NO 19;
(o) a heavy chain variable domain having at least 95%, 96%, 97%, 98%, 99% or 100% sequence identity with the amino acid sequence of SEQ ID NO 40, and a light chain variable domain having at least 95%, 96%, 97%, 98%, 99% or 100% sequence identity with the amino acid sequence of SEQ ID NO 30; or
(p) a heavy chain variable domain having at least 95%, 96%, 97%, 98%, 99% or 100% sequence identity with the amino acid sequence of SEQ ID NO 40, and a light chain variable domain having at least 95%, 96%, 97%, 98%, 99% or 100% sequence identity with the amino acid sequence of SEQ ID NO 36.

In some embodiments, the anti-Tim-3 antibody comprises:
(a) a heavy chain variable domain having at least 95%, 96%, 97%, 98%, 99% or 100% sequence identity with the amino acid sequence of SEQ ID NO 9, and a light chain variable domain having at least 95%, 96%, 97%, 98%, 99% or 100% sequence identity with the amino acid sequence of SEQ ID NO 11;
(b) a heavy chain variable domain having at least 95%, 96%, 97%, 98%, 99% or 100% sequence identity with the amino acid sequence of SEQ ID NO 9, and a light chain variable domain having at least 95%, 96%, 97%, 98%, 99% or 100% sequence identity with the amino acid sequence of SEQ ID NO 19;
(c) a heavy chain variable domain having at least 95%, 96%, 97%, 98%, 99% or 100% sequence identity with the amino acid sequence of SEQ ID NO 9, and a light chain variable domain having at least 95%, 96%, 97%, 98%, 99% or 100% sequence identity with the amino acid sequence of SEQ ID NO 30;
(d) a heavy chain variable domain having at least 95%, 96%, 97%, 98%, 99% or 100% sequence identity with the amino acid sequence of SEQ ID NO 9, and a light chain variable domain having at least 95%, 96%, 97%, 98%, 99% or 100% sequence identity with the amino acid sequence of SEQ ID NO 36;
(e) a heavy chain variable domain having at least 95%, 96%, 97%, 98%, 99% or 100% sequence identity with the amino acid sequence of SEQ ID NO 17, and a light chain variable domain having at least 95%, 96%, 97%, 98%, 99% or 100% sequence identity with the amino acid sequence of SEQ ID NO 11;
(f) a heavy chain variable domain having at least 95%, 96%, 97%, 98%, 99% or 100% sequence identity with the amino acid sequence of SEQ ID NO 17, and a light chain variable domain having at least 95%, 96%, 97%, 98%, 99% or 100% sequence identity with the amino acid sequence of SEQ ID NO 19;
(g) a heavy chain variable domain having at least 95%, 96%, 97%, 98%, 99% or 100% sequence identity with the amino acid sequence of SEQ ID NO 17, and a light chain variable domain having at least 95%, 96%, 97%, 98%, 99% or 100% sequence identity with the amino acid sequence of SEQ ID NO 30;
(h) a heavy chain variable domain having at least 95%, 96%, 97%, 98%, 99% or 100% sequence identity with the amino acid sequence of SEQ ID NO 17, and a light chain variable domain having at least 95%, 96%, 97%, 98%, 99% or 100% sequence identity with the amino acid sequence of SEQ ID NO 36;
(i) a heavy chain variable domain having at least 95%, 96%, 97%, 98%, 99% or 100% sequence identity with the amino acid sequence of SEQ ID NO 28, and a light chain variable domain having at least 95%, 96%, 97%, 98%, 99% or 100% sequence identity with the amino acid sequence of SEQ ID NO 11;
(j) a heavy chain variable domain having at least 95%, 96%, 97%, 98%, 99% or 100% sequence identity with the amino acid sequence of SEQ ID NO 28, and a light chain variable domain having at least 95%, 96%, 97%, 98%, 99% or 100% sequence identity with the amino acid sequence of SEQ ID NO 19;
(k) a heavy chain variable domain having at least 95%, 96%, 97%, 98%, 99% or 100% sequence identity with the amino acid sequence of SEQ ID NO 28, and a light chain variable domain having at least 95%, 96%, 97%, 98%, 99% or 100% sequence identity with the amino acid sequence of SEQ ID NO 30; or;
(l) a heavy chain variable domain having at least 95%, 96%, 97%, 98%, 99% or 100% sequence identity with the amino acid sequence of SEQ ID NO 28, and a light chain variable domain having at least 95%, 96%, 97%, 98%, 99% or 100% sequence identity with the amino acid sequence of SEQ ID NO 36.

In some embodiments, the anti-Tim-3 antibody comprises:
(a) a heavy chain variable domain comprising the amino acid sequence of SEQ ID NO 9, and a light chain variable domain comprising the amino acid sequence of SEQ ID NO 11;
(b) a heavy chain variable domain comprising the amino acid sequence of SEQ ID NO 17, and a light chain variable domain comprising the amino acid sequence of SEQ ID NO 19;
(c) a heavy chain variable domain comprising the amino acid sequence of SEQ ID NO 28, and a light chain variable domain comprising the amino acid sequence of SEQ ID NO 30;
(d) a heavy chain variable domain comprising the amino acid sequence of SEQ ID NO 28, and a light chain variable domain comprising the amino acid sequence of SEQ ID NO 36;
(e) a heavy chain variable domain comprising the amino acid sequence of SEQ ID NO 40, and a light chain variable domain comprising the amino acid sequence of SEQ ID NO 36.

In some embodiments, the anti-Tim-3 antibody comprises:
(a) a heavy chain variable domain comprising the amino acid sequence of SEQ ID NO 9, and a light chain variable domain comprising the amino acid sequence of SEQ ID NO 11;
(b) a heavy chain variable domain comprising the amino acid sequence of SEQ ID NO 17, and a light chain variable domain comprising the amino acid sequence of SEQ ID NO 19;
(c) a heavy chain variable domain comprising the amino acid sequence of SEQ ID NO 28, and a light chain variable domain comprising the amino acid sequence of SEQ ID NO 30; or
(d) a heavy chain variable domain comprising the amino acid sequence of SEQ ID NO 28, and a light chain variable domain comprising the amino acid sequence of SEQ ID NO 36.

In some embodiments, the anti-Tim-3 antibody comprises a heavy chain having at least 95%, 96%, 97%, 98%, 99% or 100% sequence identity with the amino acid sequence of SEQ ID NO 13, 22 or 32. In some embodiments, the anti-Tim-3 antibody comprises a light chain having at least 95%, 96%, 97%, 98%, 99% or 100% sequence identity with the amino acid sequence of SEQ ID NO 15, 24, 34 or 38.

In some embodiments, the anti-Tim-3 antibody comprises:
(a) a heavy chain having at least 95%, 96%, 97%, 98%, 99% or 100% sequence identity with the amino acid sequence of SEQ ID NO 13, and a light chain having at least 95%, 96%, 97%, 98%, 99% or 100% sequence identity with the amino acid sequence of SEQ ID NO 15;
(b) a heavy chain having at least 95%, 96%, 97%, 98%, 99% or 100% sequence identity with the amino acid sequence of SEQ ID NO 13, and a light chain having at least 95%, 96%, 97%, 98%, 99% or 100% sequence identity with the amino acid sequence of SEQ ID NO 24;
(c) a heavy chain having at least 95%, 96%, 97%, 98%, 99% or 100% sequence identity with the amino acid sequence of SEQ ID NO 13, and a light chain having at least 95%, 96%, 97%, 98%, 99% or 100% sequence identity with the amino acid sequence of SEQ ID NO 34;
(d) a heavy chain having at least 95%, 96%, 97%, 98%, 99% or 100% sequence identity with the amino acid sequence of SEQ ID NO 13, and a light chain having at least 95%, 96%, 97%, 98%, 99% or 100% sequence identity with the amino acid sequence of SEQ ID NO 38;

(e) a heavy chain having at least 95%, 96%, 97%, 98%, 99% or 100% sequence identity with the amino acid sequence of SEQ ID NO 22, and a light chain having at least 95%, 96%, 97%, 98%, 99% or 100% sequence identity with the amino acid sequence of SEQ ID NO 15;
(f) a heavy chain having at least 95%, 96%, 97%, 98%, 99% or 100% sequence identity with the amino acid sequence of SEQ ID NO 22, and a light chain having at least 95%, 96%, 97%, 98%, 99% or 100% sequence identity with the amino acid sequence of SEQ ID NO 24;
(g) a heavy chain having at least 95%, 96%, 97%, 98%, 99% or 100% sequence identity with the amino acid sequence of SEQ ID NO 22, and a light chain having at least 95%, 96%, 97%, 98%, 99% or 100% sequence identity with the amino acid sequence of SEQ ID NO 34;
(h) a heavy chain having at least 95%, 96%, 97%, 98%, 99% or 100% sequence identity with the amino acid sequence of SEQ ID NO 22, and a light chain having at least 95%, 96%, 97%, 98%, 99% or 100% sequence identity with the amino acid sequence of SEQ ID NO 38;
(i) a heavy chain having at least 95%, 96%, 97%, 98%, 99% or 100% sequence identity with the amino acid sequence of SEQ ID NO 32, and a light chain having at least 95%, 96%, 97%, 98%, 99% or 100% sequence identity with the amino acid sequence of SEQ ID NO 15;
(j) a heavy chain having at least 95%, 96%, 97%, 98%, 99% or 100% sequence identity with the amino acid sequence of SEQ ID NO 32, and a light chain having at least 95%, 96%, 97%, 98%, 99% or 100% sequence identity with the amino acid sequence of SEQ ID NO 24;
(k) a heavy chain having at least 95%, 96%, 97%, 98%, 99% or 100% sequence identity with the amino acid sequence of SEQ ID NO 32, and a light chain having at least 95%, 96%, 97%, 98%, 99% or 100% sequence identity with the amino acid sequence of SEQ ID NO 34; or
(l) a heavy chain having at least 95%, 96%, 97%, 98%, 99% or 100% sequence identity with the amino acid sequence of SEQ ID NO 32, and a light chain having at least 95%, 96%, 97%, 98%, 99% or 100% sequence identity with the amino acid sequence of SEQ ID NO 38.

In some embodiments, the anti-Tim-3 antibody comprises:
(a) a heavy chain comprising the amino acid sequence of SEQ ID NO 13, and a light chain comprising the amino acid sequence of SEQ ID NO 15;
(b) a heavy chain comprising the amino acid sequence of SEQ ID NO 22, and a light chain comprising the amino acid sequence of SEQ ID NO 24;
(c) a heavy chain comprising the amino acid sequence of SEQ ID NO 32, and a light chain comprising the amino acid sequence of SEQ ID NO 34; or
(d) a heavy chain comprising the amino acid sequence of SEQ ID NO 32, and a light chain comprising the amino acid sequence of SEQ ID NO 38.

In some embodiments, the anti-Tim-3 antibody comprises one or more of:
(a) a light chain with an Aspartic acid to Glutamic acid mutation at position 1 of SEQ ID NO 24;
(b) a light chain with a Leucine to Methionine mutation at position 4 of SEQ ID NO 24;
(c) a light chain with a Valine to Isoleucine mutation at position 62 of SEQ ID NO 24;
(d) a light chain with a Aspartic acid to Glutamic acid mutation at position 74 of SEQ ID NO 24;
(e) a light chain with a Methionine to Leucine mutation at position 96 of SEQ ID NO 24;
(f) a heavy chain with a Phenylalanine to Tyrosine mutation at position 59 of SEQ ID NO 22;
(g) a heavy chain with a Proline to Valine mutation at position 60 of SEQ ID NO 22;
(h) a heavy chain with a Serine to Threonine mutation at position 77 of SEQ ID NO 22; or
(i) a heavy chain with a Cysteine to Leucine mutation at position 78 of SEQ ID NO 22.

In some embodiments, the anti-Tim-3 antibody is a Fab, F(ab')2, Fv, or a single chain Fv (ScFv).

In some embodiments, the anti-Tim-3 antibody comprises a heavy chain constant region of the subclass of IgG1, IgG2, IgG3, IgG4 or a variant thereof, and a light chain constant region of the type of kappa or lambda or a variant thereof.

In some embodiments, the anti-Tim-3 antibody comprises a variant human IgG1 heavy chain constant region comprising the amino acid sequence of SEQ ID NO 21, and a human kappa light chain constant region.

In some embodiments, the anti-Tim-3 antibody is isolated or recombinant.

In certain aspects, the present disclosure provides a composition, e.g., a pharmaceutical composition, comprising at least one of the antibody molecules described herein, and a pharmaceutically acceptable excipient. In some embodiments, the pharmaceutical composition includes a combination of the anti-Tim-3 antibody and one or more other agents, e.g., a therapeutic agent or other antibody molecule. In some embodiments, the anti-Tim-3 antibody is conjugated to a label or a therapeutic agent.

In certain aspects, the present disclosure also provides a method of stimulating an immune response in a subject. The method comprises administrating to a subject an antibody described herein (e.g., a therapeutically effective amount of an anti-Tim-3 antibody molecule), alone or in combination with one or more agents or procedures.

In certain aspects, the present disclosure also provides a method for treating (e.g., one or more of reducing, inhibiting, or delaying progression of) a cancer or a tumor in a subject. The method comprises, administrating to a subject an antibody described herein (e.g., a therapeutically effective amount of an anti-Tim-3 antibody molecule), alone or in combination with one or more agents or procedures. In some embodiments, the anti-Tim-3 antibody is administrated in combination with a chemotherapy, a targeted therapy, an oncolytic drug, a cytotoxic agent, an immune-based therapy, a cytokine, a surgical procedure, a radiation procedure, an activator of a costimulatory molecule, an inhibitor of an inhibitory molecule, a vaccine, or a cellular immunotherapy. In some embodiments, the anti-Tim-3 antibody is administrated in combination with an inhibitor of an immune checkpoint molecule selected from PD-1, PD-L1, PD-L2, CTLA-4, LAG-3, CEACAM-1, CEACAM-5, VISTA, BTLA, TIGIT, LAIR1, CD160, 2B4 or TGFR. In some embodiments, the anti-Tim-3 antibody is administrated in combination with an anti-PD-1 mAb 317-4B6 (also named Hu317-4B6, 317-4B6/IgG4mt10, described in U.S. Pat. No. 8,735,553).

In certain embodiments, the cancer includes, but is not limited to, a lung cancer, a liver cancer, a stomach cancer, a cervical cancer, a melanoma, a renal cancer, a breast cancer, a colorectal cancer, a leukemia, a lymphoma, an ovarian cancer, a head and neck cancer or a metastatic lesion of the cancer.

In further aspects, this disclosure provides a method of treating an infectious disease, comprising administering to a subject a therapeutically effective amount of an anti-Tim-3 antibody described herein, alone or in combination with one or more agents or procedures. In some embodiments, the infectious disease is a chronic viral infectious disease, selected from HIV infection and HCV infection.

In some aspects, the present disclosure also provides use of the anti-Tim-3 antibody molecules in manufacturing medicine for treating various disorders or diseases described herein.

The anti-Tim-3 antibody molecules described herein show a special set of effector functions and physicochemical properties, which can inhibit Tim-3-mediated cellular signaling in immune cells, re-activate immune cells and enhance immunity. And, the mAbs in the format of full-length human IgG1 with modified heavy chain constant region have a unique set of features in the aspects of effector functions. The anti-Tim-3 mAbs were also humanized with high degree of similarity to human antibody molecules. In addition, the anti-Tim-3 antibody can synergize with an anti-PD-1 antibody, to activate T cells in vitro, to reduce tumor growth. Thereby, the anti-Tim-3 antibodies disclosed here may have therapeutic utility in treatment of cancer, viral infections and other human diseases that are mechanistically associated with immune tolerance or "exhaustion".

BRIEF DESCRIPTION OF THE DRAWINGS

FIG. 2A shows the phylogenetic tree of anti-Tim-3 antibody heavy chain variable (Vh) regions; FIG. 2B shows the phylogenetic tree of anti-Tim-3 antibody light chain variable (Vl) regions. A total of 23 Tim-3 Vh and 20 Vκ sequences were aligned using DNASTAR's Megalign software. Sequence homology was displayed in the phylogenetic trees.

DETAIL DESCRIPTION OF THE INVENTION

Definitions

Exemplary Conservative Amino Acid Substitutions

Figure 1:
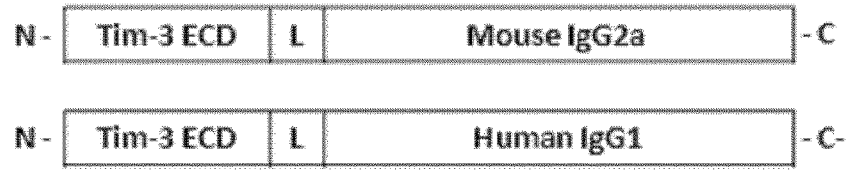
FIG. 1 shows schematic diagrams of Tim-3-mIgG2a (top) and Tim-3-huIgG1 (bottom), in which L is a linker, N is N-terminus and C is C-terminus.

| Original amino acid residue | One-letter and three-letter codes | Conservative substitution |
|---|---|---|
| Alanine | A or Ala | Gly; Ser |
| Arginine | R or Arg | Lys; His |
| Asparagine | N or Asn | Gln; His |
| Aspartic acid | D or Asp | Gln; Asn |
| Cysteine | C or Cys | Ser; Ala |
| Glutamine | Q or Gln | Asn |
| Glutamic acid | E or Glu | Asp; Gln |
| Glycine | G or Gly | Ala |
| Histidine | H or His | Asn; Gln |
| Isoleucine | I or Ile | Leu; Val |
| Leucine | L or Leu | Ile; val |
| Lysine | K or Lys | Arg; His |
| Methionine | M or Met | Leu; Ile; Tyr |
| Phenylalanine | F or Phe | Tyr; Met; Leu |
| Proline | P or Pro | Ala |
| Serine | S or Ser | Thr |
| Threonine | T or Thr | Ser |
| Tryptophan | W or Trp | Tyr; Phe |
| Tyrosine | Y or Tyr | Trp; Phe |
| Valine | V or Val | Ile; Leu |

Unless specifically defined elsewhere in this document, all other technical and scientific terms used herein have the meaning commonly understood by one of ordinary skill in the art to which this invention belongs.

As used herein, including the appended claims, the singular forms of words such as "a", "an", and "the", include their corresponding plural references unless the context clearly dictates otherwise.

The term "or" is used to mean, and is used interchangeably with, the term "and/or" unless the context clearly dictates otherwise.

Throughout this specification and the claims which follow, unless the context requires otherwise, the word "comprise", and variations such as "comprises" and "comprising", will be understood to imply the inclusion of a stated amino acid sequence, DNA sequence, step or group thereof, but not the exclusion of any other amino acid sequence, DNA sequence, step. When used herein the term "comprising" can be substituted with the term "containing", "including" or sometimes "having".

The term "Tim-3" includes various mammalian isoforms, e.g., human Tim-3, species homologs of human Tim-3, and analogs comprising at least one epitope within Tim-3. And the amino acid sequence of Tim-3, e.g., human Tim-3, and the nucleotide sequence encoding the same, is known in the art.

The terms "administration", "administering", "treating" and "treatment" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" and "treatment" also means in vitro and ex vivo treatments, e.g., of a cell, by a reagent, diagnostic, binding compound, or by another cell. The term "subject" herein includes any organism, preferably an animal, more preferably a mammal (e.g., rat, mouse, dog, cat, rabbit) and most preferably a human.

Antibody or Antibody Molecule

Disclosed herein are antibody molecules that bind to Tim-3 with high affinity and specificity.

In some embodiments, the anti-Tim-3 antibody includes at least one, two, three, four, five or six complementarity determining regions (CDR's) comprising an amino acid sequence SEQ ID NOs 3-8, or 26-27 or variants thereof comprising one or more conservative substitutions.

In some embodiments, the anti-Tim-3 antibody includes at least one, two or three CDRs from a heavy chain variable region (VH) comprising an amino acid sequence of SEQ ID NOs 3-5 or 26 or variants thereof comprising one or more conservative substitutions. In some embodiments, the anti-Tim-3 antibody includes at least one, two or three CDRs from a light chain variable region (VL) comprising an amino acid sequence of SEQ ID NOs 6-8 or 27 or variants thereof comprising one or more conservative substitutions.

In some embodiments, the anti-Tim-3 antibody includes at least one, two, three, four, five or six CDRs from a heavy and light chain variable region comprising an amino acid sequence of SEQ ID NOs 3-8, or 26-27 or variants thereof comprising one or more conservative substitutions.

In some embodiments, the anti-Tim-3 antibody includes six CDRs from a heavy and light chain variable region comprising an amino acid sequence of SEQ ID NOs 3-8, or 26-27 or variants thereof comprising one or more conservative substitutions.

In some embodiments, the anti-Tim-3 antibody comprises:
(a) a heavy chain variable region (VH) comprising one, two or three CDR amino acid sequences selected form SEQ ID NOs 3, 4, 5, or 26 or variants thereof comprising one or more conservative substitutions; and/or
(b) a light chain variable region (VL) comprising one, two or three CDR amino acid sequences selected form SEQ ID NOs 6, 7, 8, or 27 or variants thereof comprising one or more conservative substitutions.

In some embodiments, the anti-Tim-3 antibody comprises:
(a) a heavy chain variable region (VH) comprising a VH-CDR1 amino acid sequence of SEQ ID NO 3 or variants thereof comprising one or more conservative substitutions, a VH-CDR2 amino acid sequence of SEQ ID NO 4 or variants thereof comprising one or more conservative substitutions and a VH-CDR3 amino acid sequence of SEQ ID NO 5 or variants thereof comprising one or more conservative substitutions; and a light chain variable region (VL) comprising a VL-CDR1 amino acid sequence of SEQ ID NO 6 or variants thereof comprising one or more conservative substitutions, a VL-CDR2 amino acid sequence of SEQ ID NO 7 or variants thereof comprising one or more conservative substitutions and a VL-CDR3 amino acid sequence of SEQ ID NO 8 or variants thereof comprising one or more conservative substitutions;
(b) a heavy chain variable region (VH) comprising a VH-CDR1 amino acid sequence of SEQ ID NO 3 or variants thereof comprising one or more conservative substitutions, a VH-CDR2 amino acid sequence SEQ ID NO 26 or variants thereof comprising one or more conservative substitutions and a VH-CDR3 amino acid sequence of SEQ ID NO 5 or variants thereof comprising one or more conservative substitutions; and a light chain variable region (VL) comprising a VL-CDR1 amino acid sequence of SEQ ID NO 6 or variants thereof comprising one or more conservative substitutions, a VL-CDR2 amino acid sequence of SEQ ID NO 7 or variants thereof comprising one or more conservative substitutions and a VL-CDR3 amino acid sequence of SEQ ID NO 8 or variants thereof comprising one or more conservative substitutions;
(c) a heavy chain variable region (VH) comprising a VH-CDR1 amino acid sequence of SEQ ID NO 3 or variants thereof comprising one or more conservative substitutions, a VH-CDR2 amino acid sequence of SEQ ID NO 4 or variants thereof comprising one or more conservative substitutions and a VH-CDR3 amino acid sequence of SEQ ID NO 5 or variants thereof comprising one or more conservative substitutions; and a light chain variable region (VL) comprising a VL-CDR1 amino acid sequence of SEQ ID NO 6 or variants thereof comprising one or more conservative substitutions, a VL-CDR2 amino acid sequence of SEQ ID NO 7 or variants thereof comprising one or more conservative substitutions and a VL-CDR3 amino acid sequence of SEQ ID NO 27 or variants thereof comprising one or more conservative substitutions; or
(d) a heavy chain variable region (VH) comprising a VH-CDR1 amino acid sequence of SEQ ID NO 3 or variants thereof comprising one or more conservative substitutions, a VH-CDR2 amino acid sequence of SEQ ID NO 26 or variants thereof comprising one or more conservative substitutions and a VH-CDR3 amino sequence of SEQ ID NO 5 or variants thereof comprising one or more conservative substitutions; and a light chain variable region (VL) comprising a VL-CDR1 amino acid sequence of SEQ ID NO 6 or variants thereof comprising one or more conservative substitutions, a VL-CDR2 amino acid sequence of SEQ ID NO 7 or variants thereof comprising one or more conservative substitutions and a VL-CDR3 amino acid sequence of SEQ ID NO 27 or variants thereof comprising one or more conservative substitutions.

In some embodiments, the anti-Tim-3 antibody comprises:
(a) a heavy chain variable region (VH) comprising a VH-CDR1 amino acid sequence of SEQ ID NO 3, a VH-CDR2 amino acid sequence of SEQ ID NO 4 and a VH-CDR3 amino acid sequence of SEQ ID NO 5; and a light chain variable region (VL) comprising a VL-CDR1 amino acid sequence of SEQ ID NO 6, a VL-CDR2 amino acid sequence of SEQ ID NO 7 and a VL-CDR3 amino acid sequence of SEQ ID NO 8; or
(b) a heavy chain variable region (VH) comprising a VH-CDR1 amino acid sequence of SEQ ID NO 3, a VH-CDR2 amino acid sequence of SEQ ID NO 26 and a VH-CDR3 amino acid sequence of SEQ ID NO 5; and a light chain variable region (VL) comprising a VL-CDR1 amino acid sequence of SEQ ID NO 6, a VL-CDR2 amino acid sequence of SEQ ID NO 7 and a VL-CDR3 amino acid sequence of SEQ ID NO 27.

In some embodiments, the anti-Tim-3 antibody is a humanized antibody molecule.

In some embodiments, the anti-Tim-3 antibody is a humanized monoclonal antibody (mAb).

In some embodiments, the antibody comprises a heavy chain variable domain having at least 95%, 96%, 97%, 98%, 99% or 100% sequence identity with the amino acid sequence of SEQ ID NOs 9, 17, 28 or 40. In some embodiments, the antibody comprises a heavy chain variable domain having at least 95%, 96%, 97%, 98%, 99% or 100% sequence identity with the amino acid sequence of SEQ ID NOs 9, 17 or 28. In some embodiments, the anti-Tim-3 antibody comprises a light chain variable domain having at least 95%, 96%, 97%, 98%, 99% or 100% sequence identity with the amino acid sequence of SEQ ID NOs 11, 19, 30 or 36.

In some embodiments, the anti-Tim-3 antibody comprises:
(a) a heavy chain variable domain having at least 95%, 96%, 97%, 98%, 99% or 100% sequence identity with the amino acid sequence of SEQ ID NO 9, and a light chain variable domain having at least 95%, 96%, 97%, 98%, 99% or 100% sequence identity with the amino acid sequence of SEQ ID NO 11;
(b) a heavy chain variable domain having at least 95%, 96%, 97%, 98%, 99% or 100% sequence identity with the amino acid sequence of SEQ ID NO 9, and a light chain variable domain having at least 95%, 96%, 97%, 98%, 99% or 100% sequence identity with the amino acid sequence of SEQ ID NO 19;
(c) a heavy chain variable domain having at least 95%, 96%, 97%, 98%, 99% or 100% sequence identity with the amino acid sequence of SEQ ID NO 9, and a light chain variable domain having at least 95%, 96%, 97%, 98%, 99% or 100% sequence identity with the amino acid sequence of SEQ ID NO 30;
(d) a heavy chain variable domain having at least 95%, 96%, 97%, 98%, 99% or 100% sequence identity with the amino acid sequence of SEQ ID NO 9, and a light chain variable domain having at least 95%, 96%, 97%, 98%, 99% or 100% sequence identity with the amino acid sequence of SEQ ID NO 36;
(e) a heavy chain variable domain having at least 95%, 96%, 97%, 98%, 99% or 100% sequence identity with the amino acid sequence of SEQ ID NO 17, and a light chain variable domain having at least 95%, 96%, 97%, 98%, 99% or 100% sequence identity with the amino acid sequence of SEQ ID NO 11;
(f) a heavy chain variable domain having at least 95%, 96%, 97%, 98%, 99% or 100% sequence identity with the amino acid sequence of SEQ ID NO 17, and a light chain variable domain having at least 95%, 96%, 97%, 98%, 99% or 100% sequence identity with the amino acid sequence of SEQ ID NO 19;
(g) a heavy chain variable domain having at least 95%, 96%, 97%, 98%, 99% or 100% sequence identity with the amino acid sequence of SEQ ID NO 17, and a light chain variable domain having at least 95%, 96%, 97%, 98%, 99% or 100% sequence identity with the amino acid sequence of SEQ ID NO 30;
(h) a heavy chain variable domain having at least 95%, 96%, 97%, 98%, 99% or 100% sequence identity with the amino acid sequence of SEQ ID NO 17, and a light chain variable domain having at least 95%, 96%, 97%, 98%, 99% or 100% sequence identity with the amino acid sequence of SEQ ID NO 36;
(i) a heavy chain variable domain having at least 95%, 96%, 97%, 98%, 99% or 100% sequence identity with the amino acid sequence of SEQ ID NO 28, and a light chain variable domain having at least 95%, 96%, 97%, 98%, 99% or 100% sequence identity with the amino acid sequence of SEQ ID NO 11;
(j) a heavy chain variable domain having at least 95%, 96%, 97%, 98%, 99% or 100% sequence identity with the amino acid sequence of SEQ ID NO 28, and a light chain variable domain having at least 95%, 96%, 97%, 98%, 99% or 100% sequence identity with the amino acid sequence of SEQ ID NO 19;
(k) a heavy chain variable domain having at least 95%, 96%, 97%, 98%, 99% or 100% sequence identity with the amino acid sequence of SEQ ID NO 28, and a light chain variable domain having at least 95%, 96%, 97%, 98%, 99% or 100% sequence identity with the amino acid sequence of SEQ ID NO 30;
(m) a heavy chain variable domain having at least 95%, 96%, 97%, 98%, 99% or 100% sequence identity with the amino acid sequence of SEQ ID NO 28, and a light chain variable domain having at least 95%, 96%, 97%, 98%, 99% or 100% sequence identity with the amino acid sequence of SEQ ID NO 36; a heavy chain variable domain having at least 95%, 96%, 97%, 98%, 99% or 100% sequence identity with the amino acid sequence of SEQ ID NO 40, and a light chain variable domain having at least 95%, 96%, 97%, 98%, 99% or 100% sequence identity with the amino acid sequence of SEQ ID NO 11;
(n) a heavy chain variable domain having at least 95%, 96%, 97%, 98%, 99% or 100% sequence identity with the amino acid sequence of SEQ ID NO 40, and a light chain variable domain having at least 95%, 96%, 97%, 98%, 99% or 100% sequence identity with the amino acid sequence of SEQ ID NO 19;
(o) a heavy chain variable domain having at least 95%, 96%, 97%, 98%, 99% or 100% sequence identity with the amino acid sequence of SEQ ID NO 40, and a light chain variable domain having at least 95%, 96%, 97%, 98%, 99% or 100% sequence identity with the amino acid sequence of SEQ ID NO 30; or
(q) a heavy chain variable domain having at least 95%, 96%, 97%, 98%, 99% or 100% sequence identity with the amino acid sequence of SEQ ID NO 40, and a light chain variable domain having at least 95%, 96%, 97%, 98%, 99% or 100% sequence identity with the amino acid sequence of SEQ ID NO 36.

In some embodiments, the anti-Tim-3 antibody comprises:
(a) a heavy chain variable domain having at least 95%, 96%, 97%, 98%, 99% or 100% sequence identity with the amino acid sequence of SEQ ID NO 9, and a light chain variable domain having at least 95%, 96%, 97%, 98%, 99% or 100% sequence identity with the amino acid sequence of SEQ ID NO 11;
(b) a heavy chain variable domain having at least 95%, 96%, 97%, 98%, 99% or 100% sequence identity with the amino acid sequence of SEQ ID NO 9, and a light chain variable domain having at least 95%, 96%, 97%, 98%, 99% or 100% sequence identity with the amino acid sequence of SEQ ID NO 19;
(c) a heavy chain variable domain having at least 95%, 96%, 97%, 98%, 99% or 100% sequence identity with the amino acid sequence of SEQ ID NO 9, and a light chain variable domain having at least 95%, 96%, 97%, 98%, 99% or 100% sequence identity with the amino acid sequence of SEQ ID NO 30;
(d) a heavy chain variable domain having at least 95%, 96%, 97%, 98%, 99% or 100% sequence identity with the amino acid sequence of SEQ ID NO 9, and a light chain variable domain having at least 95%, 96%, 97%, 98%, 99% or 100% sequence identity with the amino acid sequence of SEQ ID NO 36;
(e) a heavy chain variable domain having at least 95%, 96%, 97%, 98%, 99% or 100% sequence identity with the amino acid sequence of SEQ ID NO 17, and a light chain variable domain having at least 95%, 96%, 97%, 98%, 99% or 100% sequence identity with the amino acid sequence of SEQ ID NO 11;
(f) a heavy chain variable domain having at least 95%, 96%, 97%, 98%, 99% or 100% sequence identity with the amino acid sequence of SEQ ID NO 17, and a light chain variable domain having at least 95%, 96%, 97%, 98%, 99% or 100% sequence identity with the amino acid sequence of SEQ ID NO 19;
(g) a heavy chain variable domain having at least 95%, 96%, 97%, 98%, 99% or 100% sequence identity with the amino acid sequence of SEQ ID NO 17, and a light chain variable domain having at least 95%, 96%, 97%, 98%, 99% or 100% sequence identity with the amino acid sequence of SEQ ID NO 30;
(h) a heavy chain variable domain having at least 95%, 96%, 97%, 98%, 99% or 100% sequence identity with the amino acid sequence of SEQ ID NO 17, and a light chain variable domain having at least 95%, 96%, 97%, 98%, 99% or 100% sequence identity with the amino acid sequence of SEQ ID NO 36;
(i) a heavy chain variable domain having at least 95%, 96%, 97%, 98%, 99% or 100% sequence identity with the amino acid sequence of SEQ ID NO 28, and a light chain variable domain having at least 95%, 96%, 97%, 98%, 99% or 100% sequence identity with the amino acid sequence of SEQ ID NO 11;
(j) a heavy chain variable domain having at least 95%, 96%, 97%, 98%, 99% or 100% sequence identity with the amino acid sequence of SEQ ID NO 28, and a light chain variable domain having at least 95%, 96%, 97%, 98%, 99% or 100% sequence identity with the amino acid sequence of SEQ ID NO 19;
(k) a heavy chain variable domain having at least 95%, 96%, 97%, 98%, 99% or 100% sequence identity with the amino acid sequence of SEQ ID NO 28, and a light chain variable domain having at least 95%, 96%, 97%, 98%, 99% or 100% sequence identity with the amino acid sequence of SEQ ID NO 30; or;
(l) a heavy chain variable domain having at least 95%, 96%, 97%, 98%, 99% or 100% sequence identity with the amino acid sequence of SEQ ID NO 28, and a light chain variable domain having at least 95%, 96%, 97%, 98%, 99% or 100% sequence identity with the amino acid sequence of SEQ ID NO 36.

In some embodiments, the anti-Tim-3 antibody comprises:
(a) a heavy chain variable domain comprising the amino acid sequence of SEQ ID NO 9, and a light chain variable domain comprising the amino acid sequence of SEQ ID NO 11;
(b) a heavy chain variable domain comprising the amino acid sequence of SEQ ID NO 17, and a light chain variable domain comprising the amino acid sequence of SEQ ID NO 19;
(c) a heavy chain variable domain comprising the amino acid sequence of SEQ ID NO 28, and a light chain variable domain comprising the amino acid sequence of SEQ ID NO 30;
(d) a heavy chain variable domain comprising the amino acid sequence of SEQ ID NO 28, and a light chain variable domain comprising the amino acid sequence of SEQ ID NO 36; or
(e) a heavy chain variable domain comprising the amino acid sequence of SEQ ID NO 40, and a light chain variable domain comprising the amino acid sequence of SEQ ID NO 36.

In some embodiments, the anti-Tim-3 antibody comprises:
(a) a heavy chain variable domain comprising the amino acid sequence of SEQ ID NO 9, and a light chain variable domain comprising the amino acid sequence of SEQ ID NO 11;
(b) a heavy chain variable domain comprising the amino acid sequence of SEQ ID NO 17, and a light chain variable domain comprising the amino acid sequence of SEQ ID NO 19;
(c) a heavy chain variable domain comprising the amino acid sequence of SEQ ID NO 28, and a light chain variable domain comprising the amino acid sequence of SEQ ID NO 30; or
(d) a heavy chain variable domain comprising the amino acid sequence of SEQ ID NO 28, and a light chain variable domain comprising the amino acid sequence of SEQ ID NO 36.

In some embodiments, the anti-Tim-3 antibody comprises a heavy chain having at least 95%, 96%, 97%, 98%, 99% or 100% sequence identity with the amino acid sequence of SEQ ID NO 13, 22 or 32. In some embodiments, the anti-Tim-3 antibody comprises a light chain having at least 95%, 96%, 97%, 98%, 99% or 100% sequence identity with the amino acid sequence of SEQ ID NO 15, 24, 34 or 38.

In some embodiments, the anti-Tim-3 antibody comprises:
(a) a heavy chain having at least 95%, 96%, 97%, 98%, 99% or 100% sequence identity with the amino acid sequence of SEQ ID NO 13, and a light chain having at least 95%, 96%, 97%, 98%, 99% or 100% sequence identity with the amino acid sequence of SEQ ID NO 15;
(b) a heavy chain having at least 95%, 96%, 97%, 98%, 99% or 100% sequence identity with the amino acid sequence of SEQ ID NO 13, and a light chain having at least 95%, 96%, 97%, 98%, 99% or 100% sequence identity with the amino acid sequence of SEQ ID NO 24;
(c) a heavy chain having at least 95%, 96%, 97%, 98%, 99% or 100% sequence identity with the amino acid sequence of SEQ ID NO 13, and a light chain having at least 95%, 96%, 97%, 98%, 99% or 100% sequence identity with the amino acid sequence of SEQ ID NO 34;
(d) a heavy chain having at least 95%, 96%, 97%, 98%, 99% or 100% sequence identity with the amino acid sequence of SEQ ID NO 13, and a light chain having at least 95%, 96%, 97%, 98%, 99% or 100% sequence identity with the amino acid sequence of SEQ ID NO 38;
(e) a heavy chain having at least 95%, 96%, 97%, 98%, 99% or 100% sequence identity with the amino acid sequence of SEQ ID NO 22, and a light chain having at least 95%, 96%, 97%, 98%, 99% or 100% sequence identity with the amino acid sequence of SEQ ID NO 15;
(f) a heavy chain having at least 95%, 96%, 97%, 98%, 99% or 100% sequence identity with the amino acid sequence of SEQ ID NO 22, and a light chain having at least 95%, 96%, 97%, 98%, 99% or 100% sequence identity with the amino acid sequence of SEQ ID NO 24;
(g) a heavy chain having at least 95%, 96%, 97%, 98%, 99% or 100% sequence identity with the amino acid sequence of SEQ ID NO 22, and a light chain having at least 95%, 96%, 97%, 98%, 99% or 100% sequence identity with the amino acid sequence of SEQ ID NO 34;
(h) a heavy chain having at least 95%, 96%, 97%, 98%, 99% or 100% sequence identity with the amino acid sequence of SEQ ID NO 22, and a light chain having at least 95%, 96%, 97%, 98%, 99% or 100% sequence identity with the amino acid sequence of SEQ ID NO 38;
(i) a heavy chain having at least 95%, 96%, 97%, 98%, 99% or 100% sequence identity with the amino acid sequence of SEQ ID NO 32, and a light chain having at least 95%, 96%, 97%, 98%, 99% or 100% sequence identity with the amino acid sequence of SEQ ID NO 15;

(j) a heavy chain having at least 95%, 96%, 97%, 98%, 99% or 100% sequence identity with the amino acid sequence of SEQ ID NO 32, and a light chain having at least 95%, 96%, 97%, 98%, 99% or 100% sequence identity with the amino acid sequence of SEQ ID NO 24;
(k) a heavy chain having at least 95%, 96%, 97%, 98%, 99% or 100% sequence identity with the amino acid sequence of SEQ ID NO 32, and a light chain having at least 95%, 96%, 97%, 98%, 99% or 100% sequence identity with the amino acid sequence of SEQ ID NO 34; or
(l) a heavy chain having at least 95%, 96%, 97%, 98%, 99% or 100% sequence identity with the amino acid sequence of SEQ ID NO 32, and a light chain having at least 95%, 96%, 97%, 98%, 99% or 100% sequence identity with the amino acid sequence of SEQ ID NO 38.

In some embodiments, the anti-Tim-3 antibody comprises:
(a) a heavy chain comprising the amino acid sequence of SEQ ID NO 13, and a light chain comprising the amino acid sequence of SEQ ID NO 15;
(b) a heavy chain comprising the amino acid sequence of SEQ ID NO 22, and a light chain comprising the amino acid sequence of SEQ ID NO 24;
(c) a heavy chain comprising the amino acid sequence of SEQ ID NO 32, and a light chain comprising the amino acid sequence of SEQ ID NO 34; or
(d) a heavy chain comprising the amino acid sequence of SEQ ID NO 32, and a light chain comprising the amino acid sequence of SEQ ID NO 38.

In some embodiments, the anti-Tim-3 antibody comprises one or more of:
(a) a light chain with an Aspartic acid to Glutamic acid mutation at position 1 of SEQ ID NO 24;
(b) a light chain with a Leucine to Methionine mutation at position 4 of SEQ ID NO 24;
(c) a light chain with a Valine to Isoleucine mutation at position 62 of SEQ ID NO 24;
(d) a light chain with a Aspartic acid to Glutamic acid mutation at position 74 of SEQ ID NO 24;
(e) a light chain with a Methionine to Leucine mutation at position 96 of SEQ ID NO 24;
(f) a heavy chain with a Phenylalanine to Tyrosine mutation at position 59 of SEQ ID NO 22;
(g) a heavy chain with a Proline to Valine mutation at position 60 of SEQ ID NO 22;
(h) a heavy chain with a Serine to Threonine mutation at position 77 of SEQ ID NO 22; or
(i) a heavy chain with a Cysteine to Leucine mutation at position 78 of SEQ ID NO 22.

In some embodiments, the anti-Tim-3 antibody is a Fab, F(ab')2, Fv, or a single chain Fv (ScFv).

In some embodiments, the anti-Tim-3 antibody comprises a heavy chain constant region of the subclass of IgG1, IgG2, IgG3, IgG4 or a variant thereof, and a light chain constant region of the type of kappa or lambda or a variant thereof.

In some embodiments, the anti-Tim-3 antibody comprises a variant heavy chain constant region of the subclass of IgG1, IgG2, IgG3, or IgG4, wherein the variant heavy chain constant region provides a reduced or eliminated effector function such as antibody-dependent cell-mediated cytotoxicity (ADCC) or complement-dependent cytotoxicity (CDC).

In some embodiments, the anti-Tim-3 antibody comprises a heavy chain constant region of human IgG1 or a variant thereof. In more preferred embodiments, the anti-Tim-3 antibody comprises a variant heavy chain constant region of human IgG1 comprising one or more mutations selected from a group consisting of $E_{233}P$, $L_{234}A$, $L_{235}A$, $L_{236}\Delta$ and $P_{329}A$. In some embodiments, the anti-Tim-3 antibody comprises a variant human IgG1 heavy chain constant region comprising the amino acid sequence of SEQ ID NO 21, and a human kappa light chain constant region.

In some embodiments, the anti-Tim-3 antibody is isolated or recombinant.

In some embodiments, the anti-Tim-3 antibody comprises at least one antigen-binding site, or at least a variable region.

In some embodiments, the anti-Tim-3 antibody comprises an antigen-binding fragment from an antibody described herein.

The term "antibody" herein is used in the broadest sense and specifically covers antibodies (including full length monoclonal antibodies) and antibody fragments so long as they recognize antigen, e.g., Tim-3, PD-1. An antibody is usually monospecific, but may also be described as idiospecific, heterospecific, or polyspecific. Antibody molecules bind by means of specific binding sites to specific antigenic determinants or epitopes on antigens.

The term "monoclonal antibody" or "mAb" or "Mab" herein means a population of substantially homogeneous antibodies, i.e., the antibody molecules comprised in the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their complementarity determining regions (CDRs), which are often specific for different epitopes. The modifier "monoclonal" indicates the character of the antibody as being obtained from a substantially homogeneous population of antibodies, and is not to be construed as requiring production of the antibody by any particular method. Monoclonal antibodies (mAbs) may be obtained by methods known to those skilled in the art. See, for example Kohler G et al., *Nature* 1975 256:495-497; U.S. Pat. No. 4,376,110; Ausubel F M et al., CURRENT PROTOCOLS IN MOLECULAR BIOLOGY 1992; Harlow E et al., ANTIBODIES: A LABORATORY MANUAL, Cold spring Harbor Laboratory 1988; and Colligan J E et al., CURRENT PROTOCOLS IN IMMUNOLOGY 1993. The mAbs disclosed herein may be of any immunoglobulin class including IgG, IgM, IgD, IgE, IgA, and any subclass thereof. A hybridoma producing a mAb may be cultivated in vitro or in vivo. High titers of mAbs can be obtained in in vivo production where cells from the individual hybridomas are injected intraperitoneally into mice, such as pristine-primed Balb/c mice to produce ascites fluid containing high concentrations of the desired mAbs. MAbs of isotype IgM or IgG may be purified from such ascites fluids, or from culture supernatants, using column chromatography methods well known to those of skill in the art.

In general, the basic antibody structural unit comprises a tetramer. Each tetramer includes two identical pairs of polypeptide chains, each pair having one "light chain" (about 25 kDa) and one "heavy chain" (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as α, δ, ε, γ, or μ, and define the antibody's isotypes as IgA, IgD, IgE, IgG, and IgM, respectively. Within light and heavy chains, the variable and constant regions are joined by a "J" region of about 12 or more amino acids, with the heavy chain also including a "D" region of about 10 more amino acids.

The variable regions of each light/heavy chain (VL/VH) pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called "complementarity determining regions (CDRs)", which are located between relatively conserved framework regions (FR). The CDRs are usually aligned by the framework regions, enabling binding to a specific epitope. In general, from N-terminal to C-terminal, both light and heavy chain variable domains comprise FR-1 (or FR1), CDR-1 (or CDR1), FR-2 (FR2), CDR-2 (CDR2), FR-3 (or FR3), CDR-3 (CDR3), and FR-4 (or FR4). The assignment of amino acids to each domain is, generally, in accordance with the definitions of Sequences of Proteins of Immunological Interest, Kabat, et al., *National Institutes of Health*, Bethesda, Md.; 5<m>ed.; NIH Publ. No. 91-3242 (1991); Kabat (1978) *Adv. Prot. Chem.* 32: 1-75; Kabat, et al., (1977) *J. Biol. Chem.* 252:6609-6616; Chothia, et al, (1987) *J Mol. Biol.* 196:901-917 or Chothia, et al, (1989) *Nature* 342:878-883.

The term "hypervariable region" means the amino acid residues of an antibody that are responsible for antigen-binding. The hypervariable region comprises amino acid residues from a "CDR" (i.e., VL-CDR1, VL-CDR2 and VL-CDR3 in the light chain variable domain and VH-CDR1, VH-CDR2 and VH-CDR3 in the heavy chain variable domain). See, Kabat et al. (1991) *Sequences of Proteins of Immunological Interest,* 5th Ed. *Public Health Service, National Institutes of Health*, Bethesda, Md. (defining the CDR regions of an antibody by sequence); see also Chothia and Lesk (1987) *J. Mol. Biol.* 196: 901-917 (defining the CDR regions of an antibody by structure). The term "framework" or "FR" residues means those variable domain residues other than the hypervariable region residues defined herein as CDR residues.

Unless otherwise indicated, "antibody fragment" or "antigen-binding fragment" means antigen binding fragments of antibodies, i.e. antibody fragments that retain the ability to bind specifically to the antigen bound by the full-length antibody, e.g. fragments that retain one or more CDR regions. Examples of antigen binding fragments include, but not limited to, Fab, Fab', F(ab')2, and Fv fragments; diabodies; linear antibodies; single-chain antibody molecules, e.g., single chain Fv (ScFv); nanobodies and multispecific antibodies formed from antibody fragments.

An antibody that binds to a specified target protein with specificity is also described as specifically binding to a specified target protein. This means the antibody exhibits preferential binding to that target as compared to other proteins, but this specificity does not require absolute binding specificity. An antibody is considered "specific" for its intended target if its binding is determinative of the presence of the target protein in a sample, e.g. without producing undesired results such as false positives. Antibodies or binding fragments thereof, useful in the present invention will bind to the target protein with an affinity that is at least two fold greater, preferably at least 10-times greater, more preferably at least 20-times greater, and most preferably at least 100-times greater than the affinity with non-target proteins. An antibody herein is said to bind specifically to a polypeptide comprising a given amino acid sequence, e.g. the amino acid sequence of a mature human Tim-3 molecule, if it binds to polypeptides comprising that sequence but does not bind to proteins lacking that sequence.

The term "human antibody" herein means an antibody that comprises human immunoglobulin protein sequences only. A human antibody may contain murine carbohydrate chains if produced in a mouse, in a mouse cell, or in a hybridoma derived from a mouse cell. Similarly, "mouse antibody" or "rat antibody" mean an antibody that comprises only mouse or rat immunoglobulin protein sequences, respectively.

The term "humanized antibody" means forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum", "hu", "flu" or "h" is added to antibody clone designations when necessary to distinguish humanized antibodies from parental rodent antibodies. The humanized forms of rodent antibodies will generally comprise the same CDR sequences of the parental rodent antibodies, although certain amino acid substitutions may be included to increase affinity, increase stability of the humanized antibody, or for other reasons.

The terms "cancer" or "tumor" herein mean or describe the physiological condition in mammals that is typically characterized by unregulated cell growth. Examples of cancer include but are not limited to, a lung cancer (including small-cell lung cancer, or non-small cell lung cancer), an adrenal cancer, a liver cancer, a stomach cancer, a cervical cancer, a melanoma, a renal cancer, a breast cancer, a colorectal cancer, a leukemia, a bladder cancer, a bone cancer, a brain cancer, an endometrial cancer, a head and neck cancer, a lymphoma, an ovarian cancer, a skin cancer, a thyroid tumor, or a metastatic lesion of the cancer.

The term "CDRs" means complementarity determining region(s) in an immunoglobulin variable region, defined using the Kabat numbering system, unless otherwise indicated.

Pharmaceutical Compositions and Kits

In some aspects, this disclosure provides compositions, e.g., pharmaceutically acceptable compositions, which include an anti-Tim-3 antibody described herein, formulated together with at least one pharmaceutically acceptable excipient. As used herein, the term "pharmaceutically acceptable excipient" includes any and all solvents, dispersion media, isotonic and absorption delaying agents, and the like that are physiologically compatible. The excipient can be suitable for intravenous, intramuscular, subcutaneous, parenteral, rectal, spinal or epidermal administration (e.g. by injection or infusion).

The compositions herein may be in a variety of forms. These include, for example, liquid, semi-solid and solid dosage forms, such as liquid solutions (e.g., injectable and infusion solutions), dispersions or suspensions, liposomes, and suppositories. A suitable form depends on the intended mode of administration and therapeutic application. Typical suitable compositions are in the form of injectable or infusion solutions. One suitable mode of administration is parenteral (e.g., intravenous, subcutaneous, intraperitoneal, intramuscular). In some embodiments, the antibody is administered by intravenous infusion or injection. In certain embodiments, the antibody is administered by intramuscular or subcutaneous injection.

The term "therapeutically effective amount" as herein used, refers to the amount of an antibody that, when administered to a subject for treating a disease, or at least one of the clinical symptoms of a disease or disorder, is sufficient to effect such treatment for the disease, disorder, or symptom. The "therapeutically effective amount" can vary with the antibody, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In the case of combination therapy, the "therapeutically effective amount" refers to the total amount of the combination objects for the effective treatment of a disease, a disorder or a condition.

The "subject" is a mammal, e.g., a primate, preferably a higher primate, e.g., a human (e.g., a patient having, or at risk of having, a disorder described herein).

EXAMPLE

Example 1. Generation of Anti-Tim-3 Monoclonal Antibodies

A number of murine anti-Tim-3 monoclonal antibodies (mAbs) were generated based on conventional hybridoma technology (de StGroth and Sheidegger, 1980, J Immunol Methods 35:1; Mechetner, 2007, Methods Mol Biol 378:1). The mAbs with high binding activity in enzyme-linked immunosorbent assay (ELISA) and fluorescence-activated cell sorting (FACS) assay were selected for further characterization.

Tim-3 Recombinant Proteins for Immunization and Binding Assays

The cDNA coding for the full-length human Tim-3 (SEQ ID NO. 1) was synthesized based on the GenBank sequence (Accession No: AF450242.1). The coding region of extracellular domain (ECD) consisting of amino acid (AA) 1-202 of Tim-3 (SEQ ID NO. 2) was PCR-amplified, and cloned into a pcDNA3.1-based expression vector (Invitrogen, Carlsbad, Calif., USA) with C-terminus fused either to the Fc region of mouse IgG2a (GenBank Accession No: CAC20702) or to the Fc region of human IgG1 heavy chain (UniProtKB/Swiss-Prot Accession No: P01857), which resulted in two recombinant fusion protein expression plasmids, Tim-3-mIgG2a and Tim-3-huIgG1, respectively. The schematic presentation of Tim-3 fusion proteins is shown in FIG. 1. For the recombinant fusion protein production, Tim-3-mIgG2a and Tim-3-huIgG1 plasmids were transiently transfected into a HEK293-based mammalian cell expression system (developed in house) and cultured for 5-7 days in a $CO_2$ incubator equipped with rotating shaker. The supernatant containing the recombinant protein was collected and cleared by centrifugation. Tim-3-mIgG2a and Tim-3-huIgG1 were purified using a Protein G Sepharose Fast Flow column (Cat. No.: 17061805, GE Life Sciences). Both Tim-3-mIgG2a and Tim-3-huIgG1 proteins were dialyzed against phosphate buffered saline (PBS) and stored in −80° C. freezer in small aliquots.

Stable Expression Cell Lines

To establish stable cell lines that express full-length human Tim-3 (huTim-3) or monkey Tim-3 (mkTim-3, the gene is available from ZYAGE, Cat. No.: KD-702), Tim-3 genes were cloned into a retroviral vector pFB-Neo (Cat. No.: 217561, Agilent, USA). Dual-tropic retroviral vectors were generated according to a previous protocol (Zhang T, et al., 2005, Blood 106:1544-51). Vectors containing huTim-3 and mkTim-3 were transduced into HuT78 and NK92MI cells (ATCC, Manassas, Va., USA), respectively, to generate the cell lines, HuT78/huTim-3 and NK92MI/mkTim-3. The high expression cell lines were selected by culture in complete RPMI1640 medium containing 10% FBS with G418 and FACS binding assay.

Immunization, Hybridoma Fusion and Cloning

Eight to twelve week-old Balb/c mice (HFK BIOSCIENCE CO., LTD, Beijing, China) were immunized intraperitoneally (i.p.) with 100 μl of antigen solution containing 10 μg of Tim-3-mIgG2a and a water-soluble adjuvant (Cat. No.: KX0210041, KangBiQuan, Beijing, China). The procedure was repeated three weeks later. Two weeks after the $2^{nd}$ immunization, mouse sera were evaluated for Tim-3 binding by ELISA and FACS. Ten days after serum screening, the mice with highest anti-Tim-3 antibody serum titers were boosted i.p. with 50 μg of Tim-3-mIgG2a. Three days after boosting, the splenocytes were isolated and fused to the murine myeloma cell line, SP2/0 cells (ATCC), using the standard techniques (Colligan J E, et al., CURRENT PROTOCOLS IN IMMUNOLOGY, 1993).

Assessment of Tim-3 Binding Activity of Antibodies by ELISA and FACS

The supernatants of hybridoma clones were initially screened by ELISA as described in Methods in Molecular Biology (2007) 378:33-52 with some modifications. Briefly, Tim-3-huIgG1 protein was coated in 96-well plates. The HRP-linked anti-mouse IgG antibody (Cat. No.: 7076S, Cell Signaling Technology, USA) and substrate (Cat. No.: 00-4201-56, eBioscience, USA) were used for development, and absorbance signal at the wavelength of 450 nm was measured using a plate reader (SpectraMax Paradigm, Molecular Devices, USA). The ELISA-positive clones were further verified by FACS using either HuT78/huTim-3 or NK92mi/mkTim-3 cells described above. Tim-3-expressing cells ($10^5$ cells/well) were incubated with ELISA-positive hybridoma supernatants, followed by binding with Alexa Fluro-647-labeled goat anti-mouse IgG antibody (Cat. No.: A0473, Beyotime Biotechnology, China). Cell fluorescence was quantified using a flow cytometer (Guava easyCyte 8HT, Merck-Millipore, USA).

The conditioned media from the hybridomas that showed positive signals in both ELISA and FACS screening were subjected to functional assays to identify antibodies with good functional activity in human immune cell-based assays (see following sections). The antibodies with desired functional activities were further sub-cloned and characterized.

Subcloning and Adaptation of Hybridomas to Serum Free or Low Serum Medium

After screening primarily by ELISA, FACS and functional assays (described in Examples 7 and 8), the positive hybridoma clones were sub-cloned by limiting dilution. The top antibody subclones verified through functional assays were adapted for growth in the CDM4MAb medium (Cat. No.: SH30801.02, Hyclone, USA) with 3% FBS.

Expression and Purification of Monoclonal Antibodies

Hybridoma cells were cultured in CDM4MAb medium (Cat. No.: SH30801.02, Hyclone), and incubated in a $CO_2$ incubator for 5 to 7 days at 37° C. The conditioned medium was collected through centrifugation and filtrated by passing a 0.22 μm membrane before purification. Murine antibody-containing supernatants were applied and bound to a Protein A column (Cat. No.: 17127901, GE Life Sciences) following the manufacturer's guide. The procedure usually yielded antibodies at purity above 90%. The Protein A-affinity purified antibodies were either dialyzed against PBS or further purified using a HiLoad 16/60 Superdex200 column (Cat. No.: 17531801, GE Life Sciences) to remove aggregates. Protein concentrations were determined by measuring absorbance at 280 nm. The final antibody preparations were stored in aliquots in −80° C. freezer.

Example 2. Cloning and Sequence Analysis of Tim-3 Antibodies

Murine hybridoma cells were harvested to prepare total RNAs using Ultrapure RNA kit (Cat. No.: 74104, QIAGEN, Germany) based on the manufacturer's protocol. The $1^{st}$ strand cDNAs were synthesized using a cDNA synthesis kit from Invitrogen (Cat. No.: 18080-051) and PCR amplification of Vh and Vk genes of murine mAbs was performed using a PCR kit (Cat. No.: CW0686, CWBio, Beijing, China). The oligo primers used for antibody cDNAs cloning of heavy chain variable region (Vh) and kappa light chain variable region (Vk) were synthesized based on the sequences reported previously (Brocks et al., 2001 Mol Med 7:461). PCR products were then subcloned into the pEASY-Blunt cloning vector (Cat. No.: CB101-02, TransGen, China) and sequenced. The amino acid sequences of Vh and Vk regions were deduced from the DNA sequencing results.

Figure 2:
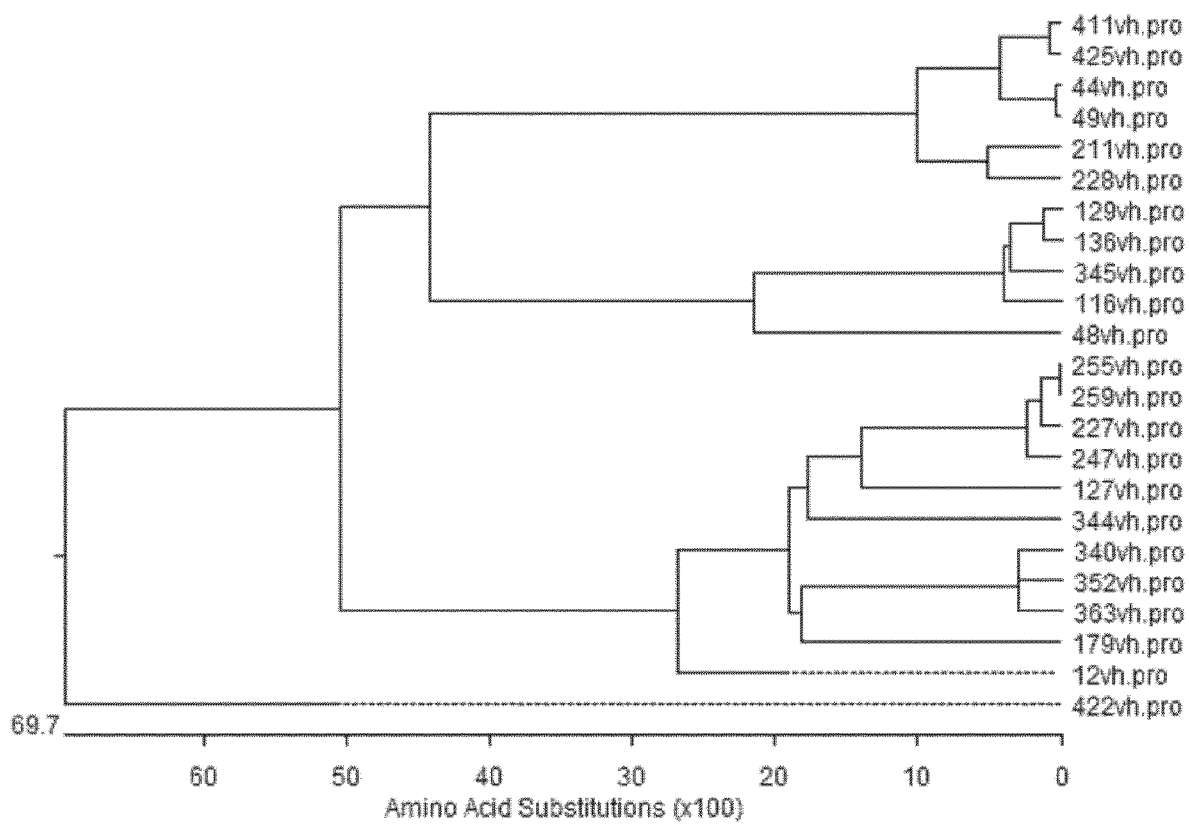
FIGS. 2A-2B show the phylogenetic trees of anti-Tim-3 antibodies.
Figure 2:
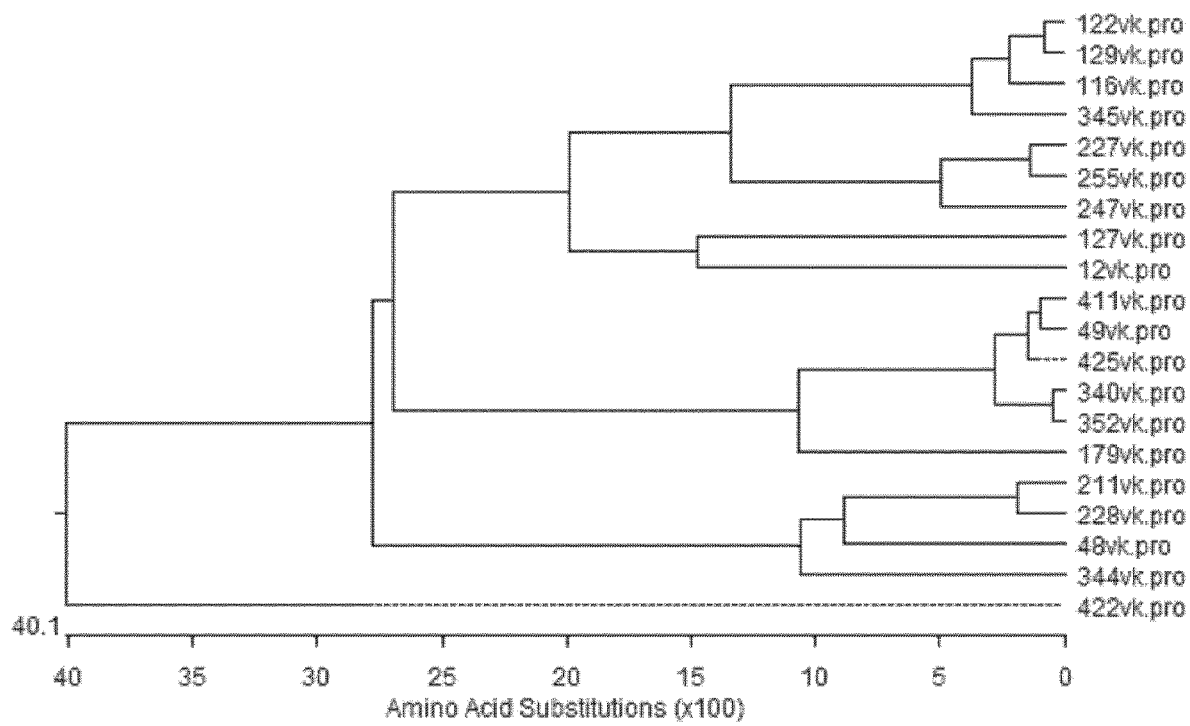

The murine mAbs were analyzed by comparing sequence homology and grouped based on sequence similarity (FIG. 2). Complementary determinant regions (CDRs) were defined based on the Kabat (Wu and Kabat, 1970, *J. Exp. Med.* 132:211-250) and IMGT (Lefranc, 1999, *Nucleic Acids Research* 27:209-212) system by sequence annotation and by internet-based sequence analysis (http://www.imgt.org/IMGT_vquest/share/textes/index.html). The amino acid sequences of a representative top clone mu425 (Vh and Vk) were listed in Table 1 (SEQ ID NOs. 9 and 11). The CDR sequences of mu425 were listed in Table 2 (SEQ ID NOs 3-8).

TABLE 1

| Amino acid sequences of mu425 VH and VK regions | | |
|---|---|---|
| | Sequence | SEQ ID NO |
| mu425 VH | EVKLVESGGGLVKPGGSLKLSCAASGFTFSRYAMSWVRQIPEKRLEW VAAISSGGSLYFPDSVKGRFTISRDNARNICYLQMNSLRSDDTAMYYC ARGREADGGYFDYWGQGTTLTVSS | 9 |
| mu425 VK | DIVLTQSPASLAVSLGQRATISCRASESVEYYGTSLMQWYQQKPGQPP KLLIYAASNVESGVPARFSGSGSGTDFSLNIHPVEEDDIAMYFCQQSM KVPLTFGAGTKLELK | 11 |

TABLE 2

| CDR sequences (amino acids) of mu425 VH and VK regions | | | | | | |
|---|---|---|---|---|---|---|
| | CDR1 | SEQ ID NO | CDR2 | SEQ ID NO | CDR3 | SEQ ID NO |
| mu425, VH | RYAMS | 3 | AISSGGSLYFPDSVKG | 4 | GREADGGYFDY | 5 |
| mu425, VK | RASESVEYYGTSLMQ | 6 | AASNVES | 7 | QQSMKVPLT | 8 |

Example 3. Affinity Determination of Purified Murine Anti-Tim-3 Antibodies by SPR The Tim-3 antibodies with high binding activities in ELISA and FACS, as well as with potent functional activities in the cell-based assays (described in Examples 7 and 8) were characterized for their binding kinetics by SPR assays using BIAcore™ T-200 (GE Life Sciences). Briefly, anti-human IgG antibody was immobilized on an activated CM5 biosensor chip (Cat. No.: BR100530, GE Life Sciences). Human Fc-tagged Tim-3 IgV domain was flowed over the chip surface and captured by anti-human IgG antibody. Then a serial dilution (0.36 nM to 90 nM) of purified murine antibodies were flowed over the chip surface and changes in surface plasmon resonance signals were analyzed to calculate the association rates ($k_{on}$) and dissociation rates ($k_{off}$) by using the one-to-one Langmuir binding model (BIA Evaluation Software, GE Life Sciences). The equilibrium dissociation constant ($K_D$) was calculated as the ratio $k_{off}/k_{on}$. The binding affinity profiles of top mAbs including mu425, mu44, mu 225 and mu411, were shown in Table 3.

TABLE 3

Comparison of hybridoma antibody binding affinities by SPR

| Antibodies | $k_{on}$ (M$^{-1}$s$^{-1}$) | $k_{off}$ (s$^{-1}$) | $K_D$ (nM) |
|---|---|---|---|
| mu425 | $1.59 \times 10^6$ | $9.33 \times 10^{-5}$ | 0.058 |
| mu44 | $1.24 \times 10^6$ | $1.86 \times 10^{-4}$ | 0.150 |
| mu255 | $5.52 \times 10^5$ | $7.84 \times 10^{-4}$ | 1.42 |
| mu411 | $1.44 \times 10^6$ | $3.36 \times 10^{-4}$ | 0.234 |

Example 4. Humanization of the Murine Anti-Human Tim-3 mAb Mu425 mAb Humanization and Engineering

For humanization of mu425, human germline IgG genes were searched for sequences that share high degrees of homology with the cDNA sequences of mu425 variable regions by blasting the human immunoglobulin gene database in IMGT (http://www.imgt.org/IMGT_vquest/share/textes/index.html) and NCBI (http://www.ncbi.nlm.nih.gov/igblast/) websites. The human IGVH and IGVK genes that are present in human antibody repertoires with high frequencies (Glanville, 2009, PNAS 106:20216-20221) and are highly homologous to mu425 were selected as the templates for humanization. Before humanization, mu425 heavy and light chain variable domains were fused to a modified human IgG1 constant region termed as human IgG1mf (SEQ ID NO. 21) and a human kappa constant region, respectively. IgG1mf (SEQ ID NO: 21) is an IgG1 mutant containing a combination of mutations, $E_{233}P$, $L_{234}A$, $L_{235}A$, $L_{236}\Delta$ and $P_{329}A$ (amino acid numbering is based on EU system) as compared to wild-type human IgG1.

Humanization was carried out by CDR-grafting (Methods in Molecular Biology, Vol 248: Antibody Engineering, Methods and Protocols, Humana Press) and the humanized antibodies (hu425s) were engineered in the human IgG1 format. In the initial round of humanization, mutations from murine to human amino acid residues in framework regions were guided by the simulated 3D structure, and the murine framework residues of structural importance for maintaining the canonical structures of CDRs were retained in the 1$^{st}$ version of humanized antibody 425, hu425-1-1 (the amino acid sequences of the heavy chain and light chain are set for in SEQ ID NOs. 22 and 24). Specifically, CDRs of mu425 Vk were grafted into the frameworks of human germline variable gene IGVK3-15 with 4 murine framework residues (D1, L4, V62 and D74) retained (the amino acid sequences of the light chain variable domain is set for in SEQ ID NO. 19). CDRs of mu425 Vh were grafted into the frameworks of human germline variable gene IGVH3-7 with 1 murine framework ($C_{78}$) residue retained (the amino acid sequences of the heavy chain variable domain is set for in SEQ ID NO. 17)

Hu425-1-1 was constructed as human full-length antibody format using in-house developed expression vectors that contain constant regions of a human IgG1 variant termed as IgG1mf (SEQ ID NO. 21) and kappa chain, respectively, with easy adapting subcloning sites. Expression and preparation of hu425-1-1 antibody was achieved by co-transfection of the above two constructs into 293G cells and by purification using a protein A column (Cat. No.: 17543802, GE Life Sciences). The purified antibodies were concentrated to 0.5-5 mg/mL in PBS and stored in aliquots in −80° C. freezer.

Based on hu425-1-1 template, we made a number of single-mutations converting the retained murine residues in framework regions of Vk to corresponding human germline residues, which include D1E, L4M, V62I and D74E in Vk. The resulted hu425-1-2a (D1E), hu425-1-2b (L4M), hu425-1-2c (V62I) and hu425-1-2d (D74E) all had similar binding and functional activities to hu425-1-1. In order to further improve humanization level of the heavy chain, we also changed the retained residue C78 and the C-terminal part of H-CDR2 (Kabat's definition) from murine sequence to corresponding human germline residues. Specifications of the 3 humanized antibodies were hu425-2A-1 (F59Y in Vh), hu425-2B-1 (P60V in Vh) and hu425-2C-1 (C78L in Vh). All humanization mutations were made using primers containing mutations at specific positions and a site directed mutagenesis kit (Cat. No. FM111-02, TransGen, Beijing, China). The desired mutations were verified by sequence analysis. These hu425 variant antibodies were tested in binding and functional assays as described previously. Comparing to hu425-1-1, hu425-2B-1 had significantly reduced binding affinities and functionalities (data not shown) while the rest versions of hu425 humanized variants had similar binding and functional activities to hu425-1-1.

Hu425 antibodies were further engineered by introducing mutations in CDRs and framework regions to improve molecular biochemical and biophysical properties for therapeutic use in human. The considerations include amino acid compositions, heat stability ($T_m$), surface hydrophobicity and isoelectronic points (pIs) while maintaining functional activities.

Taken together, two well-engineered versions of humanized monoclonal antibodies, hu425-2-2 (the amino acid sequences of the heavy chain and light chain variable domains are set for in SEQ ID NOs. 28 and 30) and hu425-2-3b (the amino acid sequences of the heavy chain and light chain variable domains are set for in SEQ ID NOs. 28 and 36), were derived from the mutation process described above, and characterized in details. Both hu425-2-2 and hu425-2-3b comprise a mutation in H-CDR2 (SEQ ID NO: 26) and in L-CDR3 (SEQ ID NO: 27). The amino acid sequences of heavy/light chain variable regions and six CDRs of hu425-2-2 and hu425-2-3b are listed in Table 4 and Table 5 below. The results showed that both hu425-2-3b and hu425-2-2 were very similar in binding affinity and functional activities such as inhibiting the Tim-3 mediated downstream signaling.

TABLE 4

Amino acid sequences of VH and VK regions of hu425-2-2 and hu425-2-3b

| | Sequence | SEQ ID NO |
|---|---|---|
| hu425-2-2 VH | EVQLVESGGGLVQPGGSLRLSCAASGFTFSRYAMSWVRQAPGKGLEWVAAISSGGSLYYPDSVKGRFTISRDNAKNTLYLQMNSLRAEDTAVYYCARGREADGGYFDYWGQGTLVTVSS | 28 |
| hu425-2-2 VK | EIVMTQSPATLSVSPGERATLSCRASESVEYYGTSLMQWYQQKPGQAPRLLIYAASNVESGIPARFSGSGSGTEFTLTISSLQSEDFAVYYCQQSLKVPLTFGGGTKVEIK | 30 |
| hu425-2-3b VH | EVQLVESGGGLVQPGGSLRLSCAASGFTFSRYAMSWVRQAPGKGLEWVAAISSGGSLYYPDSVKGRFTISRDNAKNTLYLQMNSLRAEDTAVYYCARGREADGGYFDYWGQGTLVTVSS | 28 |
| hu425-2-3b VK | EIVLTQSPATLSVSPGERATLSCRASESVEYYGTSLMQWYQQKPGQAPRLLIYAASNVESGIPARFSGSGSGTEFTLTISSLQSEDFAVYYCQQSLKVPLTFGGGTKVEIK | 36 |

TABLE 5

CDR sequences (amino acids) of VH and VK regions of hu425-2-2 and hu425-2-3b

| | CDR1 | SEQ ID NO | CDR2 | SEQ ID NO | CDR3 | SEQ ID NO |
|---|---|---|---|---|---|---|
| hu425-2-2 VH | RYAMSG | 3 | AISSGGSLYYPDSVKG | 26 | GREADGGYFDY | 5 |
| hu425-2-2 VK | RASESVEYYGTSLMQ | 6 | AASNVES | 7 | QQSLKVPLT | 27 |
| hu425-2-3b VH | RYAMSG | 3 | AISSGGSLYYPDSVKG | 26 | GREADGGYFDY | 5 |
| hu425-2-3b VK | RASESVEYYGTSLMQ | 6 | AASNVES | 7 | QQSLKVPLT | 27 |

For affinity determination, Fabs derived from the series of hu425 mAbs were prepared using Pierce Fab Preparation Kit (Cat. No. 44985, ThermoFisher Scientific), and used in the affinity—assay based on surface plasmon resonance (SPR) technology. The results of SPR-determined binding profiles of anti-Tim-3 Fab antibodies were summarized in Table 6. The Fabs of hu425-2-2 and hu425-2-3b have very similar binding profiles with average dissociation constant at 0.419 nM and 0.361 nM, respectively, which are close to that of hu425-1-1.

TABLE 6

Comparison of hu425 Fab binding affinities by SPR

| | Test 1 | | | Test 2 | | | Mean |
|---|---|---|---|---|---|---|---|
| Anti-Tim-3 Fabs | $k_{on}$ (M$^{-1}$s$^{-1}$) | $k_{off}$ (s$^{-1}$) | $K_D$ (nM) | $k_{on}$ (M$^{-1}$s$^{-1}$) | $k_{off}$ (s$^{-1}$) | $K_D$ (nM) | $K_D$ (nM) |
| ch425* | $1.67 \times 10^6$ | $2.04 \times 10^{-4}$ | 0.122 | | | | NA** |
| hu425-1-1 | $6.79 \times 10^5$ | $1.08 \times 10^{-4}$ | 0.159 | $1.26 \times 10^6$ | $4.35 \times 10^{-4}$ | 0.346 | 0.253 |
| hu425-2-2 | $1.71 \times 10^6$ | $7.40 \times 10^{-4}$ | 0.434 | $1.97 \times 10^6$ | $7.95 \times 10^{-4}$ | 0.404 | 0.419 |
| hu425-2-3b | $1.60 \times 10^6$ | $5.70 \times 10^{-4}$ | 0.356 | $1.75 \times 10^6$ | $6.40 \times 10^{-4}$ | 0.366 | 0.361 |

*ch425 is comprised of mu425 variable domains fused to human IgG1 mf/mouse kappa constant regions (the amino acid sequences of the heavy chain and light chain are set for in SEQ ID NOs. 13 and 15)
**NA: not available.

All the humanized antibodies shown above were also confirmed for functional activities on primary human immune cells isolated from healthy donors (described in Example 8).

Example 5 Affinity Comparison of Anti-Tim-3 Antibodies by SPR

Hu425-2-3b and two known Tim-3 antibodies, Ab1 (comprising a heavy chain variable region of SEQ ID NO: 40 and a light chain variable region of SEQ ID NO: 41) and Ab2 (comprising a heavy chain variable region of SEQ ID NO: 42 and a light chain variable region of SEQ ID NO: 43), were generated in human IgG4 format with S228P mutation and characterized for their binding kinetics by SPR assays using BIAcore™ T-200 (GE Life Sciences).

Briefly, anti-human Fab antibody was immobilized on an activated CM5 biosensor chip (Cat.: BR100530, GE Life Sciences). Anti-Tim-3s were flown through the chip surface and captured by anti-human Fab antibody. Then a serial dilution (0.12 nM to 30 nM) of Tim-3-his were flown over the chip surface and changes in surface plasmon resonance signals were analyzed to calculate the association rates ($k_{on}$) and dissociation rates ($k_{off}$) by using the one-to-one Langmuir binding model (BIA Evaluation Software, GE Life Sciences). The equilibrium dissociation constant ($K_D$) was calculated as the ratio $k_{off}/k_{on}$. Hu425-2-3b, Ab1 and Ab2 displayed comparable binding affinity. The antibodies, specifically hu425-2-3b binds to Tim-3 in a dose-dependent manner with a nanomolar KD.

TABLE 7

Comparison of binding affinities of anti-Tim-3s by SPR

| Anti-Tim-3 | Ka (1/Ms) | Kd (1/s) | KD (M) |
|---|---|---|---|
| Hu425-2-3b | 5.28E+05 | 7.78E−04 | 1.47E−09 |
| Ab1 | 4.44E+05 | 1.20E−04 | 2.71E−10 |
| Ab2 | 6.27E+05 | 0.0122 | 1.94E−08 |

Example 6. The Contribution of Mu425/Hu425 CDRs to Tim-3 Binding

Figure 3:
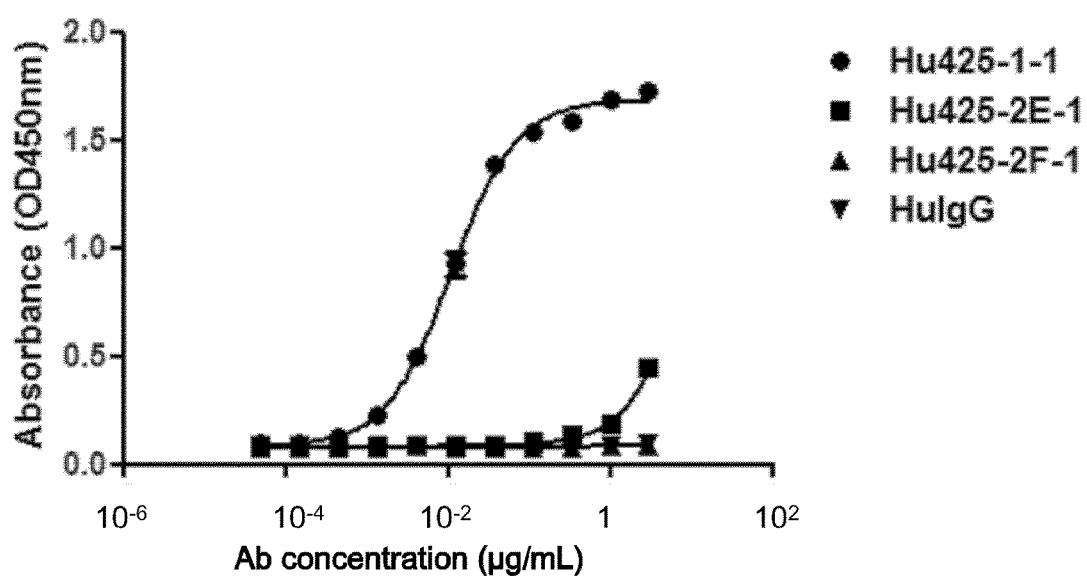
FIG. 3 shows the comparison of Tim-3 binding affinities of hu425-2E-1 and hu425-2F-1 to that of hu425-1-1 in ELISA.

During the process of humanization, several variants with single amino acid mutation from hu425-1-1 were generated. Two of such mutant variants almost completely abolished binding to Tim-3 as seen in FIG. 3, yet each only has a neutral (chemically similar) amino acid substitution, D102E (the mAb was termed hu425-2E-1) and G103A (termed hu425-2F-1), in the CDR3 of heavy chain. Those findings supported the notion that the CDR3 of heavy chain in the mu425 humanized antibodies has significant contribution to the Tim-3-binding functionality.

Figure 4:
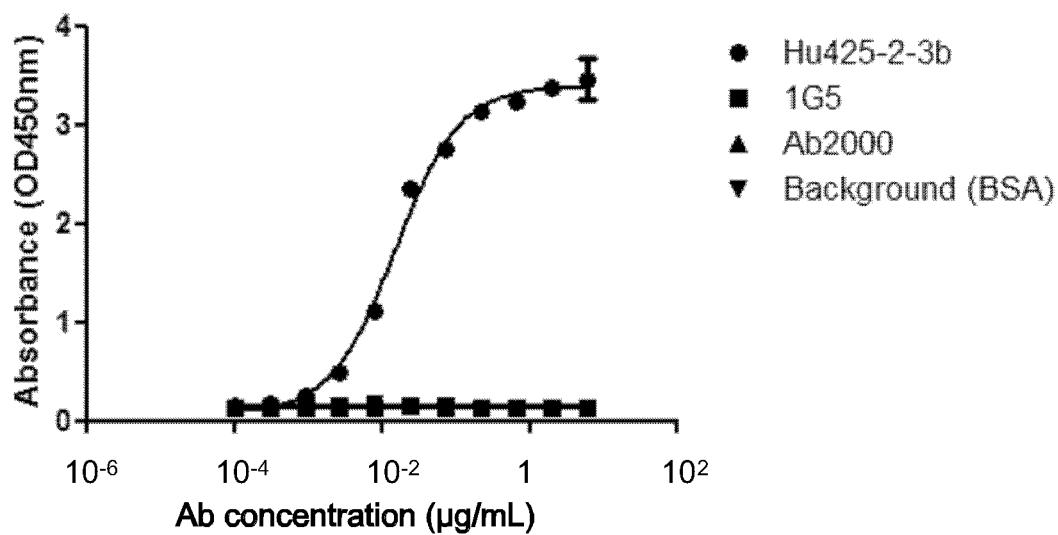
FIG. 4 shows the Tim-3 binding affinities of mAbs 1G5 and Ab2000 together with that of hu425-2-3b in ELISA.

On the other hand, the CDR1 and CDR2 of mu425/hu425 light chain were identical to the mouse germline gene IGKV3-1. Several murine antibodies were also found containing the same murine germline CDR1 and CDR2 sequences in their light chain variable regions, e.g. Ab2000 (U.S. Pat. No. 7,989,597) and mAb 1G5 (U.S. Pat. No. 7,563,874). We investigated whether these antibodies could also bind to Tim-3. For this purpose, Ab2000 and 1G5 were generated with human IgG1mf format and evaluated for Tim-3-mIg binding by ELISA. As shown in FIG. 4, neither Ab2000 nor 1G5 was capable of producing any Tim-3 binding signal in contrast to hu425-2-3b. Therefore, the CDR1 and CDR2 of murine germline gene IGKV3-1 are not sufficient for Tim-3 binding.

To further evaluate the contribution of CDRs to Tim-3 binding, two hybrid antibodies were created by exchanging the heavy chain and light chain of the antibody hu425-2-3b and the antibody Ab1 with each other. Both hu425-2-3b and Ab1 are mouse derived anti-Tim-3s, and they share identical L-CDR1 and L-CDR2 to those of mouse germline IGKV3-1. The heavy chain of hu425-2-3b and the light chain of Ab1 were co-expressed to generate a hybrid antibody 425 HC/Ab1 LC, while hybrid antibody Ab1 HC/425 LC was prepared by co-expression of heavy chain of Ab1 and light chain of hu425-2-3b. The binding activities of hybrid antibodies were analyzed by BioLayer Interferometry (ForteBio Octet). The hybrid antibodies were captured by protein A tips and then dipped in Tim-3-his solution for BLI binding signal analysis. It was observed that Ab1 HC/425 LC retained Tim-3 binding capability, while captured 425 HC/Ab1 LC failed to produce significant binding signal. It suggested that the LC-CDR3 of hu425-2-3b is required for its binding to Tim3 while its L-CDR1 and L-CDR2 is not sufficient for Tim3-binding, or may not be required for binding to Tim3.

Example 7. Blockade of Tim-3-Mediated Phagocytosis by Anti-Tim-3 Antibodies

Tim-3 has been shown to bind to phosphatidylserine (PtdSer) via its IgV domain and mediate phagocytosis of apoptotic cells (DeKruyff et al., *J. Immunol*, 2010, 184: 1918-1930; Nakayama et al., *Blood*, 2009, 113: 3821-3830). PtdSer is a phospholipid that is confined to the inner leaflet of the plasma membrane in normal mammalian cells but becomes exposed on the outer surface of apoptotic cells. PtdSer is involved in the immunosuppression in tumor microenvironment by preventing immune responses (Fadok et al., *J Clin Invest*, 1998, 101:890-898; Frey et al., *Semin Immunopathol.*, 2011, 33:497-516). In vivo administration of anti-Tim-3 antibodies leads to less clearance of apoptotic cells, increased local inflammation and breaking of immune tolerance, suggesting that PtdSer-Tim-3 axis is involved in immune suppression in vivo (Chabtini et al., *J. Immunol* 190:88-96, 2013; Nakayama et al., *Blood* 113: 3821-30, 2009).

Figure 5:
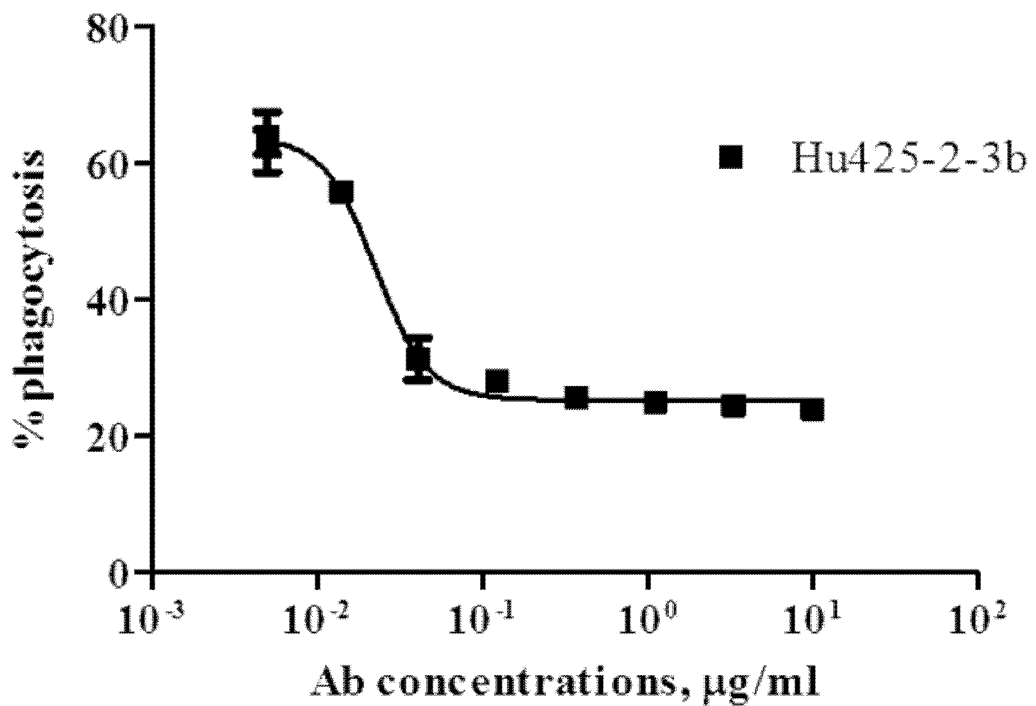
FIG. 5 shows the inhibition of Tim-3-mediated phagocytosis by an anti-Tim-3 antibody hu425-2-3b.

To determine whether anti-Tim-3 antibodies could block Tim-3-mediated phagocytosis, a cell-based assay was established using the sensor and functional readout cell line, THP-1/Tim-3, i.e., THP-1 (ATCC, a human monocyte cell line) stably transfected with the full-length Tim-3 gene. In this assay, HuT78 (ATCC) were induced to undergo limited apoptosis by overnight treatment with 2% ethanol, followed by labeling with CFSE dye (Invitrogen, 1 µM) according to the manufacturer's instruction. THP-1/Tim-3 cells were then co-cultured with the CFSE-labeled apoptotic HuT78 cells for 6 hours in the presence of anti-Tim-3 humanized antibodies. The Tim-3-mediated phagocytosis was determined as percentage of CFSE⁺THP-1/Tim-3 to total THP-1/Tim-3 cells (gated on CD3⁻ population). As shown in FIG. 5, hu425-2-3b dose-dependently inhibited phagocytosis of apoptotic HuT78 cell by THP-1/Tim-3 cells.

Example 8. Activation of IFN-γ Secretion by Anti-Tim-3 Antibodies in Primary Human PBMCs Co-Cultured with T-Cell Engager-Expressing Tumor Cells It was reported that both Tim-3 and PD-1 are inhibitory receptors expressed in activated T cells, which might function to induce T-cell exhaustion (Anderson A C. et al., 2016, *Immunity* 44:989-1004). Tim-3⁺ CD4 and CD8 T-cells from cancer patients indeed secrete much less Th1 cytokine, IFN-γ, than Tim-3⁻ T cells (Arai Y. et al., 2012, *Yonago Acta medica* 55:1-9; Xu B, et al., 2015, *Oncotarget* 6:20592-603).

Figure 6:
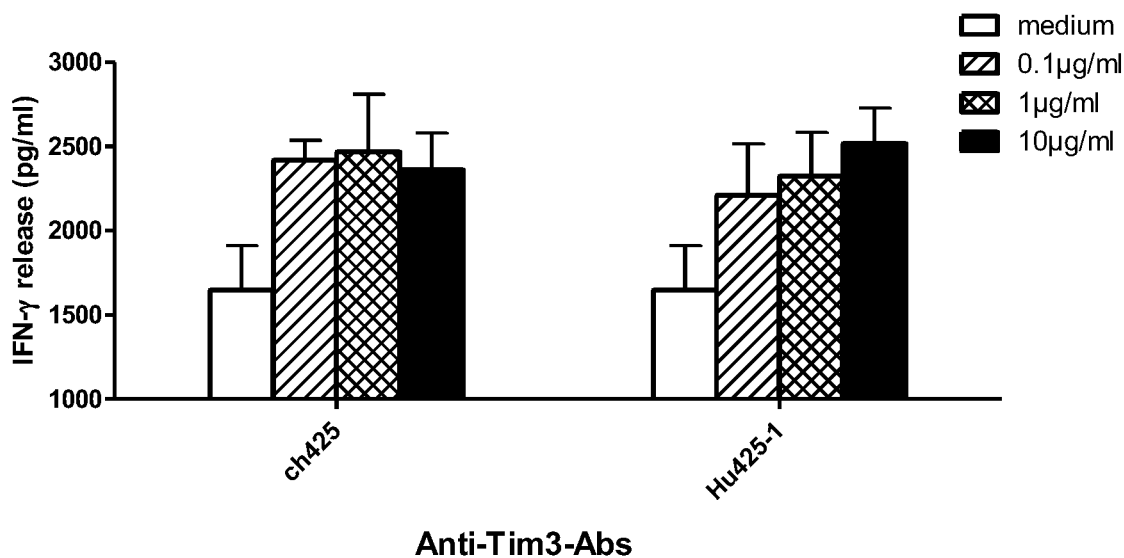
FIG. 6 shows activation of IFN-γ secretion by anti-Tim-3 antibodies, including ch425 and hu425-1-1, in primary human PBMCs.

We have explored the function of Tim-3 and anti-Tim-3 antibodies using anti-CD3 mAb OKT3-actived T-cells in human PBMCs. Peripheral blood mononuclear cells (PBMCs) were isolated from healthy donors using density gradient centrifugation protocol with Histopaque-1077 (Cat. No.: 10771, Sigma). Three days prior to the assay, PBMCs were stimulated with 40 ng/mL of anti-CD3 mAb OKT3 (Cat. No.: 16-0037, eBioscience, USA) to amplify the CD3⁺ T-cells, which are used as effector cells. The target cell termed A549/OS8 was a lung cancer cell line A549 (ATCC) stably-transfected with a T-cell engager (OS8) based on the method described in U.S. Pat. No. 8,735,553. OS8 contains a scFv of anti-human CD3 mAb OKT3 at the N-terminal domains, which directly interact with TCR/CD3 complex and activate T cells. The effector cells, PBMCs, were co-cultured with the mitomycin-C-briefly treated A549/OS8 target cells to mimic the response of activated T cells to tumor cells upon engagement of TCR/CD3 complex. The assay was performed in the presence or absence of anti-Tim-3 antibodies in 96-well flat-bottom plates. After 15-18 hours of co-culture, culture supernatants were assayed for IFN-γ level by ELISA using Ready-Set-Go! ELISA kits (Cat. No.: 88-7316, eBiosciences). As shown in FIG. 6, when the A549/OS8 target cells were co-cultured with the effector cells, anti-Tim-3 antibodies (ch425 and hu425-1-1) induced increased IFN-γ secretion in the effector cells.

Example 9. Activation of CMV-Specific Human T Cells by Anti-Tim-3 Antibodies The functional activity of the Tim-3 antibodies were further assessed using naturally derived T-cells that recognize human CMV PP65 peptide (NLVPMVATV, 495-503, HLA-A2.1-restricted) (Boeckh M, Boeckh M and Geballe A P, 2011, *J Clin Invest.* 121:1673-80). Briefly, PBMCs from healthy donors were initially screened by FACS using anti-HLA-A2 mAb. HLA-A2⁺ PBMCs were then simulated with PP65 peptide (>98% purity, synthesized by GL Biochem, Shanghai) in the complete RPMI with 10% FBS for a week.

Figure 7:
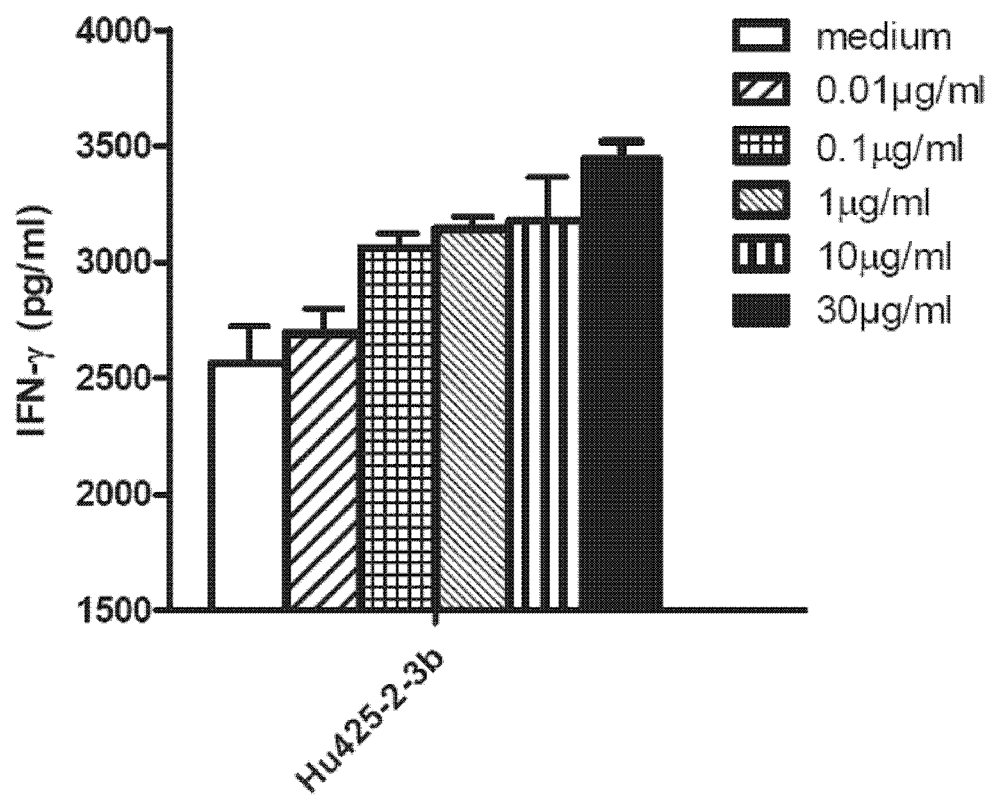
FIG. 7 shows activation of CMV-specific human T cells by anti-Tim-3 antibody hu425-2-3b.

Target cell line A549/A2.1 was established by stable transfection of HLA-A2.1. After 30 minutes of mitomycin-c (100 µg/ml) treatment and pp65 peptide (5 µg/ml) pulse, A549/A2.1 cells (10⁴) were co-cultured with an equal number of pp65-sensitized PBMCs in 96-well plates overnight in the presence or absence of anti-Tim-3 antibodies or controls. IFN-γ in the culture supernatant was determined by ELISA. All conditions were performed in triplicates. As shown in FIG. 7, hu425-2-3b promotes pp65-specific T cells to secrete IFN-γ into the cell culture supernatant.

Example 10. Anti-Tim-3 Antibodies Enhanced NK Cell-Mediated Cytotoxicity

Tim-3 is known to be constitutively expressed on natural killer (NK) cells at relatively high levels (Ndhlovu L C, et al., 2012, *Blood* 119:3734-43; da Silva I P, et al., 2014, *Cancer Immunol Res.* 2:410-22). In melanoma, higher Tim-3 expression on NK cells was found to be associated with advanced tumor stages and poor prognosis. In addition, the NK cell function seemed to be influenced by Tim-3 activity (da Silva I P, et al., 2014, *Cancer Immunol Res.* 2:410-22).

Figure 8:
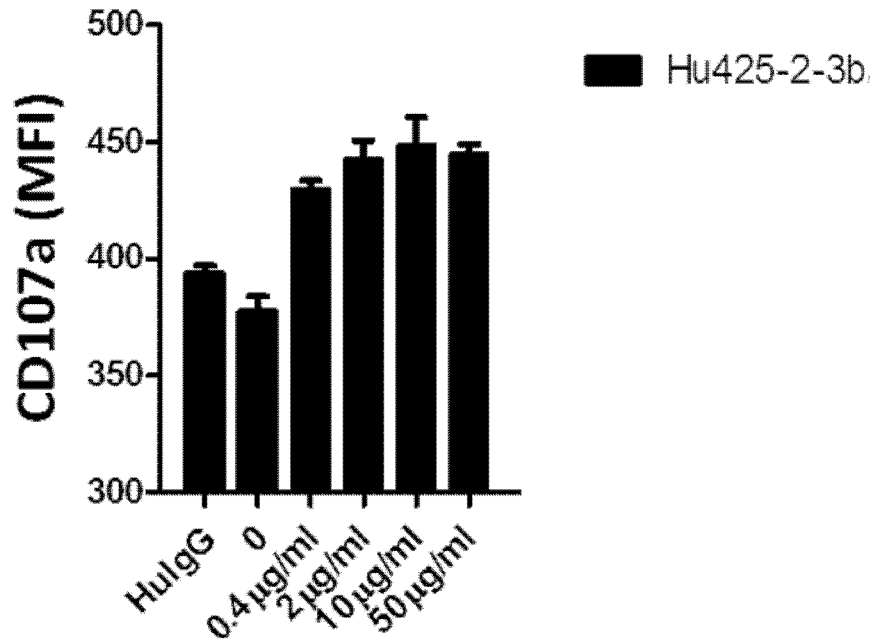
FIGS. 8A-8B show anti-Tim-3 antibody hu425-2-3b promotes NK cell-mediated cytotoxicity.
Figure 8:
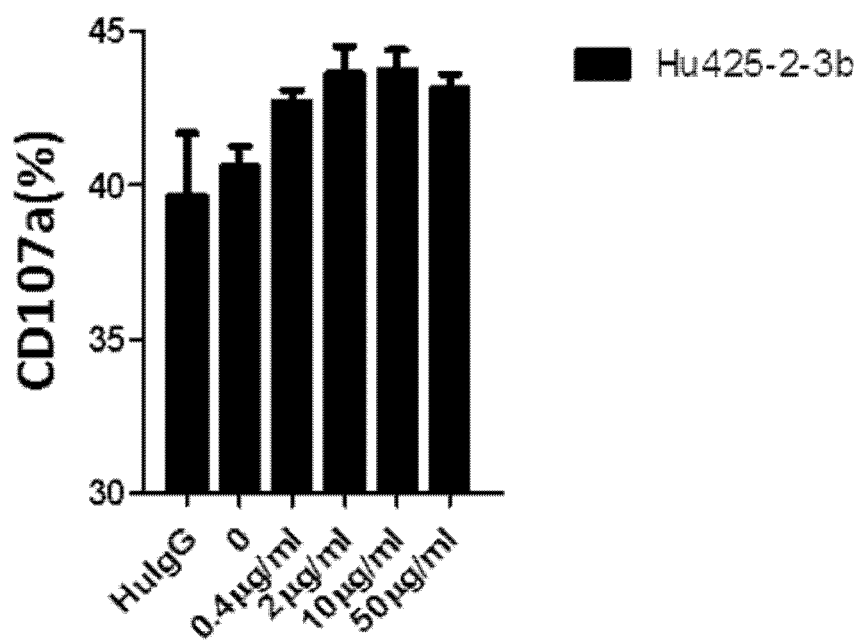

To confirm whether humanized anti-Tim-3 antibodies could promote NK-mediated cytotoxicity, primary NK cells were isolated from PBMCs of healthy donors using an NK cell isolation kit from Miltenyi Biotec (Germany) according to manufacturer's instruction. After one day stimulation with human IL-2 (1000 U/ml), NK cells were co-cultured with K562 cells in the presence of anti-Tim-3 antibodies, brefeldin A and anti-CD107a-APC (eBioscience) at 37° C. for 5 hr. CD107a expression on CD3⁻CD56⁺ NK cells was quantified by flow cytometry. The results showed that anti-Tim-3 antibody hu425-2-3b increased CD107a expression measured by mean fluorescence intensity (MFI) and percentage of cell numbers (FIG. 8).

Figure 9:
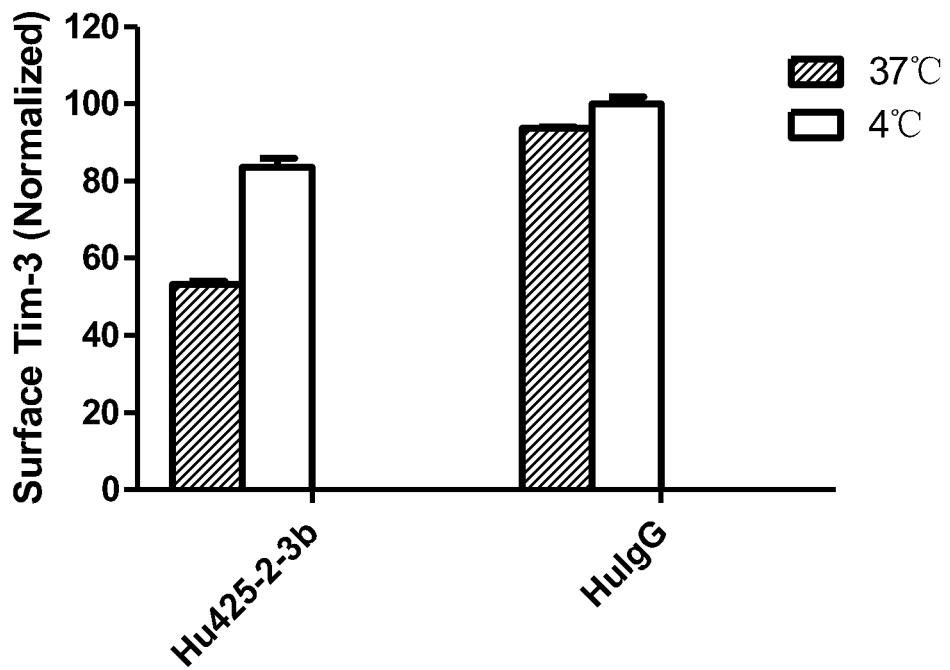
FIG. 9 shows anti-Tim-3 antibody hu425-2-3b reduces the surface expression of Tim-3 receptor.

Example 11. Anti-Tim-3 Antibodies Reduce the Surface Expression of Tim-3 Receptor To address the possibility of hu425-2-3b-including Tim-3 internalization, NK cells from healthy donors were first incubated with hu425-2-3b (10 µg/mL) in complete RPMI1640 media at either 37° C. or 4° C. for 1 hr. Surface expression of Tim-3 receptor was determined by staining with a non-competing Tim-3 Ab mu420 (generated in house), followed by staining with goat anti-mouse IgG-APC (Biolegend). As shown in FIG. 9, hu425-2-3b at 37° C. caused a significant reduction of Tim-3 surface expression compared to the negative control human IgG-treated cells. The reduction was likely due to the anti-Tim-3 antibody-induced receptor internalization because it showed clear temperature dependence in a short time period. The results clearly demonstrated that hu4-25-2-3b induced down-regulation of Tim-3 receptor, probably due to the internalization of Tim-3. By inducing Tim-3 internalization, hu425-2-3b is expected to reduce the interactions of Tim-3 to its multiple ligands (such as galectin-9 and PtdSer).

Example 12. Anti-Tim-3 Antibodies Exhibits Increased Internalization Rate

Figure 10:
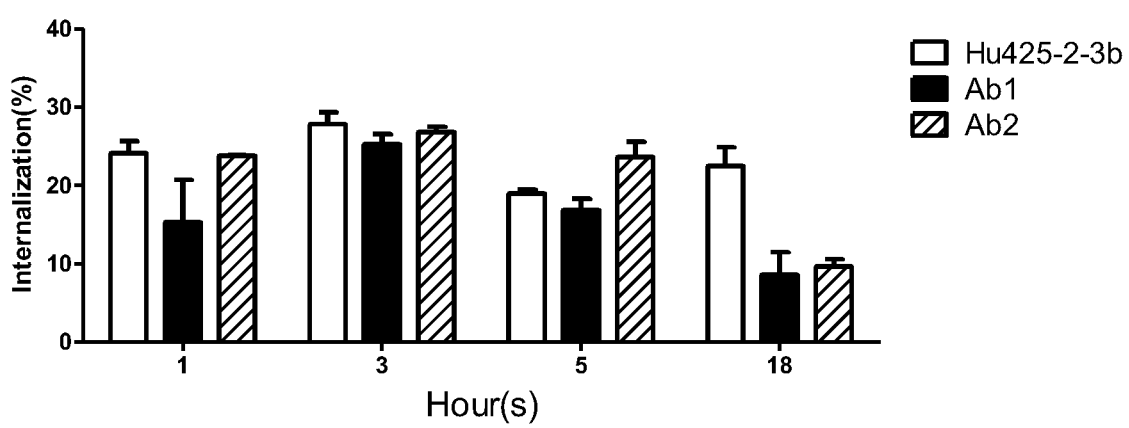
FIG. 10 shows internalization of Tim-3 receptor of anti-Tim-3 antibodies (hu425-2-3b, Ab1 and Ab2).

To further investigate the internalization of the antibodies, anti-Tim-3 antibody-induced internalization was determined using a Tim-3-expressing NK cell line (NK92MI/huTim-3) at different time points (1, 3, 5 and 18 hr). In brief, anti-Tim-3 antibodies (10 µg/ml), including hu425-2-3b, Ab1 and Ab2, were incubated with NK92MI/huTim-3 (5×10⁴) at either 37° C. or 4° C. for 18 hr. Surface expression of Tim-3 receptor was determined by staining with goat anti-human IgG-FITC. The % of internalization was calculated as the reduction (%) of Tim-3 surface expression at 37° C. as compared with the expression level at 4° C. As shown in FIG. 10, during shorter incubation (1-5 hr), hu425-2-3b induced comparable levels of Tim-3 internalization as Ab1 and Ab2. It did demonstrate a significantly persistent internalization than both Ab1 and Ab2 after 18 hours of incubation, suggesting the persistent activity of Tim-3 internalization by hu425-2-3b.

Example 13. Humanized Anti-Tim-3 mAbs Stimulate Immune Cells Alone and in Combination with PD-1 mAb It has been reported that the immune inhibitory receptors PD-1 and Tim-3 were up-regulated in "dysfunctional" tumor antigen-specific CD8⁺ T cells in patients with advanced tumors and chronic viral infections (Fourcade J, et al., 2010, *J Exp Med.* 207:2175-86; Thommen D S, et al., 2015, *Cancer Immunol Res.* 3:1344-55; Jin H T, et al., 2010, *Proc*

*Natl Acad Sci USA.* 107:14733-8). Simultaneous blockade of both PD-1 and Tim-3 receptors could expand vaccine induced NY-ESO-1-specific CD8⁺ T cells (Fourcade J., et al., 2014, *Cancer Res.* 74:1045-55). A conventional T-cell response assay, mixed lymphocyte reaction (MLR), was set up to characterize the potential costimulatory effects by the anti-Tim-3 and anti-PD-1 antibodies. In brief, "stimulator PBMCs" were pre-treated with mitomycin-c (100 µg/ml, Sigma) and co-cultured with "responder PBMCs" of a different donor at one to one ratio in the complete RPMI1640 media with 10% AB serum (Sigma) plus anti-Tim-3 and/or anti-PD-1 mAb 317-4B6 (also named hu317-4B6, 317-4B6/IgG4mt10, described in U.S. Pat. No. 8,735,553). The reactions were carried out in 96-well flat-bottom plates for 4 days with triplicate data point setting for each condition. IFN-γ secretion in the cell culture supernatant was analyzed as readout.

Figure 11:
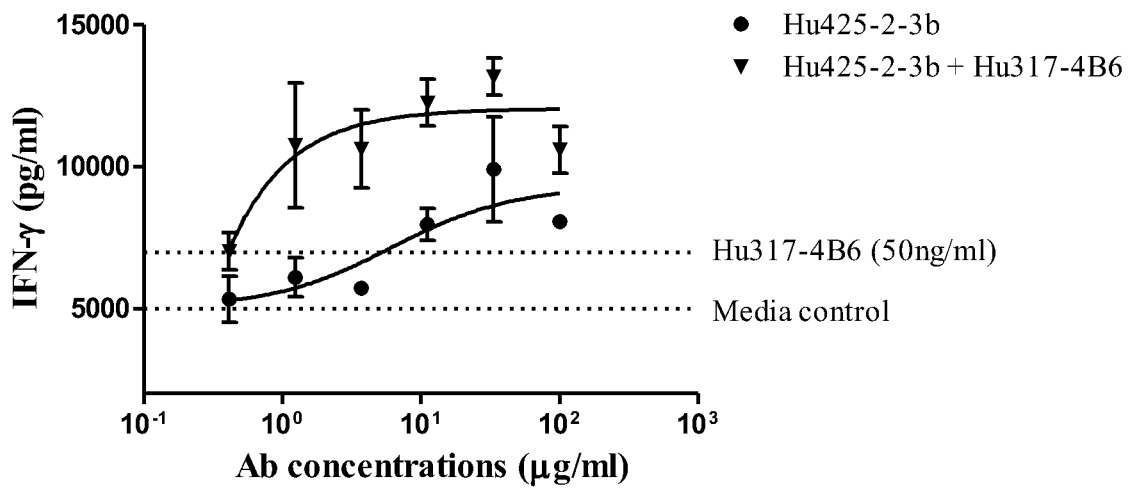
FIG. 11 shows anti-Tim-3 antibody hu425-2-3b, alone or in combination with an anti-PD-1 antibody hu317-4B6, enhances IFN-γ secretion in MLR.

The results showed that hu425-2-3b significantly enhanced IFN-γ production in the MLR dose-dependently. Combination of hu425-2-3b with 317-4B6 (50 ng/ml) lead to a greater increase in IFN-γ production than hu425-2-3b or anti-PD-1 antibody alone, demonstrating the co-stimulating effects of the anti-Tim-3 mAb with the anti-PD-1 mAb (FIG. 11).

Mitomycin-C-pretreated "stimulator PBMCs" were co-cultured with "responder PBMCs" in the presence of anti-Tim-3 mAb, either hu425-2-3b or hu425-2-3b, plus an anti-PD-1 Ab hu317-4b6 (50 ng/ml) in 96-well flat-bottom plates for 4 days. IFN-γ in the supernatant was determined by ELISA. All conditions were performed in triplicates. Results were shown in mean+SD.

Example 14. Hu425-2-3b Did not have ADCC and CDC Effector Functions

The ability of hu425-2-3b to induce ADCC and CDC was determined using in vitro assay as described below. IgG1mf (SEQ ID NO: 21) is an IgG1 mutant containing a combination of mutations, $E_{233}P$, $L_{234}A$, $L_{235}A$, $L_{236}\Delta$ and $P_{329}A$ (amino acid numbering is based on EU system). These mutations are designed to eliminate the binding of Fc to all FcγRs as well as C1q.

ADCC(Antibody-Dependent Cell-Mediated Cytotoxicity).

A classical ADCC assay was set up to determine whether hu425-2-3b could induce ADCC. The assay effector cell line, NK92MI/CD16V cells, was generated from NK92MI cells (ATCC) by co-transducing expression plasmids containing $CD16_{V158}$ (V158 allele) and FcRγ cDNAs. Tim-3-expressing T cell line, HuT78/Tim-3, was used as target cells. The effector cells (4×10⁴) were co-cultured with an equal number of target cells, for 5 hours in the presence of hu425-2-3b or control antibodies, either the positive control anti-MHC-I A, B, C (Biolegend) or a negative control human IgG. Cytotoxicity was determined by lactate dehydrogenase (LDH) release assay using the CytoTox 96 Non-Radioactive Cytotoxicity Assay kit (Promega, Madison, Wis.). Specific lysis was determined by the following equation.

$$\% \text{ Specific lysis} = \frac{\text{Experimental} - \text{Effector Spotaneous} - \text{Target Spotaneous}}{\text{Target Maximum} - \text{Target Spotaneous}} \times 100$$

Figure 12:
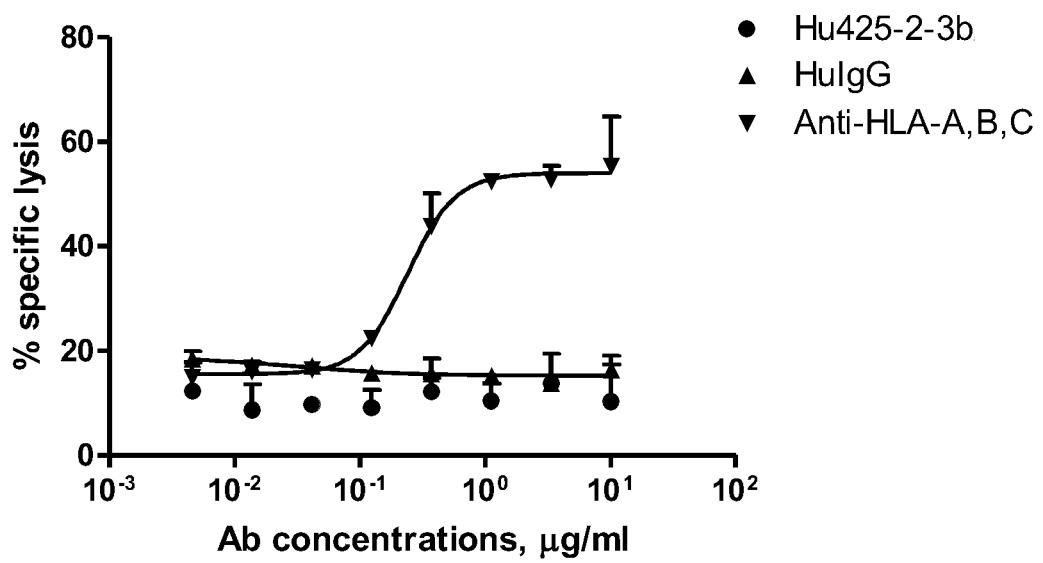
FIGS. 12A-12B show anti-Tim-3 antibody hu425-2-3b did not induce ADCC (antibody-dependent cell-mediated cytotoxicity) and CDC (complement dependent cytotoxicity).
Figure 12:
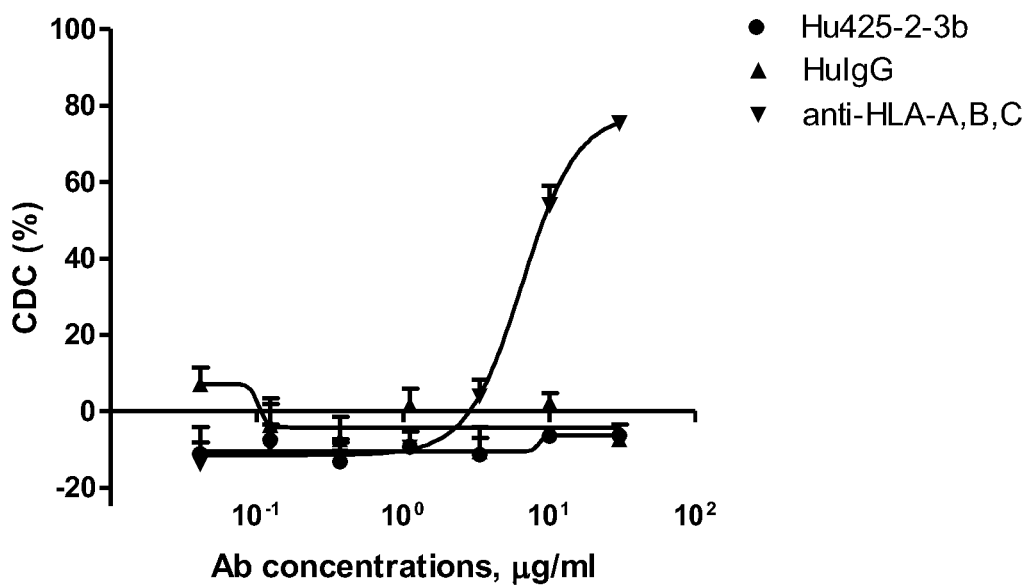

The results confirmed that hu425-2-3b had the same basal level of ADCC as that of negative control, whereas anti-MHC-I A, B, C induced ADCC in a dose-dependent manner (FIG. 12A).

CDC(Complement-Dependent Cytotoxicity)

Whether hu425-2-3b would trigger CDC was determined using pre-activated human PBMCs and fresh autologous sera from healthy donors. Cell lysis by CDC was determined by a Celltiter glo assay kit (Promega, Beijing, China). In brief, PBMCs from healthy donors were pre-activated with PHA (10 µg/ml, Sigma) for 3 days, and then were incubated in RPMI1640 plus autologous serum (15%) and hu425-2-3b or control antibodies (0.04-30 µg/mL) overnight at 37° C. The cell death due to CDC was assayed by the decrease of ATP released from viable cells after cell lysis at the end of reaction. Anti-MHC-I A, B, C was used as a positive control. The fluorescence readout was conducted using a 96-well fluorometer (PHERA Star FS, BMG LABTECH), and the CDC activities were calculated from the relative fluorescence unit (RFU) readout as follows: % CDC activity= [(RFU test−RFU background)/(RFU at total cell lysis−RFU background)]×100. The experimental results demonstrated that hu425-2-3b had no detectable CDC with PBMCs isolated from two different donors. In contrast, the positive control antibody, anti-MHC-I, induced significant CDC activity (FIG. 12B).

The results showed that hu425-2-3b eliminate ADCC and CDC effector functions while maintaining optimal physicochemical properties.

Example 15. Anti-Tim-3 Antibody in Combination with an Anti-PD-1 Antibody Inhibits Tumor Growth in a Mouse Xenograft Cancer Model The potential anti-cancer activity of the Tim-3 antibody was evaluated in combination with anti-PD-1 antibody by a xenograft cancer model, in which immune-compromised mice were implanted with human cancer cells and allogeneic PBMCs. Briefly, NOD/SCID mice were pre-treated with cyclophosphamide (150 mg/kg) for 2 days before tumor inoculation. Human PBMCs were isolated from peripheral blood of healthy volunteers, mixed with A431 epidermoid carcinoma cells (Cat. No. CRL-1555, ATCC) in Matrigel, and injected subcutaneously into the animals. Starting from day 0, animals were randomly assigned into 4 groups with 5-10 mice per group. Mice were treated once a week (QW) via i.p. injection with vehicle (PBS), 5 mg/kg anti-Tim-3 mAb chimeric 425 (ch425), anti-PD-1 antibody 317-4B6 (1 mg/kg) or combination therapy (5 mg/kg ch425 plus 1 mg/kg of 317-4B6) for 4 weeks. Tumor size of individual mouse was recorded twice weekly, with mice being monitored daily for clinical signs of toxicity for the duration of the study. Tumor volumes were calculated using the formula: $[D \times (d^2)]/2$, in which D represents the long diameter of the tumor, and d represents the short diameter. All animal studies were performed following Beigene Animal Care and Use Procedure.

Figure 13:
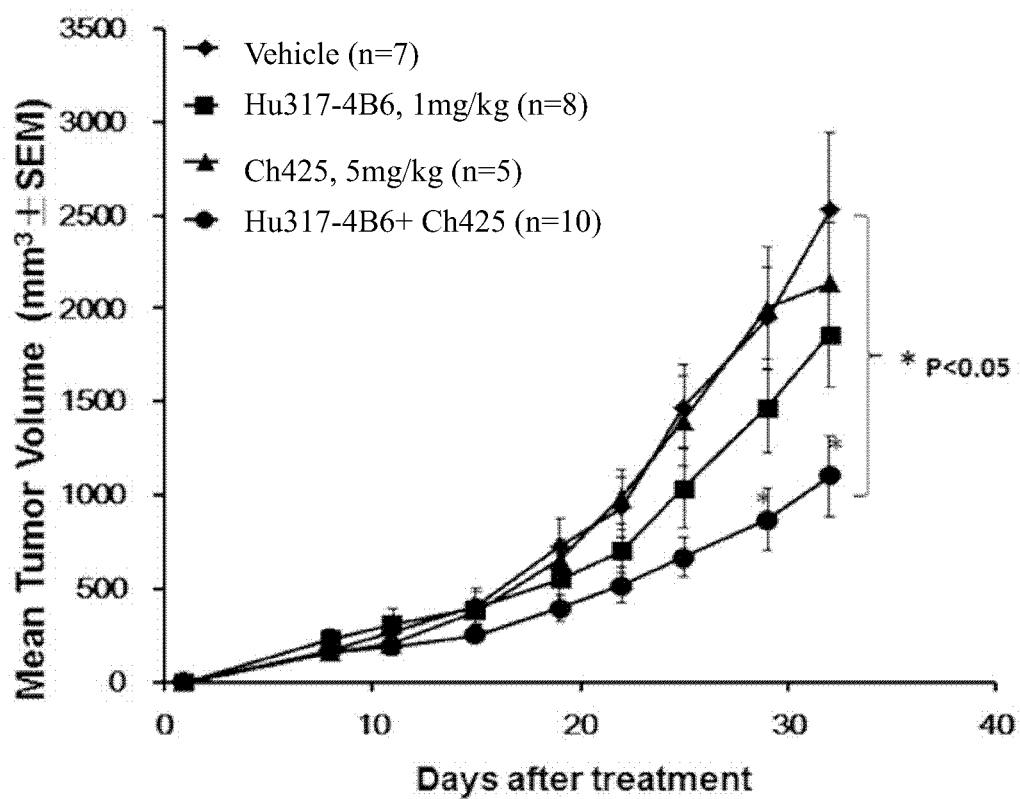
FIG. 13 shows the anti-tumor effects of anti-Tim-3 antibody ch425, anti-PD-1 antibody hu317-4B6, and combination thereof in a human A431 allogeneic xenograft model.

As shown in FIG. 13, treatment with ch425 alone at a dose of 5 mg/kg had little or no effect on tumor growth. 317-4B6 at a dose of 1 mg/kg showed a trend toward delayed tumor growth without statistical significance (P>0.05). However, combined treatment with ch425 and 317-4B6 showed significantly synergistic effects, inhibiting tumor growth by more than 60% versus the vehicle-treated group.

The results indicated that combination therapy of ch425 with 317-4B6 could activate human immune cells to inhibit tumor growth in a mouse in vivo cancer model, which was consistent with the in vitro data described in Example 11.

The invention claimed is:

1. An antibody capable of binding to human Tim-3, comprising:
   (a) a heavy chain variable region (VH) comprising a VH-CDR1 amino acid sequence of SEQ ID NO 3, a VH-CDR2 amino acid sequence of SEQ ID NO 26, a VH-CDR3 amino acid sequence of SEQ ID NO 5; and a light chain variable region (VL) comprising a VL-CDR1 amino acid sequence of SEQ ID NO 6, a VL-CDR2 amino acid sequence of SEQ ID NO 7, and a VL-CDR3 amino acid sequence of SEQ ID NO 27;
   (b) a VH comprising a VH-CDR1 amino acid sequence of SEQ ID NO 3, a VH-CDR2 amino acid sequence of SEQ ID NO 4, a VH-CDR3 amino acid sequence of SEQ ID NO 5; and VL comprising a VL-CDR1 amino acid sequence of SEQ ID NO 6, a VL-CDR2 amino acid sequence of SEQ ID NO 7, and a VL-CDR3 amino acid sequence of SEQ ID NO 27;
   (c) a VH comprising a VH-CDR1 amino acid sequence of SEQ ID NO 3, a VH-CDR2 amino acid sequence of SEQ ID NO 26, a VH-CDR3 amino acid sequence of SEQ ID NO 5; and VL comprising a VL-CDR1 amino acid sequence of SEQ ID NO 6, a VL-CDR2 amino acid sequence of SEQ ID NO 7, and a VL-CDR3 amino acid sequence of SEQ ID NO 8; or
(d) a VH comprising a VH-CDR1 amino acid sequence of SEQ ID NO 3, a VH-CDR2 amino acid sequence of SEQ ID NO 4, a VH-CDR3 amino acid sequence of SEQ ID NO 5; and VL comprising a VL-CDR1 amino acid sequence of SEQ ID NO 6, a VL-CDR2 amino acid sequence of SEQ ID NO 7, and a VL-CDR3 amino acid sequence of SEQ ID NO 8.

2. The antibody of claim 1, wherein the antibody comprises:
a heavy chain variable region (VH) comprising a VH-CDR1 amino acid sequence of SEQ ID NO 3, a VH-CDR2 amino acid sequence of SEQ ID NO 26 and a VH-CDR3 amino acid sequence of SEQ ID NO 5; and a light chain variable region (VL) comprising a VL-CDR1 amino acid sequence of SEQ ID NO 6, a VL-CDR2 amino acid sequence of SEQ ID NO 7 and a VL-CDR3 amino acid sequence of SEQ ID NO 27.

3. The antibody of claim 1, wherein the antibody is a humanized antibody molecule.

4. The antibody of claim 1, wherein the antibody comprises a heavy chain variable domain having at least 95% sequence identity with the amino acid sequence of SEQ ID NOs 9, 17, 28 or 40.

5. The antibody of claim 1, wherein the antibody comprises a heavy chain variable domain having at least 95% sequence identity with the amino acid sequence of SEQ ID NOs 9, 17 or 28.

6. The antibody of claim 1, wherein the antibody comprises a light chain variable domain having at least 95% sequence identity with the amino acid sequence of SEQ ID NO 11, 19, 30 or 36.

7. The antibody of claim 1, wherein the antibody comprises:
(a) a heavy chain variable domain having at least 95% sequence identity with the amino acid sequence of SEQ ID NO 9, and a light chain variable domain having at least 95% sequence identity with the amino acid sequence of SEQ ID NO 11;
(b) a heavy chain variable domain having at least 95% sequence identity with the amino acid sequence of SEQ ID NO 9, and a light chain variable domain having at least 95% sequence identity with the amino acid sequence of SEQ ID NO 19;
(c) a heavy chain variable domain having at least 95% sequence identity with the amino acid sequence of SEQ ID NO 9, and a light chain variable domain having at least 95% sequence identity with the amino acid sequence of SEQ ID NO 30;
(d) a heavy chain variable domain having at least 95% sequence identity with the amino acid sequence of SEQ ID NO 9, and a light chain variable domain having at least 95% sequence identity with the amino acid sequence of SEQ ID NO 36;
(e) a heavy chain variable domain having at least 95% sequence identity with the amino acid sequence of SEQ ID NO 17, and a light chain variable domain having at least 95% sequence identity with the amino acid sequence of SEQ ID NO 11;
(f) a heavy chain variable domain having at least 95% sequence identity with the amino acid sequence of SEQ ID NO 17, and a light chain variable domain having at least 95% sequence identity with the amino acid sequence of SEQ ID NO 19;
(g) a heavy chain variable domain having at least 95% sequence identity with the amino acid sequence of SEQ ID NO 17, and a light chain variable domain having at least 95% sequence identity with the amino acid sequence of SEQ ID NO 30;
(h) a heavy chain variable domain having at least 95% sequence identity with the amino acid sequence of SEQ ID NO 17, and a light chain variable domain having at least 95% sequence identity with the amino acid sequence of SEQ ID NO 36;
(i) a heavy chain variable domain having at least 95% sequence identity with the amino acid sequence of SEQ ID NO 28, and a light chain variable domain having at least 95% sequence identity with the amino acid sequence of SEQ ID NO 11;
(j) a heavy chain variable domain having at least 95% sequence identity with the amino acid sequence of SEQ ID NO 28, and a light chain variable domain having at least 95% sequence identity with the amino acid sequence of SEQ ID NO 19;
(k) a heavy chain variable domain having at least 95% sequence identity with the amino acid sequence of SEQ ID NO 28, and a light chain variable domain having at least 95% sequence identity with the amino acid sequence of SEQ ID NO 30;
(l) a heavy chain variable domain having at least 95% sequence identity with the amino acid sequence of SEQ ID NO 28, and a light chain variable domain having at least 95% sequence identity with the amino acid sequence of SEQ ID NO 36;
(m) a heavy chain variable domain having at least 95% sequence identity with the amino acid sequence of SEQ ID NO 40, and a light chain variable domain having at least 95% sequence identity with the amino acid sequence of SEQ ID NO 11;
(n) a heavy chain variable domain having at least 95% sequence identity with the amino acid sequence of SEQ ID NO 40, and a light chain variable domain having at least 95% sequence identity with the amino acid sequence of SEQ ID NO 19;
(o) a heavy chain variable domain having at least 95% sequence identity with the amino acid sequence of SEQ ID NO 40, and a light chain variable domain having at least 95% sequence identity with the amino acid sequence of SEQ ID NO 30; or
(p) a heavy chain variable domain having at least 95% sequence identity with the amino acid sequence of SEQ ID NO 40, and a light chain variable domain having at least 95% sequence identity with the amino acid sequence of SEQ ID NO 36.

8. The antibody of claim 1, wherein the antibody comprises:
(a) a heavy chain variable domain comprising the amino acid sequence of SEQ ID NO 9, and a light chain variable domain comprising the amino acid sequence of SEQ ID NO 11;
(b) a heavy chain variable domain comprising the amino acid sequence of SEQ ID NO 17, and a light chain variable domain comprising the amino acid sequence of SEQ ID NO 19;
(c) a heavy chain variable domain comprising the amino acid sequence of SEQ ID NO 28, and a light chain variable domain comprising the amino acid sequence of SEQ ID NO 30;

(d) a heavy chain variable domain comprising the amino acid sequence of SEQ ID NO 28, and a light chain variable domain comprising the amino acid sequence of SEQ ID NO 36; or (e) a heavy chain variable domain comprising the amino acid sequence of SEQ ID NO 40, and a light chain variable domain comprising the amino acid sequence of SEQ ID NO 36.

9. The antibody of claim 1, wherein the antibody comprises a heavy chain having at least 95% sequence identity with the amino acid sequence of SEQ ID NO 13, 22 or 32.

10. The antibody of claim 1, wherein the antibody comprises a light chain having at least 95% sequence identity with the amino acid sequence of SEQ ID NO 15, 24, 34 or 38.

11. The antibody of claim 1, wherein the antibody comprises:

(a) a heavy chain having at least 95% sequence identity with the amino acid sequence of SEQ ID NO 13, and a light chain having at least 95% sequence identity with the amino acid sequence of SEQ ID NO 15;

(b) a heavy chain having at least 95% sequence identity with the amino acid sequence of SEQ ID NO 13, and a light chain having at least 95% sequence identity with the amino acid sequence of SEQ ID NO 24;

(c) a heavy chain having at least 95% sequence identity with the amino acid sequence of SEQ ID NO 13, and a light chain having at least 95% sequence identity with the amino acid sequence of SEQ ID NO 34;

(d) a heavy chain having at least 95% sequence identity with the amino acid sequence of SEQ ID NO 13, and a light chain having at least 95% sequence identity with the amino acid sequence of SEQ ID NO 38;

(e) a heavy chain having at least 95% sequence identity with the amino acid sequence of SEQ ID NO 22, and a light chain having at least 95% sequence identity with the amino acid sequence of SEQ ID NO 15;

(f) a heavy chain having at least 95% sequence identity with the amino acid sequence of SEQ ID NO 22, and a light chain having at least 95% sequence identity with the amino acid sequence of SEQ ID NO 24;

(g) a heavy chain having at least 95% sequence identity with the amino acid sequence of SEQ ID NO 22, and a light chain having at least 95% sequence identity with the amino acid sequence of SEQ ID NO 34;

(h) a heavy chain having at least 95% sequence identity with the amino acid sequence of SEQ ID NO 22, and a light chain having at least 95% sequence identity with the amino acid sequence of SEQ ID NO 38;

(i) a heavy chain having at least 95% sequence identity with the amino acid sequence of SEQ ID NO 32, and a light chain having at least 95% sequence identity with the amino acid sequence of SEQ ID NO 15;

(j) a heavy chain having at least 95% sequence identity with the amino acid sequence of SEQ ID NO 32, and a light chain having at least 95% sequence identity with the amino acid sequence of SEQ ID NO 24;

(k) a heavy chain having at least 95% sequence identity with the amino acid sequence of SEQ ID NO 32, and a light chain having at least 95% sequence identity with the amino acid sequence of SEQ ID NO 34; or (l) a heavy chain having at least 95% sequence identity with the amino acid sequence of SEQ ID NO 32, and a light chain having at least 95% sequence identity with the amino acid sequence of SEQ ID NO 38.

12. The antibody of claim 1, wherein the antibody comprises:

(a) a heavy chain comprising the amino acid sequence of SEQ ID NO 13, and a light chain comprising the amino acid sequence of SEQ ID NO 15;

(b) a heavy chain comprising the amino acid sequence of SEQ ID NO 22, and a light chain comprising the amino acid sequence of SEQ ID NO 24;

(c) a heavy chain comprising the amino acid sequence of SEQ ID NO 32, and a light chain comprising the amino acid sequence of SEQ ID NO 34; or (d) a heavy chain comprising the amino acid sequence of SEQ ID NO 32, and a light chain comprising the amino acid sequence of SEQ ID NO 38.

13. The antibody of claim 1, wherein the antibody comprises one or more of:

(a) a light chain with an Aspartic acid to Glutamic acid mutation at position 1 of SEQ ID NO 24;

(b) a light chain with a Leucine to Methionine mutation at position 4 of SEQ ID NO 24;

(c) a light chain with a Valine to Isoleucine mutation at position 62 of SEQ ID NO 24;

(d) a light chain with a Aspartic acid to Glutamic acid mutation at position 74 of SEQ ID NO 24;

(e) a light chain with a Methionine to Leucine mutation at position 96 of SEQ ID NO 24;

(f) a heavy chain with a Phenylalanine to Tyrosine mutation at position 59 of SEQ ID NO 22;

(g) (h) (g) a heavy chain with a Proline to Valine mutation at position 60 of SEQ ID NO 22; a heavy chain with a Serine to Threonine mutation at position 77 of SEQ ID NO 22; or (i) a heavy chain with a Cysteine to Leucine mutation at position 78 of SEQ ID NO 22.

14. The antibody of claim 1, wherein the antibody is a Fab, F(ab')2, Fv, or a single chain Fv (ScFv).

15. The antibody of claim 1, wherein the antibody comprises a heavy chain constant region of the subclass of IgG1, IgG2, IgG3, or IgG4 or a variant thereof, and a light chain constant region of the type of kappa or lambda or a variant thereof.

16. The antibody of claim 15, wherein the antibody comprises a variant heavy chain constant region of the subclass of IgG1, IgG2, IgG3, or IgG4, wherein the variant heavy chain constant region provides a reduced or eliminated effector function.

17. The antibody of claim 16, wherein the effector function is antibody-dependent cell-mediated cytotoxicity (ADCC) or complement-dependent cytotoxicity (CDC).

18. The antibody of claim 15, wherein the antibody comprises a heavy chain constant region of human IgG1 or a variant thereof.

19. The antibody of claim 18, wherein the variant heavy chain constant region of human IgG1 comprises one or more mutations selected from a group consisting of $E_{233}P$, $L_{234}A$, $L_{235}A$, $L_{236}\Delta$ and $P_{329}A$.

20. The antibody of claim 19, wherein the variant human IgG1 heavy chain constant region comprising the amino sequence of SEQ ID NO 21, and a human kappa light chain constant religion.

21. A pharmaceutical composition, comprising the antibody of claim 1, and a pharmaceutically acceptable excipient.

22. A method of stimulating an immune response in a subject, comprising administrating to a subject in need thereof an antibody of claim 1 in an amount effective to stimulate the immune respond.

23. A method for treating a cancer or a tumor, comprising administrating to a subject in need thereof the antibody of claim 1 in an amount effective to treat the cancer or tumor.

24. The method of claim 23, wherein the cancer is selected from a lung cancer, a liver cancer, a stomach cancer, a cervical cancer, a melanoma, a renal cancer, a breast cancer, a colorectal cancer, a leukemia, a lymphoma, an ovarian cancer, a head and neck cancer or a metastatic lesion of the cancer.

25. The method of claim 23, wherein the antibody is administrated in combination with a second therapeutic agent or procedure, wherein the second therapeutic agent or procedure is selected from a chemotherapy, a targeted therapy, an oncolytic drug, a cytotoxic agent, an immune-based therapy, a cytokine, a surgical procedure, a radiation procedure, an activator of a costimulatory molecule, an inhibitor of an inhibitory molecule, a vaccine, or a cellular immunotherapy.

26. The method of claim 23, wherein the antibody is administered in combination with an inhibitor of an immune checkpoint molecule selected from PD-1, PD-L1, PD-L2, CTLA-4, LAG-3, CEACAM-1, CEACAM-5, VISTA, BTLA, TIGIT, LAIR1, CD160, 2B4 or TGFR.

27. The method of claim 23, wherein the antibody is administered in combination with an anti-PD-1 mAb 317-4B6, or 317-4B6/IgG4mt10.

28. A method of treating an infectious disease, comprising administering to a subject in need thereof an antibody of claim 1 in an amount effective to treat the infectious disease.

29. The method of claim 28, wherein the infectious disease is a chronic viral infection, selected from HIV infection and HCV infection.

\* \* \* \* \*

UNITED STATES PATENT AND TRADEMARK OFFICE
CERTIFICATE OF CORRECTION

PATENT NO. : 11,203,637 B2
APPLICATION NO. : 16/328047
DATED : December 21, 2021
INVENTOR(S) : Tong Zhang et al.

It is certified that error appears in the above-identified patent and that said Letters Patent is hereby corrected as shown below:

In the Claims

In Claim 13, Column 80, Lines 29-32, please replace:
"(g) (h) (g) a heavy chain with a Proline to Valine mutation at position 60 of SEQ ID NO 22; a heavy chain with a Serine to Threonine mutation at position 77 of SEQ ID NO 22; or"
With:
-- (g) a heavy chain with a Proline to Valine mutation at position 60 of SEQ ID NO 22;
(h) a heavy chain with a Serine to Threonine mutation at position 77 of SEQ ID NO 22; or --

Signed and Sealed this
Seventeenth Day of January, 2023

Katherine Kelly Vidal
*Director of the United States Patent and Trademark Office*

SEQUENCE LISTING

<160> NUMBER OF SEQ ID NOS: 43

<210> SEQ ID NO 1
<211> LENGTH: 301
<212> TYPE: PRT
<213> ORGANISM: Homo sapiens

<400> SEQUENCE: 1

```
Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Leu Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
    210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
        275                 280                 285

Gln Pro Ser Gln Pro Leu Gly Cys Arg Phe Ala Met Pro
    290                 295                 300
```

<210> SEQ ID NO 2
<211> LENGTH: 202
<212> TYPE: PRT
<213> ORGANISM: Homo sapiens

<400> SEQUENCE: 2

```
Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
```

```
                       20                  25                  30
Asn Ala Tyr Leu Pro Cys Phe Tyr Thr Pro Ala Ala Pro Gly Asn Leu
             35                  40                  45

Val Pro Val Cys Trp Gly Lys Gly Ala Cys Pro Val Phe Glu Cys Gly
 50                  55                  60

Asn Val Val Leu Arg Thr Asp Glu Arg Asp Val Asn Tyr Trp Thr Ser
 65                  70                  75                  80

Arg Tyr Trp Leu Asn Gly Asp Phe Arg Lys Gly Asp Val Ser Leu Thr
                 85                  90                  95

Ile Glu Asn Val Thr Leu Ala Asp Ser Gly Ile Tyr Cys Cys Arg Ile
             100                 105                 110

Gln Ile Pro Gly Ile Met Asn Asp Glu Lys Phe Asn Leu Lys Leu Val
         115                 120                 125

Ile Lys Pro Ala Lys Val Thr Pro Ala Pro Thr Leu Gln Arg Asp Phe
     130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                 165                 170                 175

Ser Thr Leu Ala Asn Glu Leu Arg Asp Ser Arg Leu Ala Asn Asp Leu
             180                 185                 190

Arg Asp Ser Gly Ala Thr Ile Arg Ile Gly
         195                 200

<210> SEQ ID NO 3
<211> LENGTH: 5
<212> TYPE: PRT
<213> ORGANISM: Mus musculus

<400> SEQUENCE: 3

Arg Tyr Ala Met Ser
1               5

<210> SEQ ID NO 4
<211> LENGTH: 16
<212> TYPE: PRT
<213> ORGANISM: Mus musculus

<400> SEQUENCE: 4

Ala Ile Ser Ser Gly Gly Ser Leu Tyr Phe Pro Asp Ser Val Lys Gly
1               5                   10                  15

<210> SEQ ID NO 5
<211> LENGTH: 11
<212> TYPE: PRT
<213> ORGANISM: Mus musculus

<400> SEQUENCE: 5

Gly Arg Glu Ala Asp Gly Gly Tyr Phe Asp Tyr
1               5                   10

<210> SEQ ID NO 6
<211> LENGTH: 15
<212> TYPE: PRT
<213> ORGANISM: Mus musculus

<400> SEQUENCE: 6

Arg Ala Ser Glu Ser Val Glu Tyr Tyr Gly Thr Ser Leu Met Gln
1               5                   10                  15
```

<210> SEQ ID NO 7
<211> LENGTH: 7
<212> TYPE: PRT
<213> ORGANISM: Mus musculus

<400> SEQUENCE: 7

Ala Ala Ser Asn Val Glu Ser
1               5

<210> SEQ ID NO 8
<211> LENGTH: 9
<212> TYPE: PRT
<213> ORGANISM: Mus musculus

<400> SEQUENCE: 8

Gln Gln Ser Met Lys Val Pro Leu Thr
1               5

<210> SEQ ID NO 9
<211> LENGTH: 119
<212> TYPE: PRT
<213> ORGANISM: Mus musculus

<400> SEQUENCE: 9

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Arg Tyr
            20                  25                  30

Ala Met Ser Trp Val Arg Gln Ile Pro Glu Lys Arg Leu Glu Trp Val
        35                  40                  45

Ala Ala Ile Ser Ser Gly Gly Ser Leu Tyr Phe Pro Asp Ser Val Lys
    50                  55                  60

Gly Arg Phe Thr Ile Ser Arg Asp Asn Ala Arg Asn Ile Cys Tyr Leu
65                  70                  75                  80

Gln Met Asn Ser Leu Arg Ser Asp Asp Thr Ala Met Tyr Tyr Cys Ala
                85                  90                  95

Arg Gly Arg Glu Ala Asp Gly Gly Tyr Phe Asp Tyr Trp Gly Gln Gly
            100                 105                 110

Thr Thr Leu Thr Val Ser Ser
        115

<210> SEQ ID NO 10
<211> LENGTH: 357
<212> TYPE: DNA
<213> ORGANISM: Mus musculus

<400> SEQUENCE: 10
gaagtgaagc tggtggagtc tgggggaggc ttagtgaagc tggagggtc cctgaaactc        60 tcctgtgcag cctctggatt cactttcagt aggtatgcca tgtcttgggt tcgccagatt      120
ccagagaaga ggctggagtg ggtcgcagcc attagtagtg gtggtagttt atactttcca      180
gacagtgtga aggccgatt caccatctcc agagataatg ccaggaacat ctgctacctg       240
caaatgaaca gtctgaggtc tgacgacacg gccatgtatt actgtgcaag aggccgggag      300
gccgacggag gctactttga ctactgggc caaggcacca ctctcacagt ctcctca          357

<210> SEQ ID NO 11
<211> LENGTH: 111
<212> TYPE: PRT
<213> ORGANISM: Mus musculus -continued

<400> SEQUENCE: 11

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Met
                85                  90                  95

Lys Val Pro Leu Thr Phe Gly Ala Gly Thr Lys Leu Glu Leu Lys
            100                 105                 110

<210> SEQ ID NO 12
<211> LENGTH: 333
<212> TYPE: DNA
<213> ORGANISM: Mus musculus

<400> SEQUENCE: 12
gacattgtgc tcacccaatc tccagcttct ttggctgtgt ctctagggca gagagccacc    60
atctcctgca gagccagtga aagtgttgaa tattatggca aagtttaat gcagtggtac     120 caacagaaac caggacaacc acccaaactc ctcatctatg ctgcatccaa cgtagaatct    180
ggggtccctg ccaggtttag tggcagtggg tctgggacag acttcagcct caacatccat    240
cctgtggagg aggatgatat tgcaatgtat ttctgtcagc aaagtatgaa ggttcctctc    300
acgttcggtg ctgggaccaa gctggagctg aaa                                 333

<210> SEQ ID NO 13
<211> LENGTH: 448
<212> TYPE: PRT
<213> ORGANISM: Artificial Sequence
<220> FEATURE:
<223> OTHER INFORMATION: ch425 heavy chain pro

<400> SEQUENCE: 13

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Arg Tyr
            20                  25                  30

Ala Met Ser Trp Val Arg Gln Ile Pro Glu Lys Arg Leu Glu Trp Val
        35                  40                  45

Ala Ala Ile Ser Ser Gly Gly Ser Leu Tyr Phe Pro Asp Ser Val Lys
    50                  55                  60

Gly Arg Phe Thr Ile Ser Arg Asp Asn Ala Arg Asn Ile Cys Tyr Leu
65                  70                  75                  80

Gln Met Asn Ser Leu Arg Ser Asp Asp Thr Ala Met Tyr Tyr Cys Ala
                85                  90                  95

Arg Gly Arg Glu Ala Asp Gly Gly Tyr Phe Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Pro Ala Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Ala Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 14
<211> LENGTH: 1347
<212> TYPE: DNA
<213> ORGANISM: Artificial Sequence
<220> FEATURE:
<223> OTHER INFORMATION: ch425 heavy chain DNA

<400> SEQUENCE: 14
gaagtgaagc tggtggagtc tgggggaggc ttagtgaagc ctggagggtc cctgaaactc      60
tcctgtgcag cctctggatt cactttcagt aggtatgcca tgtctgggt tcgccagatt      120 ccagagaaga ggctggagtg ggtcgcagcc attagtagtg gtggtagttt atactttcca      180
gacagtgtga aggccgatt caccatctcc agagataatg ccaggaacat ctgctacctg      240
caaatgaaca gtctgaggtc tgacgacacg gccatgtatt actgtgcaag aggccgggag      300

```
gccgacggag gctactttga ctactggggc caaggcacca ctctcacagt ctcctcagcc    360
tccaccaagg gcccatcggt cttccccctg gcaccctcct ccaagagtac ttctgggggc    420
acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagaaagt tgagcccaaa    660
tcttgtgaca aaactcacac atgcccaccg tgcccagcac ctcctgctgc cggaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca agccgcggg aggagcagta caacagcacg    900
taccgtgtgg tcagcgtcct caccgtcctg caccaggact ggctgaatgg caaggagtac    960
aagtgcaagg tctccaacaa agccctcgcc gcccccatcg agaaaaccat ctccaaagcc   1020
aaagggcagc cccgagaacc acaggtgtac accctgcccc catcccggga tgagctgacc   1080
aagaaccagg tcagcctgac ctgcctggtc aaaggcttct atcccagcga catcgccgtg   1140
gagtgggaga gcaatgggca gccggagaac aactacaaga ccacgcctcc cgtgctggac   1200
tccgacggct ccttcttcct ctacagcaag ctcaccgtgg acaagagcag gtggcagcag   1260
gggaacgtct tctcatgctc cgtgatgcat gaggctctgc acaaccacta cacgcagaag   1320
agcctctccc tgtctccggg taaatga                                      1347
```

<210> SEQ ID NO 15
<211> LENGTH: 218
<212> TYPE: PRT
<213> ORGANISM: Artificial Sequence
<220> FEATURE:
<223> OTHER INFORMATION: ch425 light chain pro

<400> SEQUENCE: 15

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Met
                85                  90                  95

Lys Val Pro Leu Thr Phe Gly Ala Gly Thr Lys Leu Glu Leu Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175
```

```
Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215
```

<210> SEQ ID NO 16
<211> LENGTH: 657
<212> TYPE: DNA
<213> ORGANISM: Artificial Sequence
<220> FEATURE:
<223> OTHER INFORMATION: ch425 light chain DNA

<400> SEQUENCE: 16

```
gacattgtgc tcacccaatc tccagcttct ttggctgtgt ctctagggca gagagccacc      60
atctcctgca gagccagtga aagtgttgaa tattatggca caagtttaat gcagtggtac     120
caacagaaac caggacaacc acccaaactc ctcatctatg ctgcatccaa cgtagaatct     180
ggggtccctg ccaggtttag tggcagtggg tctgggacag acttcagcct caacatccat     240
cctgtggagg aggatgatat tgcaatgtat ttctgtcagc aaagtatgaa ggttcctctc     300
acgttcggtg ctgggaccaa gctggagctg aaacgggctg atgctgcacc aactgtatcc     360
atcttcccac catccagtga gcagttaaca tctggaggtg cctcagtcgt gtgcttcttg     420
aacaacttct accccaaaga catcaatgtc aagtggaaga ttgatggcag tgaacgacaa     480
aatggcgtcc tgaacagttg gactgatcag gacagcaaag acagcaccta cagcatgagc     540
agcaccctca cgttgaccaa ggacgagtat gaacgacata cagctatac ctgtgaggcc      600
actcacaaga catcaacttc acccattgtc aagagcttca caggaatga gtgttag         657
```

<210> SEQ ID NO 17
<211> LENGTH: 119
<212> TYPE: PRT
<213> ORGANISM: Artificial Sequence
<220> FEATURE:
<223> OTHER INFORMATION: hu425-1-1 VH pro

<400> SEQUENCE: 17

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ala Ala Ile Ser Ser Gly Gly Ser Leu Tyr Phe Pro Asp Ser Val Lys
    50                  55                  60

Gly Arg Phe Thr Ile Ser Arg Asp Asn Ala Lys Asn Ser Cys Tyr Leu
65                  70                  75                  80

Gln Met Asn Ser Leu Arg Ala Glu Asp Thr Ala Val Tyr Tyr Cys Ala
                85                  90                  95

Arg Gly Arg Glu Ala Asp Gly Gly Tyr Phe Asp Tyr Trp Gly Gln Gly
            100                 105                 110

Thr Leu Val Thr Val Ser Ser
        115
```

<210> SEQ ID NO 18
<211> LENGTH: 357
<212> TYPE: DNA

<210> SEQ ID NO 18
<211> LENGTH: 357
<212> TYPE: DNA
<213> ORGANISM: Artificial Sequence
<220> FEATURE:
<223> OTHER INFORMATION: hu425-1-1 VH DNA

<400> SEQUENCE: 18

```
gaagtgcagc tggtcgaatc agggggggggg ctggtgcagc ctggaggcag cctgagactg      60
tcctgcgccg cttctggctt cacctttagc agatacgcca tgtcctgggt gcggcaggct     120
cctggcaagg gactggagtg ggtggccgct atcagctccg gcggctccct gtacttcccc     180
gattccgtga agggccggtt caccatcagc agggacaacg ccaagaacag ctgctatctg     240
cagatgaact ctctgagggc cgaggataca gccgtgtact attgcgctcg ggcagagaa     300
gcagatggcg gctacttcga ctattgggc cagggcaccc tggtgacagt gtctagc        357
```

<210> SEQ ID NO 19
<211> LENGTH: 111
<212> TYPE: PRT
<213> ORGANISM: Artificial Sequence
<220> FEATURE:
<223> OTHER INFORMATION: hu425-1-1 VK pro

<400> SEQUENCE: 19

```
Asp Ile Val Leu Thr Gln Ser Pro Ala Thr Leu Ser Val Ser Pro Gly
1               5                   10                  15
Glu Arg Ala Thr Leu Ser Cys Arg Ala Ser Glu Ser Val Glu Tyr Tyr
            20                  25                  30
Gly Thr Ser Leu Met Gln Trp Tyr Gln Gln Lys Pro Gly Gln Ala Pro
        35                  40                  45
Arg Leu Leu Ile Tyr Ala Ala Ser Asn Val Glu Ser Gly Val Pro Ala
    50                  55                  60
Arg Phe Ser Gly Ser Gly Ser Gly Thr Asp Phe Thr Leu Thr Ile Ser
65                  70                  75                  80
Ser Leu Gln Ser Glu Asp Phe Ala Val Tyr Tyr Cys Gln Gln Ser Met
                85                  90                  95
Lys Val Pro Leu Thr Phe Gly Gly Gly Thr Lys Val Glu Ile Lys
            100                 105                 110
```

<210> SEQ ID NO 20
<211> LENGTH: 333
<212> TYPE: DNA
<213> ORGANISM: Artificial Sequence
<220> FEATURE:
<223> OTHER INFORMATION: hu425-1-1 VK DNA

<400> SEQUENCE: 20

```
gacatcgtcc tgactcagtc ccctgccact ctgtcagtga gcccaggaga gcgagctacc      60
ctgtcctgca gagcatccga gtctgtcgaa tactatggca cctctctgat gcagtggtac     120
cagcagaagc cagggcaggc tcccaggctg ctgatctatg ccgcttctaa cgtggagagt     180
ggcgtcccag cacgcttcag tggctcaggg agcggaacag actttaccct gacaattagc     240
tcccctgcaga gtgaagattt cgccgtgtac tattgccagc agagcatgaa ggtccccctg     300
acatttggcg ggggaactaa ggtggagatc aaa                                   333
```

<210> SEQ ID NO 21
<211> LENGTH: 329
<212> TYPE: PRT
<213> ORGANISM: Artificial Sequence
<220> FEATURE:
<223> OTHER INFORMATION: IgG1mf pro

```
<400> SEQUENCE: 21

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Pro Ala Ala Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Ala Ala Pro Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 22
<211> LENGTH: 448
<212> TYPE: PRT
<213> ORGANISM: Artificial Sequence
<220> FEATURE:
<223> OTHER INFORMATION: hu425-1-1 heavy chain pro

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
```

```
            20                  25                  30
Ala Met Ser Trp Val Arg Gln Ala Pro Gly Lys Gly Leu Glu Trp Val
            35                  40                  45
Ala Ala Ile Ser Ser Gly Gly Ser Leu Tyr Phe Pro Asp Ser Val Lys
            50                  55                  60
Gly Arg Phe Thr Ile Ser Arg Asp Asn Ala Lys Asn Ser Cys Tyr Leu
 65                  70                  75                  80
Gln Met Asn Ser Leu Arg Ala Glu Asp Thr Ala Val Tyr Tyr Cys Ala
                85                  90                  95
Arg Gly Arg Glu Ala Asp Gly Gly Tyr Phe Asp Tyr Trp Gly Gln Gly
                100                 105                 110
Thr Leu Val Thr Val Ser Ser Ala Ser Thr Lys Gly Pro Ser Val Phe
                115                 120                 125
Pro Leu Ala Pro Ser Ser Lys Ser Thr Ser Gly Gly Thr Ala Ala Leu
                130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
                195                 200                 205
Ser Asn Thr Lys Val Asp Lys Lys Val Glu Pro Lys Ser Cys Asp Lys
                210                 215                 220
Thr His Thr Cys Pro Pro Cys Pro Ala Pro Pro Ala Ala Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
                260                 265                 270
Glu Val Lys Phe Asn Trp Tyr Val Asp Gly Val Glu Val His Asn Ala
                275                 280                 285
Lys Thr Lys Pro Arg Glu Glu Gln Tyr Asn Ser Thr Tyr Arg Val Val
                290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Ala Ala Pro Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Arg Asp Glu Leu Thr Lys Asn Gln Val Ser Leu Thr Cys
                355                 360                 365
Leu Val Lys Gly Phe Tyr Pro Ser Asp Ile Ala Val Glu Trp Glu Ser
                370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly Lys
                435                 440                 445
```

<210> SEQ ID NO 23
<211> LENGTH: 1347
<212> TYPE: DNA
<213> ORGANISM: Artificial Sequence
<220> FEATURE:
<223> OTHER INFORMATION: hu425-1-1 heavy chain DNA

<400> SEQUENCE: 23

```
gaagtgcagc tggtcgaatc agggggggggg ctggtgcagc ctggaggcag cctgagactg      60
tcctgcgccg cttctggctt cacctttagc agatacgcca tgtcctgggt gcggcaggct     120
cctggcaagg gactggagtg ggtggccgct atcagctccg gcggctccct gtacttcccc     180
gattccgtga agggccggtt caccatcagc agggacaacg ccaagaacag ctgctatctg     240
cagatgaact ctctgagggc cgaggataca gccgtgtact attgcgctcg ggcagagaa      300
gcagatggcg gctacttcga ctattgggc cagggcaccc tggtgacagt gtctagcgct     360
agcaccaaag gccccagcgt gtttcctctg gctccatcct ctaaatccac ctctggcggc     420
acagccgctc tgggctgtct ggtgaaggat tacttcccag agcccgtgac agtgtcttgg     480
aacagcggcg ccctgacctc cggcgtgcac acatttcctg ctgtgctgca gagctccggc     540
ctgtacagcc tgtctagcgt ggtgaccgtg ccatcctcta gcctgggcac ccagacatat     600
atctgcaacg tgaatcacaa gcccagcaat acaaaggtgg ataagaaggt ggagccaaag     660
tcctgtgaca gacccacac atgccccct tgtcctgctc caccagctgc aggaccaagc       720
gtgttcctgt ttccacccaa gcccaaggat accctgatga tctctcggac cccagaggtg     780
acatgcgtgg tggtggatgt gagccacgag gaccccgagg tgaagttcaa ctggtatgtg     840
gacggcgtgg aggtgcacaa tgctaagacc aagcccaggg aggagcagta caactccacc     900
tatagagtgg tgtctgtgct gacagtgctg caccaggatt ggctgaacgg caaggagtat     960
aagtgcaagg tgtccaataa ggcccctggcc gctcctatcg agaagaccat ctctaaggcc    1020
aagggccagc ccagagagcc tcaggtgtac acactgcctc catcccggga tgagctgacc    1080
aagaaccagg tgtctctgac atgtctggtc aagggcttct atccctctga catcgccgtg    1140
gagtgggaga gcaatggcca gcctgagaac aattacaaga ccacaccccc tgtgctggat    1200
tccgacggct ctttctttct gtatagcaag ctgaccgtgg acaagtcccg gtggcagcag    1260
ggcaacgtgt tcagctgttc cgtgatgcac gaagctctgc ataatcacta tactcagaaa    1320
tccctgtcac tgtcacctgg taaatga                                         1347
```

<210> SEQ ID NO 24
<211> LENGTH: 218
<212> TYPE: PRT
<213> ORGANISM: Artificial Sequence
<220> FEATURE:
<223> OTHER INFORMATION: hu425-1-1 light chain pro

<400> SEQUENCE: 24

Asp Ile Val Leu Thr Gln Ser Pro Ala Thr Leu Ser Val Ser Pro Gly
1               5                   10                  15

Glu Arg Ala Thr Leu Ser Cys Arg Ala Ser Glu Ser Val Glu Tyr Tyr
            20                  25                  30

Gly Thr Ser Leu Met Gln Trp Tyr Gln Gln Lys Pro Gly Gln Ala Pro
        35                  40                  45

Arg Leu Leu Ile Tyr Ala Ala Ser Asn Val Glu Ser Gly Val Pro Ala
    50                  55                  60

```
Arg Phe Ser Gly Ser Gly Ser Gly Thr Asp Phe Thr Leu Thr Ile Ser
 65                  70                  75                  80

Ser Leu Gln Ser Glu Asp Phe Ala Val Tyr Tyr Cys Gln Gln Ser Met
                 85                  90                  95

Lys Val Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
210                 215
```

<210> SEQ ID NO 25
<211> LENGTH: 657
<212> TYPE: DNA
<213> ORGANISM: Artificial Sequence
<220> FEATURE:
<223> OTHER INFORMATION: hu425-1-1 light chain DNA

<400> SEQUENCE: 25

```
gacatcgtcc tgactcagtc ccctgccact ctgtcagtga gcccaggaga gcgagctacc      60
ctgtcctgca gagcatccga gtctgtcgaa tactatggca cctctctgat gcagtggtac     120
cagcagaagc cagggcaggc tcccaggctg ctgatctatg ccgcttctaa cgtggagagt     180
ggcgtcccag cacgcttcag tggctcaggg agcggaacag actttaccct gacaattagc     240
tccctgcaga gtgaagattt cgccgtgtac tattgccagc agagcatgaa ggtccccctg     300
acatttggcg ggggaactaa ggtggagatc aaacgaacag tggcagcccc ttccgtcttc     360
atttttcccc cttctgacga acagctgaaa tcaggaactg ctagcgtggt ctgtctgctg     420
aacaatttct accccagaga ggccaaggtg cagtggaaag tcgataacgc tctgcagtcc     480
ggcaattctc aggagagtgt gaccgaacag gactcaaagg atagcacata ttccctgtct     540
agtactctga ccctgagcaa agcagactac gagaagcaca agtgtatgc ctgtgaagtc     600
acacaccagg gctgagttc accagtcacc aagagtttca acagagggga atgctaa      657
```

<210> SEQ ID NO 26
<211> LENGTH: 16
<212> TYPE: PRT
<213> ORGANISM: Artificial Sequence
<220> FEATURE:
<223> OTHER INFORMATION: hu425-2-2 HCDR2

<400> SEQUENCE: 26

```
Ala Ile Ser Ser Gly Gly Ser Leu Tyr Tyr Pro Asp Ser Val Lys Gly
 1               5                  10                  15
```

<210> SEQ ID NO 27
<211> LENGTH: 9
<212> TYPE: PRT

<213> ORGANISM: Artificial Sequence
<220> FEATURE:
<223> OTHER INFORMATION: hu425-2-2 LCDR3

<400> SEQUENCE: 27

Gln Gln Ser Leu Lys Val Pro Leu Thr
1               5

<210> SEQ ID NO 28
<211> LENGTH: 119
<212> TYPE: PRT
<213> ORGANISM: Artificial Sequence
<220> FEATURE:
<223> OTHER INFORMATION: hu425-2-2 VH pro

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ala Ala Ile Ser Ser Gly Gly Ser Leu Tyr Tyr Pro Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Glu Ala Asp Gly Gly Tyr Phe Asp Tyr Trp Gly Gln Gly
            100                 105                 110

Thr Leu Val Thr Val Ser Ser
        115

<210> SEQ ID NO 29
<211> LENGTH: 357
<212> TYPE: DNA
<213> ORGANISM: Artificial Sequence
<220> FEATURE:
<223> OTHER INFORMATION: hu425-2-2 VH DNA

<400> SEQUENCE: 29
gaagtgcagc tggtcgaatc aggggggggg ctggtgcagc ctggaggcag cctgagactg    60
tcctgcgccg cttctggctt cacctttagc agatacgcca tgtcctgggt gcggcaggct   120
cctggcaagg gactggagtg ggtggccgct atcagctccg gcggctccct gtactatccc   180
gattccgtga agggccggtt caccatcagc aggacaacg ccaagaacac actgtatctg    240
cagatgaact ctctgagggc cgaggataca gccgtgtact attgcgctcg gggcagagaa   300
gcagatggcg gctacttcga ctattgggc cagggcaccc tggtgacagt gtctagc       357

<210> SEQ ID NO 30
<211> LENGTH: 111
<212> TYPE: PRT
<213> ORGANISM: Artificial Sequence
<220> FEATURE:
<223> OTHER INFORMATION: hu425-2-2 VK pro

<400> SEQUENCE: 30

Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Glu Tyr Tyr

```
            20                  25                  30
Gly Thr Ser Leu Met Gln Trp Tyr Gln Gln Lys Pro Gly Gln Ala Pro
        35                  40                  45

Arg Leu Leu Ile Tyr Ala Ala Ser Asn Val Glu Ser Gly Ile Pro Ala
 50                  55                  60

Arg Phe Ser Gly Ser Gly Ser Gly Thr Glu Phe Thr Leu Thr Ile Ser
 65                  70                  75                  80

Ser Leu Gln Ser Glu Asp Phe Ala Val Tyr Tyr Cys Gln Gln Ser Leu
                85                  90                  95

Lys Val Pro Leu Thr Phe Gly Gly Gly Thr Lys Val Glu Ile Lys
            100                 105                 110
```

<210> SEQ ID NO 31
<211> LENGTH: 333
<212> TYPE: DNA
<213> ORGANISM: Artificial Sequence
<220> FEATURE:
<223> OTHER INFORMATION: hu425-2-2 VK DNA

<400> SEQUENCE: 31

```
gagatcgtca tgactcagtc ccctgccact ctgtcagtga gcccaggaga gcgagctacc    60
ctgtcctgca gagcatccga gtctgtcgaa tactatggca cctctctgat gcagtggtac   120
cagcagaagc cagggcaggc tcccaggctg ctgatctatg ccgcttctaa cgtggagagt   180
ggcatcccag cacgcttcag tggctcaggg agcggaacag agtttaccct gacaattagc   240
tccctgcaga gtgaagattt cgccgtgtac tattgccagc agagcctgaa ggtcccctg   300
acatttggcg ggggaactaa ggtggagatc aaa                              333
```

<210> SEQ ID NO 32
<211> LENGTH: 448
<212> TYPE: PRT
<213> ORGANISM: Artificial Sequence
<220> FEATURE:
<223> OTHER INFORMATION: hu425-2-2 heavy chain pro

<400> SEQUENCE: 32

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ala Ala Ile Ser Ser Gly Gly Ser Leu Tyr Tyr Pro Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Arg Gly Arg Glu Ala Asp Gly Gly Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160
```

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Ala Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Ala Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 33
<211> LENGTH: 1347
<212> TYPE: DNA
<213> ORGANISM: Artificial Sequence
<220> FEATURE:
<223> OTHER INFORMATION: hu425-2-2 heavy chain DNA

<400> SEQUENCE: 33
gaagtgcagc tggtcgaatc agggggggggg ctggtgcagc ctggaggcag cctgagactg      60
tcctgcgccg cttctggctt cacctttagc agatacgcca tgtcctgggt gcggcaggct     120
cctggcaagg gactggagtg ggtggccgct atcagctccg gcggctccct gtactatccc     180
gattccgtga aggccggttt caccatcagc agggacaacg ccaagaacac actgtatctg     240
cagatgaact ctctgagggc cgaggataca gccgtgtact attgcgctcg gggcagagaa     300
gcagatggcg gctacttcga ctattggggc cagggcaccc tggtgacagt gtctagcgct     360
agcaccaaag gcccagcgt gtttcctctg gctccatcct ctaaatccac ctctggcggc     420
acagccgctc tgggctgtct ggtgaaggat tacttcccag agcccgtgac agtgtcttgg     480

```
aacagcggcg ccctgacctc cggcgtgcac acatttcctg ctgtgctgca gagctccggc    540
ctgtacagcc tgtctagcgt ggtgaccgtg ccatcctcta gcctgggcac ccagacatat    600
atctgcaacg tgaatcacaa gcccagcaat acaaaggtgg ataagaaggt ggagccaaag    660
tcctgtgaca gacccacaca tgccccccct tgtcctgctc accagctgc  aggaccaagc    720 gtgttcctgt ttccacccaa gcccaaggat accctgatga tctctcggac cccagaggtg    780
acatgcgtgg tggtggatgt gagccacgag gaccccgagg tgaagttcaa ctggtatgtg    840
gacggcgtgg aggtgcacaa tgctaagacc aagcccaggg aggagcagta caactccacc    900
tatagagtgg tgtctgtgct gacagtgctg caccaggatt ggctgaacgg caaggagtat    960
aagtgcaagg tgtccaataa ggccctggcc gctcctatcg agaagaccat ctctaaggcc   1020
aagggccagc cagagagcc  tcaggtgtac acactgcctc catcccggga tgagctgacc   1080
aagaaccagg tgtctctgac atgtctggtc aagggcttct atccctctga catcgccgtg   1140
gagtgggaga gcaatggcca gcctgagaac aattacaaga ccacaccccc tgtgctggat   1200
tccgacggct ctttctttct gtatagcaag ctgaccgtgg acaagtcccg gtggcagcag   1260
ggcaacgtgt tcagctgttc cgtgatgcac gaagctctgc ataatcacta tactcagaaa   1320
tccctgtcac tgtcacctgg taaatga                                       1347

<210> SEQ ID NO 34
<211> LENGTH: 218
<212> TYPE: PRT
<213> ORGANISM: Artificial Sequence
<220> FEATURE:
<223> OTHER INFORMATION: hu425-2-2 light chain pro

<400> SEQUENCE: 34

Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Glu Tyr Tyr
            20                  25                  30

Gly Thr Ser Leu Met Gln Trp Tyr Gln Gln Lys Pro Gly Gln Ala Pro
        35                  40                  45

Arg Leu Leu Ile Tyr Ala Ala Ser Asn Val Glu Ser Gly Ile Pro Ala
    50                  55                  60

Arg Phe Ser Gly Ser Gly Ser Gly Thr Glu Phe Thr Leu Thr Ile Ser
65                  70                  75                  80

Ser Leu Gln Ser Glu Asp Phe Ala Val Tyr Tyr Cys Gln Gln Ser Leu
                85                  90                  95

Lys Val Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205
```

Val Thr Lys Ser Phe Asn Arg Gly Glu Cys
        210                 215

<210> SEQ ID NO 35
<211> LENGTH: 657
<212> TYPE: DNA
<213> ORGANISM: Artificial Sequence
<220> FEATURE:
<223> OTHER INFORMATION: hu425-2-2 light chain DNA

<400> SEQUENCE: 35
gagatcgtca tgactcagtc ccctgccact ctgtcagtga gcccaggaga gcgagctacc      60
ctgtcctgca gagcatccga gtctgtcgaa tactatggca cctctctgat gcagtggtac     120
cagcagaagc cagggcaggc tcccaggctg ctgatctatg ccgcttctaa cgtggagagt     180
ggcatcccag cacgcttcag tggctcaggg agcggaacag agtttaccct gacaattagc     240
tccctgcaga gtgaagattt cgccgtgtac tattgccagc agagcctgaa ggtccccctg     300
acatttggcg ggggaactaa ggtggagatc aaacgaacag tggcagcccc ttccgtcttc     360
atttttcccc cttctgacga acagctgaaa tcaggaactg ctagcgtggt ctgtctgctg     420
aacaatttct accccagaga ggccaaggtg cagtggaaag tcgataacgc tctgcagtcc     480
ggcaattctc aggagagtgt gaccgaacag gactcaaagg atagcacata ttccctgtct     540
agtactctga ccctgagcaa agcagactac gagaagcaca agtgtatgc ctgtgaagtc     600 acacaccagg ggctgagttc accagtcacc aagagtttca acagggggga atgctaa       657

<210> SEQ ID NO 36
<211> LENGTH: 111
<212> TYPE: PRT
<213> ORGANISM: Artificial Sequence
<220> FEATURE:
<223> OTHER INFORMATION: hu425-2-3b VK pro

<400> SEQUENCE: 36

Glu Ile Val Leu Thr Gln Ser Pro Ala Thr Leu Ser Val Ser Pro Gly
1               5                   10                  15

Glu Arg Ala Thr Leu Ser Cys Arg Ala Ser Glu Ser Val Glu Tyr Tyr
            20                  25                  30

Gly Thr Ser Leu Met Gln Trp Tyr Gln Gln Lys Pro Gly Gln Ala Pro
        35                  40                  45

Arg Leu Leu Ile Tyr Ala Ala Ser Asn Val Glu Ser Gly Ile Pro Ala
    50                  55                  60

Arg Phe Ser Gly Ser Gly Ser Gly Thr Glu Phe Thr Leu Thr Ile Ser
65                  70                  75                  80

Ser Leu Gln Ser Glu Asp Phe Ala Val Tyr Tyr Cys Gln Gln Ser Leu
                85                  90                  95

Lys Val Pro Leu Thr Phe Gly Gly Gly Thr Lys Val Glu Ile Lys
            100                 105                 110

<210> SEQ ID NO 37
<211> LENGTH: 333
<212> TYPE: DNA
<213> ORGANISM: Artificial Sequence
<220> FEATURE:
<223> OTHER INFORMATION: hu425-2-3b VK DNA

<400> SEQUENCE: 37
gagatcgtcc tgactcagtc ccctgccact ctgtcagtga gcccaggaga gcgagctacc      60

```
ctgtcctgca gagcatccga gtctgtcgaa tactatggca cctctctgat gcagtggtac      120
cagcagaagc cagggcaggc tcccaggctg ctgatctatg ccgcttctaa cgtggagagt      180
ggcatcccag cacgcttcag tggctcaggg agcggaacag agtttaccct gacaattagc      240
tccctgcaga gtgaagattt cgccgtgtac tattgccagc agagcctgaa ggtccccctg      300
acatttggcg ggggaactaa ggtggagatc aaa                                  333
```

<210> SEQ ID NO 38
<211> LENGTH: 218
<212> TYPE: PRT
<213> ORGANISM: Artificial Sequence
<220> FEATURE:
<223> OTHER INFORMATION: hu425-2-3b light chain pro

<400> SEQUENCE: 38

```
Glu Ile Val Leu Thr Gln Ser Pro Ala Thr Leu Ser Val Ser Pro Gly
1               5                   10                  15

Glu Arg Ala Thr Leu Ser Cys Arg Ala Ser Glu Ser Val Glu Tyr Tyr
            20                  25                  30

Gly Thr Ser Leu Met Gln Trp Tyr Gln Gln Lys Pro Gly Gln Ala Pro
        35                  40                  45

Arg Leu Leu Ile Tyr Ala Ala Ser Asn Val Glu Ser Gly Ile Pro Ala
    50                  55                  60

Arg Phe Ser Gly Ser Gly Ser Gly Thr Glu Phe Thr Leu Thr Ile Ser
65                  70                  75                  80

Ser Leu Gln Ser Glu Asp Phe Ala Val Tyr Tyr Cys Gln Gln Ser Leu
                85                  90                  95

Lys Val Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 39
<211> LENGTH: 657
<212> TYPE: DNA
<213> ORGANISM: Artificial Sequence
<220> FEATURE:
<223> OTHER INFORMATION: hu425-2-3b light chain DNA

<400> SEQUENCE: 39

```
gagatcgtcc tgactcagtc ccctgccact ctgtcagtga gcccaggaga gcgagctacc      60
ctgtcctgca gagcatccga gtctgtcgaa tactatggca cctctctgat gcagtggtac      120
cagcagaagc cagggcaggc tcccaggctg ctgatctatg ccgcttctaa cgtggagagt      180
ggcatcccag cacgcttcag tggctcaggg agcggaacag agtttaccct gacaattagc      240
```

```
tccctgcaga gtgaagattt cgccgtgtac tattgccagc agagcctgaa ggtccccctg    300
acatttggcg ggggaactaa ggtggagatc aaacgaacag tggcagcccc ttccgtcttc    360
attttccccc cttctgacga acagctgaaa tcaggaactg ctagcgtggt ctgtctgctg    420
aacaatttct accccagaga ggccaaggtg cagtggaaag tcgataacgc tctgcagtcc    480
ggcaattctc aggagagtgt gaccgaacag gactcaaagg atagcacata ttccctgtct    540
agtactctga ccctgagcaa agcagactac gagaagcaca agtgtatgc ctgtgaagtc     600 acacaccagg ggctgagttc accagtcacc aagagtttca acagagggga atgctaa       657
```

<210> SEQ ID NO 40
<211> LENGTH: 118
<212> TYPE: PRT
<213> ORGANISM: Artificial Sequences
<220> FEATURE:
<223> OTHER INFORMATION: humanized anti-Tim-3 antibody VH region

<400> SEQUENCE: 40

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Met
        35                  40                  45

Gly Asp Ile Tyr Pro Gly Asn Gly Asp Thr Ser Tyr Asn Gln Lys Phe
    50                  55                  60

Lys Gly Arg Val Thr Ile Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Thr Val Thr Val Ser Ser
        115
```

<210> SEQ ID NO 41
<211> LENGTH: 111
<212> TYPE: PRT
<213> ORGANISM: Artificial Sequences
<220> FEATURE:
<223> OTHER INFORMATION: humanized anti-Tim-3 antibody VK region

<400> SEQUENCE: 41

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Glu Tyr Tyr
            20                  25                  30

Gly Thr Ser Leu Met Gln Trp Tyr Gln Gln Lys Pro Gly Lys Ala Pro
        35                  40                  45

Lys Leu Leu Ile Tyr Ala Ala Ser Asn Val Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Phe Cys Gln Gln Ser Arg
                85                  90                  95

Lys Asp Pro Ser Thr Phe Gly Gly Gly Thr Lys Val Glu Ile Lys
            100                 105                 110
```

```
<210> SEQ ID NO 42
<211> LENGTH: 114
<212> TYPE: PRT
<213> ORGANISM: Artificial Sequences
<220> FEATURE:
<223> OTHER INFORMATION: humanized anti-Tim-3 antibody VH region

<400> SEQUENCE: 42

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser
            20                  25                  30

Tyr Asp Met Ser Trp Val Arg Gln Ala Pro Gly Lys Gly Leu Asp Trp
        35                  40                  45

Val Ser Thr Ile Ser Gly Gly Thr Tyr Thr Tyr Tyr Gln Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Ser Met Asp Tyr Trp Gly Gln Gly Thr Thr Val Thr Val Ser
            100                 105                 110

Ser Ala

<210> SEQ ID NO 43
<211> LENGTH: 108
<212> TYPE: PRT
<213> ORGANISM: Artificial Sequences
<220> FEATURE:
<223> OTHER INFORMATION: humanized anti-Tim-3 antibody VK region

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Arg Tyr
            20                  25                  30

Leu Asn Trp Tyr His Gln Lys Pro Gly Lys Ala Pro Lys Leu Leu Ile
        35                  40                  45

Tyr Gly Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Ser His Ser Ala Pro Leu
                85                  90                  95

Thr Phe Gly Gly Gly Thr Lys Val Glu Ile Lys Arg
            100                 105
```